US007442703B2

(12) United States Patent
Palani et al.

(10) Patent No.: US 7,442,703 B2
(45) Date of Patent: Oct. 28, 2008

(54) PIPERIDINE DERIVATIVES USEFUL AS CCR5 ANTAGONISTS

(75) Inventors: Anandan Palani, Bridgewater, NJ (US); Michael W. Miller, Westfield, NJ (US); Jack D. Scott, Springfield, NJ (US)

(73) Assignee: Schering Corporation, Kenilworth, NJ (US)

( * ) Notice: Subject to any disclaimer, the term of this patent is extended or adjusted under 35 U.S.C. 154(b) by 83 days.

(21) Appl. No.: 10/629,466

(22) Filed: Jul. 29, 2003

(65) Prior Publication Data

US 2004/0092551 A1    May 13, 2004

Related U.S. Application Data

(62) Division of application No. 10/229,466, filed on Aug. 28, 2002, now abandoned.

(60) Provisional application No. 60/315,683, filed on Aug. 29, 2001.

(51) Int. Cl.
*A61K 31/505* (2006.01)
*C07D 401/14* (2006.01)

(52) U.S. Cl. ..................... 514/256; 544/333

(58) Field of Classification Search ............... 514/256, 514/316; 544/333; 546/187, 186
See application file for complete search history.

(56) References Cited

U.S. PATENT DOCUMENTS

| 5,952,349 A | 9/1999 | Asberom et al. | 514/316 |
|---|---|---|---|
| 2004/0142920 A1* | 7/2004 | Albert et al. | 514/217 |

FOREIGN PATENT DOCUMENTS

| EP | 0 151 824 | 8/1985 |
|---|---|---|
| EP | 0 855 999 | 10/2001 |
| WO | WO 97/24324 | 7/1997 |
| WO | WO 98/01425 | 1/1998 |
| WO | WO 01/30348 | 5/2001 |
| WO | WO 01/77101 | 10/2001 |
| WO | WO 02/081449 | 10/2002 |
| WO | WO02/081449 | * 10/2002 |

OTHER PUBLICATIONS

Janssens et al. "N-r-piperidinyl bicyclcic . . . " Ca 104:50874 (1986).*
Braga et al. "Making crystals from crystals . . . " Chem. Commun. (2005) p. 3635-3645.*
Anandan Palani et al., "Discovery of 4-[(Z)-(4-Bromophenyl)-(ethoxyimino)methyl]-1'-[(2,4—dimethyl-3-pyridinyl)carbonyl]-4'-methyl-1,4'-bipiperidine N-Oxide (SCH 351125): An Orally Bioavailable Human CCR5 Antagonist for the Treatment of HIV Infection", Journal of Medicinal Chemistry, vol. 44, No. 21, Oct. 11, 2001, pp. 3339-3342.
Molla et al., "Human Serum Attenuates the Activity of Protease Inhibitors toward Wild-Type and Mutant Human Immunodeficiency Virus", Virology (1998), p. 255-262, vol. 250.

Peterson et al., "Influence of Protein Bindingon Therapeutic Efficacy of Cefoperazone", Antimicrobial Agents and Chemotherapy (Apr. 1989), p. 566-568, vol. 33, No. 4.
Peterson et al., "Effect of Protein Binding on Simulated Intravascular and Extravascular Kinetics of Cefotaxime in an In Vitro Model", Antimicrobial Agents and Chemotherapy (Jan. 1984), p. 58-61, vol. 25, No. 1.
Bilello et al., "Human Serum $\alpha_1$ Acid Glycoprotein Reduces Uptake, Intracellular Concentration, and Antiviral Activity of A-80987, an Inhibitor or the Human Immunodeficiency Virus Type 1 Protease", Antimicrobial Agents and Chemotherapy, (Jun. 1996), p. 1491-1497. vol. 40, No. 6, American Society for Microbiology.
Bilello et al., "Reduction of the in Vitro Activity of A77003, an Inhibitor of Human Immunodeficiency Virus Protease, by Human Serum $\alpha_1$ Acid Glycoprotein", The Journal of Infectious Diseases, (1995), p. 546-51, vol. 171.
Bryant et al., "SC-52151, a Novel Inhibitor of the Human Immunodeficiency Virus Protease", Antimicrobial Agents and Chemotherapy, (Oct. 1995), p. 2229-2234, vol. 39, No. 10, American Society for Microbiology.
Fischl et al., "Phase I/II Study of the Toxicity, Pharmacokinetics, and Activity of the HIV Protease Inhibitor SC-52151", Journal of Acquired Immune Deficiency Syndromes and Human Retrovirology, (1997), p. 28-34, vol. 15, No. 1, Lippincott-Raven Publishers, Philadelphia.

(Continued)

*Primary Examiner*—Celia Chang
(74) *Attorney, Agent, or Firm*—Krishna G. Banerjee

(57) ABSTRACT

The present invention provides a compound of the formula

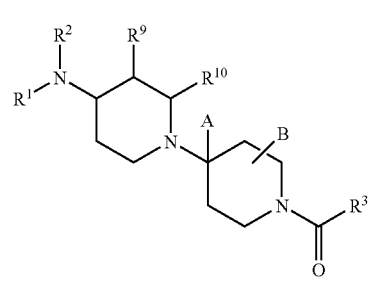

I or a pharmaceutically acceptable salt or solvate thereof, wherein $R^1$, $R^2$, $R^3$, $R^9$, $R^{10}$, A and B are as defined in the specification. The present invention also provides pharmaceutical compositions containing the compound of this invention, and methods of treatment using the compound of this invention. The invention also relates to the use of a combination of a compound of this invention and one or more antiviral or other agents useful in the treatment of Human Immunodeficiency Virus (HIV). The invention further relates to the use of a compound of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis.

10 Claims, No Drawings

OTHER PUBLICATIONS

Goldberg et al., "DuP 532, an angiotensin II receptor antagonist: First administration and Comparison with losartan", Clinical Pharmacology & Therapeutics, (Jan. 1997), p. 59-69, vol. 61, No. 1.

Maillard et al., "Does protein binding modulate the effect of angiotensin II receptor antagonists?", Journal of the Renin-Angiotensin-Aldosterone System, (Mar. 2001), p. S54-S58, vol. 2, Supplement 1.

Trainor, "The importance of plasma protein binding in drug discovery", Expert Opin. Drug Discov., (2007), p. 51-64, vol. 2, No. 1.

* cited by examiner

PIPERIDINE DERIVATIVES USEFUL AS CCR5 ANTAGONISTS

CROSS REFERENCE TO RELATED APPLICATION

The following application is a Divisional Application of U.S. patent application Ser. No. 10/229,466, filed Aug. 28, 2002 now abandoned, which claims priority to U.S. Provisional Application 60/315,683, filed Aug. 29, 2001.

FIELD OF INVENTION

The present invention relates to piperidine derivatives useful as selective CCR5 antagonists, pharmaceutical compositions containing the compound of this invention, and methods of treatment using the inventive compounds. The invention also relates to the use of a combination of the compound of this invention and one or more antiviral or other agents useful in the treatment of Human Immunodeficiency Virus (HIV). The invention further relates to the use of the compound of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis.

BACKGROUND OF INVENTION

The global health crisis caused by HIV, the causative agent of Acquired Immunodeficiency Syndrome (AIDS), is unquestioned. While recent advances in drug therapies have been successful in slowing the progression of AIDS, there is still a need to find a safer, more efficient, less expensive way to control the virus.

It has been reported that the CCR5 gene plays a role in resistance to HIV infection. HIV infection begins by attachment of the virus to a target cell membrane through interaction with the cellular receptor CD4 and a secondary chemokine co-receptor molecule, and proceeds by replication and dissemination of infected cells through the blood and other tissue. There are various chemokine receptors, but for macrophage-tropic HIV, believed to be the key pathogenic strain that replicates in vivo in the early stages of infection, the principal chemokine receptor required for the entry of HIV into the cell is CCR5. Therefore, interfering with the interaction between the viral receptor CCR5 and HIV can block HIV entry into the cell. The present invention relates to small molecules which are CCR5 antagonists.

CCR5 receptors have been reported to mediate cell transfer in inflammatory diseases such as arthritis, rheumatoid arthritis, atopic dermatitis, psoriasis, asthma and allergies. Inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

Other piperidine derivatives, which are muscarinic antagonists useful in the treatment of cognitive disorders such as Alzheimer's disease, are disclosed in U.S. Pat. Nos. 5,883,096, 6,037,352, 5,889,006, 5,952,349, and 5,977,138.

A-M. Vandamme et al., *Antiviral Chemistry & Chemotherapy*, 9:187-203 (1998) disclose current clinical treatments of HIV-1 infections in man including at least triple drug combinations or so-called Highly Active Antiretroviral Therapy ("HAART"). HAART involves various combinations of nucleoside reverse transcriptase inhibitors ("NRTI"), non-nucleoside reverse transcriptase inhibitors ("NNRTI") and HIV protease inhibitors ("PI"). In compliant drug-naive patients, HAART is effective in reducing mortality and the progression of HIV-1 to AIDS. However, these multidrug therapies do not eliminate HIV-1 and long-term treatment usually results in multidrug resistance. Development of new drug therapies to provide better HIV-1 treatment remains a priority.

SUMMARY OF THE INVENTION

The present invention provides a novel class of compounds as antagonists of the CCR5 receptor, methods of preparing such compounds, pharmaceutical compositions containing one or more such compounds, and methods of treatment, prevention or amelioration of one or more diseases associated with the CCR5 receptor.

One aspect of the invention relates to a compound having the general structure shown in Formula 1:

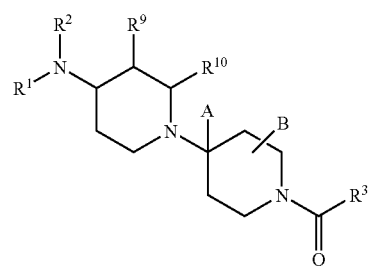

or a pharmaceutically acceptable salt or solvate thereof; wherein: $R^1$ is

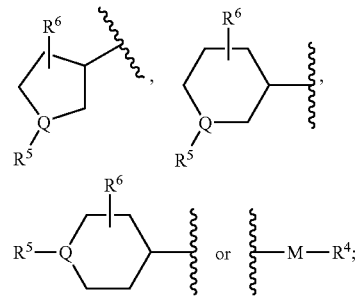

$R^2$ is selected from the group consisting of H, alkyl, aryl, arylalkyl, heteroarylalkyl, alkylketone, arylketone, alkyl, haloalkyl, cycloalkyl, cycloheteroalkyl, cycloalkylalkyl, alkylsulfonyl, arylsulfonyl, alkoxyalkyl, or amide;

$R^3$ is selected from the group consisting of aryl, 6-membered heteroaryl, fluorenyl; and diphenylmethyl, 6 membered heteroaryl-N-oxide,

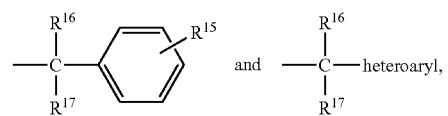

wherein said aryl, fluorenyl, diphenyl or heteroaryl is optionally substituted with 1-4 substituents which can be the same or different and are independently selected from the group consisting of $R^{11}$, $R^{12}$, $R^{13}$, $R^{14}$ and $R^{15}$;

$R^4$ is 1-3 substituents selected from the group consisting of H, halo, alkyl, haloalkyl, alkoxy, cycloalkyl, cycloheteroalkyl, amide, $CF_3$, $OCF_3$, aryl, heteroaryl, —$XR^7$, —C(O)$C_3$-$C_8$cycloalkyl, —C(O)$C_3$-$C_8$cycloheteroalkyl, —($C_1$-$C_6$)alkyl-N($R^{21}$)$SO_2R^{22}$, —($C_1$-$C_6$)alkyl-C(O)$NR^{20}R^{21}$, —CN, —$CO_2H$, —$CO_2R^{22}$, $R^8$-aryl($C_1$-$C_6$)alkyl-, $R^8$-heteroaryl($C_1$-$C_6$)alkyl-, —C(O)—($C_1$-$C_6$)alkyl, $R^8$-aryl-C(O)—, —C(O)$NR^{21}R^{22}$, —C(O)$NH_2$, —C(O)N(H)OH, —($C_1$-$C_6$)alkyl-N(R)C(O)$R^{22}$, —($C_1$-$C_6$)alkyl-N($R^{21}$)CO $R^{22}$, —($C_1$-$C_6$)alkyl-N($R^{21}$)C(O)$NR^{21}R^{22}$, —($C_1$-$C_6$)alkyl-$NR^{21}$ $R^{22}$, —($C_1$-$C_6$)alkyl-$NH_2$, ($C_1$-$C_6$)alkyl$SO_2NR^{21}R^{22}$ and —$SO_2NR^{21}R^{22}$, wherein $R^4$ can be the same or different and is independently selected when there is more than one $R^4$ present;

$R^5$ is selected from the group consisting of H, arylalkyl, ($C_1$-$C_6$)alkyl, $R^8$-aryl($C_1$-$C_6$)alkyl-, $R^8$-heteroaryl($C_1$-$C_6$)alkyl-, —$SO_2$—($C_1$-$C_6$)alkyl, —$SO_2$—($C_3$-$C_6$)cycloalkyl, —$SO_2$-aryl, $R^8$-aryl-$SO_2$—, —C(O)—($C_1$-$C_6$)alkyl, —C(O)—($C_4$-$C_6$)cycloalkyl, $R^8$-aryl-C(O)—, —C(O)$NR^{21}R^{22}$, and —$SO_2NR^{21}R^{22}$;

$R^6$ is H, —($C_1$-$C_6$)alkyl, or —($C_1$-$C_6$)haloalkyl;

$R^7$ is selected from the group consisting of aryl, substituted aryl, heteroaryl, alkyl, haloalkyl and cycloalkyl;

$R^8$ is 1, 2 or 3 substituents selected from the group consisting of H, halo, ($C_1$-$C_6$)alkyl, ($C_1$-$C_6$)alkoxy, —$CF_3$, —$OCF_3$, $CH_3C(O)$—, —CN, $CH_3SO_2$—, $CF_3SO_2$— and —$NH_2$, wherein $R^8$ can be the same or different and is independently selected when there are more than one $R^8$ present;

$R^9$, $R^{10}$ and B can be the same or different and are each independently selected from the group consisting of hydrogen, ($C_1$-$C_6$)alkyl, and —($C_1$-$C_6$)haloalkyl;

$R^{11}$ and $R^{12}$ can be the same or different and are each independently selected from the group consisting of ($C_1$-$C_6$)alkyl, —($C_1$-$C_6$)haloalkyl, halogen, —$NR^{19}R^{20}$, —OH, $CF_3$, —$OCH_3$, —O-acyl, and —$OCF_3$;

$R^{13}$ is selected from the group consisting of hydrogen, $R^{11}$, H, phenyl, —$NO_2$, —CN, —$CH_2F$, —$CHF_2$, —CHO, —CH=$NOR^{19}$, pyridyl-N-oxide, pyrimidinyl, pyrazinyl, N($R_{20}$)$CONR_{20}R_{21}$, —NHCONH(chloro-($C_1$-$C_6$)alkyl, —NHCONH(($C_3$-$C_{10}$)-cycloalkyl($C_1$-$C_6$)alkyl), —NHCO($C_1$-$C_6$)alkyl, —$NHCOCF_3$, —$NHCOCF_3$, —$NHSO_2N$(($C_1$-$C_6$)alkyl)$_2$, —$NHSO_2$($C_1$-$C_6$)alkyl, —N($SO_2CF_3$)$_2$, —$NHCO_2$($C_1$-$C_6$)alkyl, ($C_3$-$C_{10}$)cycloalkyl, —$SR^{22}$, —$SOR^{22}$, —$SO_2R^{22}$, —$SO_2NH$($C_1$-$C_6$ alkyl), —$OSO_2$($C_1$-$C_6$)alkyl, —$OSO_2CF_3$, hydroxy($C_1$-$C_6$)alkyl , —$CONR^{19}R^{20}$, —CON($CH_2CH_2$—O—$CH_3$)$_2$, —OCONH($C_1$-$C_6$)alkyl, —$CO_2R_{19}$, —$Si(CH_3)_3$ and —B($OC(CH_3)_2$)$_2$;

$R^{14}$ is selected from the group consisting of ($C_1$-$C_6$)alkyl, —($C_1$-$C_6$)haloalkyl —$NH_2$ and $R^{15}$-phenyl;

$R^{15}$ is 1-3 substituents selected from the group consisting of hydrogen, ($C_1$-$C_6$)alkyl, —($C_1$-$C_6$)haloalkyl, —$CF_3$, —$CO_2R^{20}$, —CN, ($C_1$-$C_6$)alkoxy and halogen; wherein $R^{15}$ can be the same or different and is independently selected when there are more than one $R^{15}$ present;

$R^{16}$ and $R^{17}$ can each be the same or different and are each independently selected from the group consisting of hydrogen and ($C_1$-$C_6$)alkyl, or $R^{16}$ and $R^{17}$ together are a $C_2$-$C_5$ alkylene group and with the carbon to which they are attached form a spiro ring of 3 to 6 carbon atoms;

$R^{19}$, $R^{20}$ and $R^{21}$ can each be the same or different and are each independently selected from the group consisting of H, ($C_1$-$C_6$)alkyl and ($C_3$-$C_6$)cycloalkyl;

$R^{22}$ is selected from the group consisting of ($C_1$-$C_6$)alkyl, —($C_1$-$C_6$)haloalkyl, ($C_2$-$C_6$)hydroxyalkyl, ($C_2$-$C_6$)alkylene, ($C_3$-$C_6$)cycloalkyl, aryl and aryl($C_1$-$C_6$)alkyl-;

A is selected from the group consisting of H, ($C_1$-$C_6$)alkyl, and ($C_2$-$C_6$) alkenyl.

M is aryl or heteroaryl optionally substituted with $R^4$;

Q is CH or N; and

X is selected from the group consisting of $CH_2$ $SO_2$, SO, S, and O, with the following proviso:

when $R^1$ is phenyl, pyridyl, thiophenyl or naphthyl, $R^2$ cannot be H, —($C_1$-$C_6$)alkyl or —C(O)—($C_1$-$C_6$)alkyl.

Another aspect of the invention relates to a pharmaceutical composition for treatment of HIV comprising one or more compounds of formula I.

Yet another aspect of the invention relates to a method of treating Human Immunodeficiency Virus comprising administering to a patient in need of such treatment a therapeutically effective amount of one or more compounds of formula I. A further aspect of the invention relates to a method of treating solid organ transplant rejection, graft v. host disease, arthritis, rheumatoid arthritis, inflammatory bowel disease, atopic dermatitis, psoriasis, asthma, allergies or multiple sclerosis comprising administering to a patient in need of such treatment a therapeutically effective amount of one or more compounds of formula I.

Still another aspect of this invention relates to a method of treating Human Immuno-deficiency Virus comprising administering to a patient in need of such treatment the one or more compounds of formula I in combination with one or more antiviral or other agents useful in the treatment. A further aspect of this invention relates to a method of treating solid organ transplant rejection, graft v. host disease, arthritis, rheumatoid arthritis, inflammatory bowel disease, atopic dermatitis, psoriasis, asthma or allergies comprising administering to a patient in need of such treatment one or more compounds of formula I in combination with one or more antiviral or other agents useful in the treatment.

The CCR5 and antiviral or other agents which are components of the combination can be administered in a single dosage or administered separately. A kit comprising separate dosage forms of the actives is also contemplated.

DETAILED DESCRIPTION OF THE INVENTION

The present invention relates to a compound having the general structure shown in Formula I:

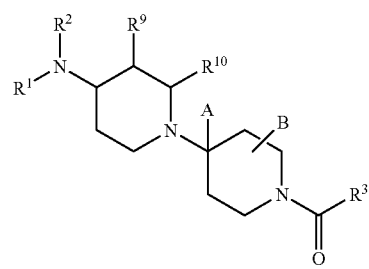

or a pharmaceutically acceptable salt or solvate thereof; wherein:

wherein $R^1$, $R^2$, $R^3$, $R^9$, $R^{10}$, A and B are defined as above.

When $R_1$ is

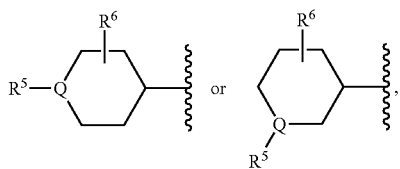

$Q$ is preferably CH or N, and $R^2$ is preferably alkyl, aryl or benzyl.

When $R_1$ is M-$R^4$, R2 is preferably benzyl, phenyl or cyclopropylmethly.

As used herein, the following terms are used as defined below unless otherwise indicated.

"Alkyl" means an aliphatic hydrocarbon group which may be straight or branched and comprising 1 to about 20 carbon atoms in the chain. Preferred alkyl groups contain 1 to about 12 carbon atoms in the chain. More preferred alkyl groups contain 1 to about 6 carbon atoms in the chain. Branched alkyl means that one or more lower alkyl groups such as methyl, ethyl or propyl, are attached to a linear alkyl chain. "Lower alkyl" means a group having about 1 to about 6 carbon atoms in the chain which may be straight or branched. Preferred alkyl groups in the present invention are lower alkyl groups. Non-limiting examples of suitable alkyl groups include methyl, ethyl, n-propyl, isopropyl, n-butyl, t-butyl, n-pentyl, heptyl, nonyl, decyl, trifluoromethyl and cyclopropylmethyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" or "halogenated alkyl" means alkyl having one or more halo atom substituents. Preferably, the haloalkyl is a haloalkyl. Non-limiting examples include —$CH_2Cl$, —$CHCl_2$, —$CCl_3$, —$CH_2F$, —$CHF_2$, —$CF_3$, —$CH_2$—$CH_2F$, —$CH_2CHF_2$, —$CH_2CF_3$ and —$CF_2CF_3$.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylamino, arylamino, alkylaryl, aralkenyl, heteroaralkyl, alkylheteroaryl, heteroaralkenyl, hydroxy, hydroxyalkyl, alkoxy, aryloxy, aralkoxy, aralkyloxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Cycloalkyl" means a non-aromatic mono- or multicyclic fused ring system comprising 3 to 10 ring carbon atoms, preferably 3 to 7 ring carbon atoms, more preferably 3 to 6 ring carbon atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornenyl, adamantyl and the like.

"Cycloheteroalkyl" means a non-aromatic mono- or multicyclic fused ring system comprising 3 to 10 ring carbon atoms, preferably 3 to 7 ring carbon atoms, more preferably 3 to 6 ring carbon atoms, wherein the cycloheteroaryl has 1 or 2 heteroatoms independently selected from O, S or N, said heteroatom(s) interrupting a carbocyclic ring structure provided that the rings do not contain adjacent oxygen and/or sulfur atoms. The cycloheteroalkyl can be optionally substituted with one or more "ring system substituents" which may be the same or different, and are as defined above.

"Aryl" means an aromatic monocyclic or multicyclic ring system comprising 6 to 14 ring carbon atoms, preferably 6 to 10 ring carbon atoms. The aryl group can be optionally substituted with one or more "ring system substituents" which may be the same or different, and are as defined herein. Non-limiting examples of suitable aryl groups include phenyl and naphthyl.

"Heteroaryl" represents cyclic aromatic groups of 5 or 6 ring atoms or bicyclic groups of 11 to 12 ring atoms having 1 or 2 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. Preferred heteroaryls contain 5 to 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. Nitrogen atoms can form an N-oxide. All regioisomers are contemplated, e.g., 2-pyridyl, 3-pyridyl and 4-pyridyl. Useful 6-membered heteroaryl groups include pyridyl, pyrimidinyl, pyrazinyl, pyridazinyl and the like and the N-oxides thereof. Useful 5-membered heteroaryl rings include furyl, thienyl, pyrrolyl, thiazolyl, isothiazolyl, imidazolyl, pyrazolyl, isoxazolyl and the like. Useful bicyclic groups include benzo-fused ring systems derived from the heteroaryl groups named above, e.g. quinolyl, phthalazinyl, quinazolinyl, benzofuranyl, benzothienyl, indolyl and the like.

Amide is represented by $RCONH_2$ wherein one or both of the hydrogen atoms in $RCONH_2$ can be substituted by an alkyl group and alkyl has the same meaning as defined above.

Arylalkyl or aralkyl represents a moiety containing an aryl group linked to the main group or ring via an alkyl.

Alkylketone represents a moiety containing an alkyl group linked to the main group or ring via a ketone.

Arylketone represents a moiety containing an aryl group linked to the main group or ring via a ketone.

Alkylaryl represents a moiety containing an alkyl linked to the main group or ring via an aryl group.

Heteroarylalkyl represents a moiety containing a heteroaryl group linked to the main group or ring via an alkyl.

The term "optionally substituted" means optional substitution with the specified groups, radicals or moieties.

The term "solvate" as used herein means an aggregate that consists of a solute ion or molecule with one or more solvent molecules, for example, a hydrate containing such ions.

As used herein, the terms "composition" and "formulation" are intended to encompass a product comprising the specified ingredients, as well as any product which results, directly or indirectly, from combination of the specified ingredients.

"Patient" includes mammals and other animals.

"Mammal" includes humans and other mammalian animals.

The term "therapeutically effective amount" is intended to mean an amount of a therapeutic agent of the compound of formula I that will have an effect on a tissue, system, animal or patient that is being sought by the administrator (such as a researcher, doctor or veterinarian), which includes alleviation of the symptoms of the condition or disease being treated and the prevention, slowing or halting of progression of the disease or condition, for example, the inflammatory, immunomodulatory or respiratory diseases discussed herein.

Prodrugs and solvates of the compounds of the invention are also contemplated within the scope of this invention. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

The compounds of formula I can form salts, solvates and prodrugs which are also within the scope of this invention. Reference to a compound of formula I herein is understood to include reference to salts, solvates and prodrugs thereof, unless otherwise indicated.

The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to, a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; and Anderson et al, *The Practice of Medicinal Chemistry* (1996), Academic Press, New York). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts and solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename from Glaxo-Wellcome Inc., Research Triangle, N.C. 27709; didanosine (ddI) available under the VIDEX tradename from Bristol-Myers Squibb Co., Princeton, N.J. 08543; zalcitabine (ddC) available under the HIVID tradename from Roche Pharmaceuticals, Nutley, N.J. 07110; stavudine (d4T) available under the ZERIT trademark from Bristol-Myers Squibb Co., Princeton, N.J. 08543; lamivudine (3TC) available under the EPIVIR tradename from Glaxo-Welcome Research Triangle, N.C. 27709; abacavir (1592U89) disclosed in WO96/30025 and available under the ZIAGEN trademark from Glaxo-Wellcome Research Triangle, N.C. 27709; adefovir dipivoxil [bis (POM)-PMEA] available under the PREVON tradename from Gilead Sciences, Foster City, Calif. 94404; lobucavir (BMS-180194), a nucleoside reverse transcriptase inhibitor disclosed in EP-0358154 and EP-0736533 and under development by Bristol-Myers Squibb, Princeton, N.J. 08543; BCH-10652, a reverse transcriptase inhibitor (in the form of a racemic mixture of BCH-10618 and BCH-10619) under development by Biochem Pharma, Laval, Quebec H7V, 4A7, Canada; emitricitabine [(−)-FTC] licensed from Emory University under Emory Univ. U.S. Pat. No. 5,814,639 and under development by Triangle Pharmaceuticals, Durham, N.C. 27707; beta-L-FD4 (also called beta-L-D4C and named beta-L-2',3'-dicleoxy-5-fluoro-cytidene) licensed by Yale University to Vion Pharmaceuticals, New Haven Conn. 06511; DAPD, the purine nucleoside, (−)-beta-D-2,6,-diamino-purine dioxolane disclosed in EP 0656778 and licensed by Emory University and the University of Georgia to Triangle Pharmaceuticals, Durham, N.C. 27707; and lodenosine (FddA), 9-(2,3-dideoxy-2-fluoro-b-D-threo-pentofuranosyl) adenine, an acid stable purine-based reverse transcriptase inhibitor discovered by the NIH and under development by U.S. Bioscience Inc., West Conshohoken, Pa. 19428.

The term "non-nucleoside reverse transcriptase inhibitors" ("NNRTI"s) as used herein means non-nucleosides that inhibit the activity of HIV-1 reverse transcriptase.

Typical suitable NNRTIs include nevirapine (BI-RG-587) available under the VIRAMUNE tradename from Boehringer Ingelheim, the manufacturer for Roxane Laboratories, Columbus, Ohio 43216; delaviradine (BHAP, U-90152) available under the RESCRIPTOR tradename from Pharmacia & Upjohn Co., Bridgewater N.J. 08807; efavirenz (DMP-266) a benzoxazin-2-one disclosed in WO94/03440 and available under the SUSTIVA tradename from DuPont Pharmaceutical Co., Wilmington, Del. 19880-0723; PNU-142721, a furopyridine-thio-pyrimide under development by Pharmacia and Upjohn, Bridgewater N.J. 08807; AG-1549 (formerly Shionogi #S-1153); 5-(3,5-dichlorophenyl)-thio-4-isopropyl-1-(4pyridyl)methyl -IH-imidazol-2-ylmethyl carbonate disclosed in WO 96/10019 and under clinical development by Agouron Pharmaceuticals, Inc., LaJolla Calif. 92037-1020; MKC-442 (1-(ethoxy-methyl)-5-(1-methylethyl)-6-(phenylmethyl)-(2,4(1H,3H)-pyrimidinedione) discovered by Mitsubishi Chemical Co. and under development by Triangle Pharmaceuticals, Durham, N.C. 27707; and (+)-calanolide A (NSC-675451) and B, coumarin derivatives disclosed in NIH U.S. Pat. No. 5,489,697, licensed to Med Chem Research, which is co-developing (+) calanolide A with Vita-invest as an orally administrable product.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN(available from Merck) as well as nonpeptide protease inhibitors e.g., VIRACEPT (available from Agouron).

Typical suitable P is include saquinavir (Ro 31-8959) available in hard gel capsules under the INVIRASE tradename and as soft gel capsules under the FORTOVASE tradename from Roche Pharmaceuticals, Nutley, N.J. 07110-1199; ritonavir (ABT-538) available under the NORVIR tradename from Abbott Laboratories, Abbott Park, Ill. 60064; indinavir (MK639) available under the CRIXIVAN tradename from Merck & Co., Inc., West Point, Pa. 19486-0004; nelfnavir (AG-1343) available under the VIRACEPT tradename from Agouron Pharmaceuticals, Inc., LaJolla Calif. 92037-1020; amprenavir (141W94), tradename AGENERASE, a non-peptide protease inhibitor under development by Vertex Pharmaceuticals, Inc., Cambridge, Mass. 02139-4211 and available from Glaxo-Wellcome, Research Triangle, N.C. under an expanded access program; lasinavir (BMS-234475) available from Bristol-Myers Squibb, Princeton, N.J. 08543 (originally discovered by Novartis, Basel, Switzerland (CGP-61755); DMP-450, a cyclic urea discovered by Dupont and under development by Triangle Pharmaceuticals; BMS-2322623, an azapeptide under development by Bristol-Myers Squibb, Princeton, N.J. 08543, as a 2nd-generation HIV-1 PI; ABT-378 under development by Abbott, Abbott Park, Ill. 60064; and AG-1549 an orally active imidazole carbamate discovered by Shionogi (Shionogi #S-1153) and under development by Agouron Pharmaceuticals, Inc., LaJolla Calif. 92037-1020.

Other antiviral agents include hydroxyurea, ribavirin, IL-2, IL-12, pentafuside and Yissum Project No. 11607. Hydroyurea (Droxia), a ribonucleoside triphosphate reductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN (aldesleukin) tradename from Chiron Corp., Emeryville, Calif. 94608-2997 as a lyophilized powder for IV infusion or sc administration upon reconstitution and dilution with water; a dose of about 1 to about 20 million IU/day, sc is preferred; a dose of about 15 million IU/day, sc is more preferred. IL-12 is disclosed in WO96/25171 and is available from Roche Pharmaceuticals, Nutley, N.J. 07110-1199 and American Home Prodocts, Madison, N.J. 07940; a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 licensed from Duke University to Trimeris which is developing pentafuside in collaboration with Duke University; pentafuside acts by inhibiting fusion of HIV-1 to target membranes. Pentafuside (3-100 mg /day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein, is under preclinical development by Yissum Research Development Co., Jerusalem 91042, Israel. Ribavirin, 1-β-D-ribofuranosyl-1H-1,2,4-triazole-3-carboxamide, is available from ICN Pharmaceuticals, Inc., Costa Mesa, Calif.; its manufacture and formulation are described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include:

(a) triple combination therapies such as two NRTIs and one PI; or (b) two NRTIs and one NNRTI; and (c) quadruple combination therapies such as two NRTIs , one PI and a second PI or one NNRTI. In treatment of naive patients, it is preferred to start anti-HIV-1 treatment with the triple combination therapy; the use of two NRTIs and one PI is prefered unless there is intolerance to PIs. Drug compliance is essential. The CD4+ and HIV-1-RNA plasma levels should be monitored every 3-6 months. Should viral load plateau, a fourth drug, e.g., one PI or one NNRTI could be added. See the table below wherein typical therapies are further described:

Anti-HIV-1 Multi Drug Combination Therapies

A. Triple Combination Therapies
1. Two NRTIs[1]+one PI[2]
2. Two NRTIs[1]+one NNRTI[3]

B. Quadruple Combination Therapies[4]
    Two NRTIs+one PI+a second PI or one NNRTI C. Alternatives:[5]
    Two NRTI[1]
    One NRTI[5]+one PI[2]
    Two PIs[6]+one NRTI[7] or NNRTI[3]
    One PI[2]+one NRTI+one NNRTI[3]

Footnotes To Table
1. One of the following: zidovudine+lamivudine; zidovudine+didanosine; stavudine+lamivudine; stavudine+didanosine; zidovudine+zalcitabine
2. Indinavir, nelfinavir, ritonavir or saquinavir soft gel capsules.
3. Nevirapine or delavirdine.
4. See A-M. Vandamne et al Antiviral Chemistry & Chemotherapy 9:187 at p. 193-197 and FIGS. 1+2.
5. Alternative regimens are for patients unable to take a recommended regimen because of compliance problems or toxicity, and for those who fail or relapse on a recommended regimen. Double nucleoside combinations may lead to HIV-resistance and clinical failure in many patients.
6. Most data obtained with saquinavir and ritonavir (each 400 mg bid).
7. Zidovudine, stavudine or didanosine.

A preferred embodiment includes compounds wherein $R^9$, $R^{10}$ and B are H, and A is —$CH_3$.

Another preferred embodment includes, but are not limited to, compounds wherein $R^1$, $R^2$ and $R^3$ are as defined in the following table:

TABLE 1

| # | $R^1$ | $R^2$ | $R^3$ |
|---|---|---|---|
| 1 | 3-chlorophenylsulfonyl-piperidin-4-yl | benzyl | 4,6-dimethylpyrimidin-5-yl |
| 2 | methylsulfonyl-piperidin-4-yl | benzyl | 4,6-dimethylpyrimidin-5-yl |
| 3 | 3-chlorophenylsulfonyl-piperidin-4-yl | cyclopropylmethyl | 4,6-dimethylpyrimidin-5-yl |
| 4 | 1-benzyl-piperidin-4-yl | benzyl | 4,6-dimethylpyrimidin-5-yl |

TABLE 1-continued
| # | R¹ | R² | R³ |
|---|---|---|---|
| 5 | 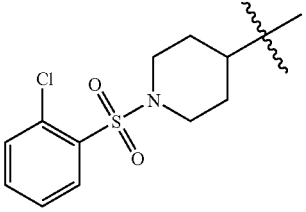 | 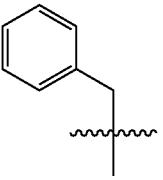 | 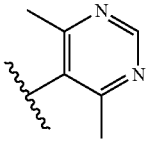 |
| 6 | 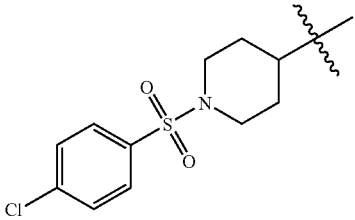 | 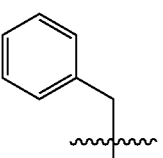 | 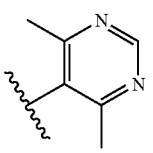 |
| 7 | 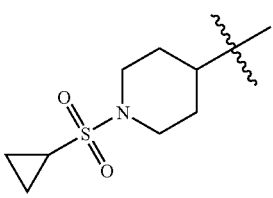 | 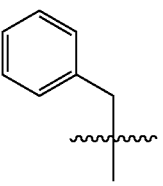 | 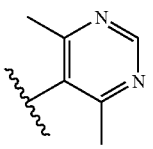 |
| 8 | 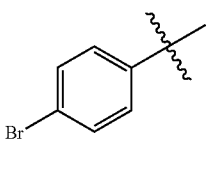 | 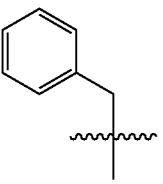 | 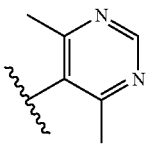 |
| 9 | 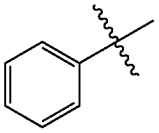 | 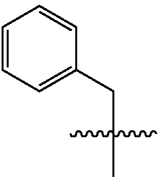 | 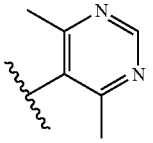 |
| 10 | 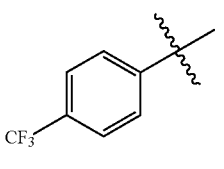 | 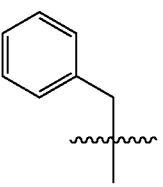 | 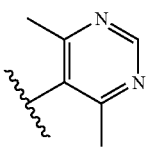 |
| 11 | 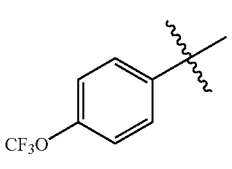 | 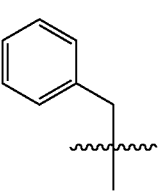 | 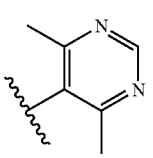 |

TABLE 1-continued
| # | R¹ | R² | R³ |
|---|----|----|----|
| 12 | 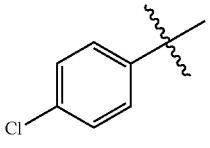 | 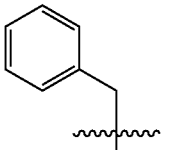 | 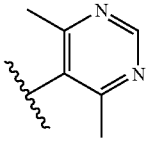 |
| 13 | 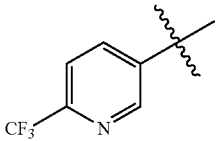 | 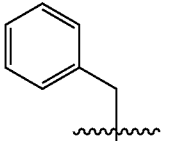 | 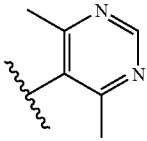 |
| 14 | 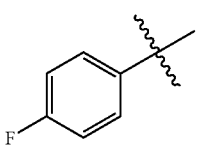 | 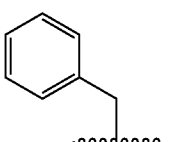 | 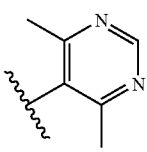 |
| 15 | 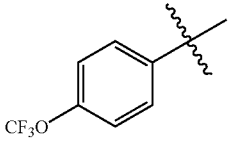 | 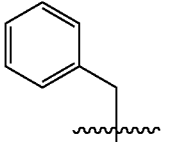 | 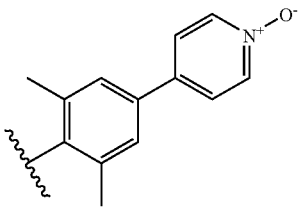 |
| 16 | 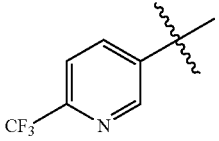 | 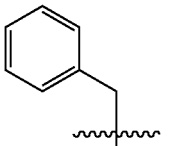 | 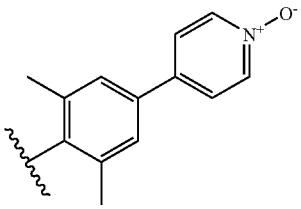 |
| 17 | 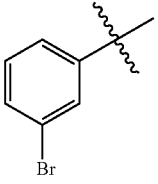 | 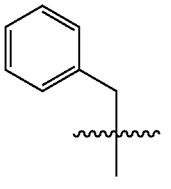 | 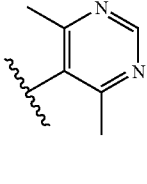 |
| 18 | 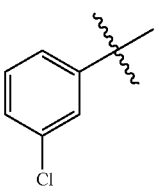 | 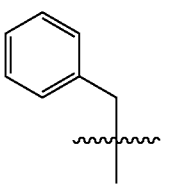 | 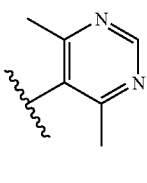 |

TABLE 1-continued

| # | R¹ | R² | R³ |
|---|---|---|---|
| 19 | 3-Br-phenyl | 4-F-benzyl | 4,6-dimethylpyrimidin-5-yl |
| 20 | 3-CF₃-phenyl | benzyl | 4,6-dimethylpyrimidin-5-yl |
| 21 | 4-tert-butyl-phenyl | benzyl | 4,6-dimethylpyrimidin-5-yl |
| 22 | 4-isopropyl-phenyl | benzyl | 4,6-dimethylpyrimidin-5-yl |
| 23 | 4-I-phenyl | benzyl | 4,6-dimethylpyrimidin-5-yl |
| 24 | 3-OCF₃-phenyl | benzyl | 4,6-dimethylpyrimidin-5-yl |
| 25 | 3,4-difluoro-phenyl | benzyl | 4,6-dimethylpyrimidin-5-yl |
| 26 | 3,4-dichloro-phenyl | benzyl | 4,6-dimethylpyrimidin-5-yl |

TABLE 1-continued
| # | R¹ | R² | R³ |
|---|---|---|---|
| 27 | 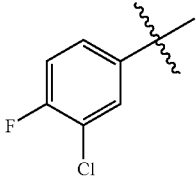 | 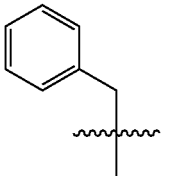 | 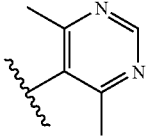 |
| 28 | 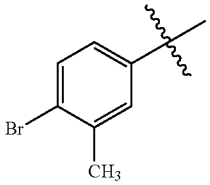 | 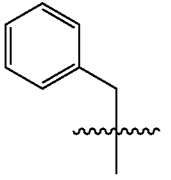 | 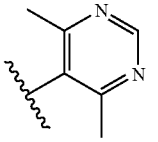 |
| 29 | 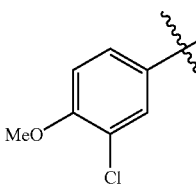 | 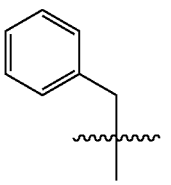 | 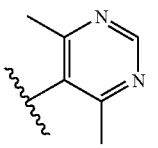 |
| 30 | 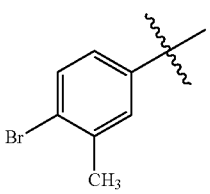 | 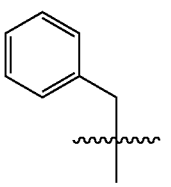 | 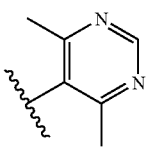 |
| 31 | 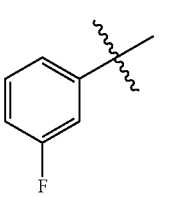 | 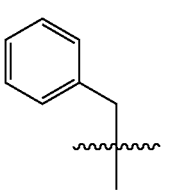 | 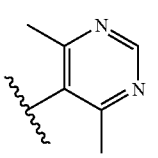 |
| 32 | 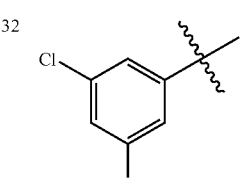 | 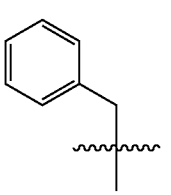 | 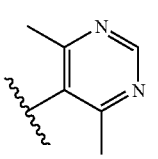 |
| 33 | 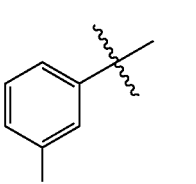 | 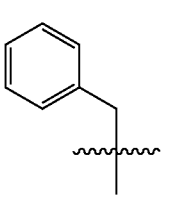 | 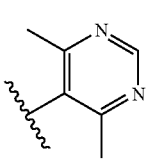 |
| 34 | 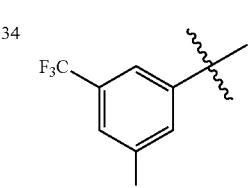 | 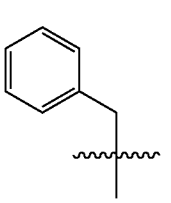 | 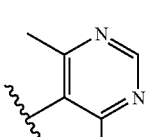 |

TABLE 1-continued
| # | R¹ | R² | R³ |
|---|---|---|---|
| 35 | 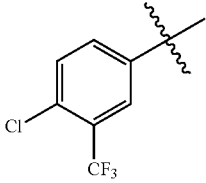 | 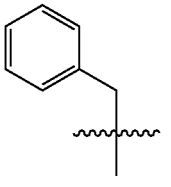 | 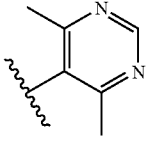 |
| 36 | 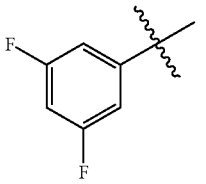 | 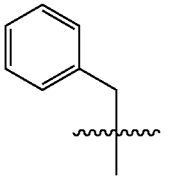 | 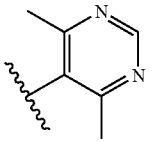 |
| 37 | 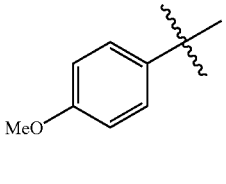 | 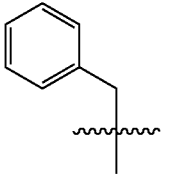 | 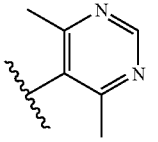 |
| 38 | 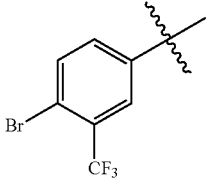 | 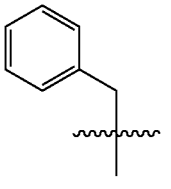 | 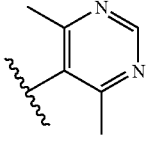 |
| 39 | 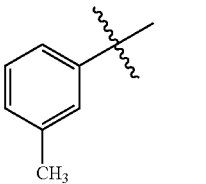 | 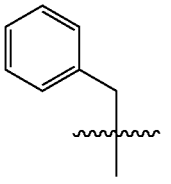 | 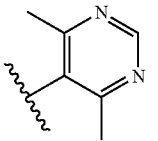 |
| 40 | 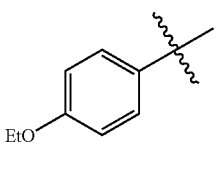 | 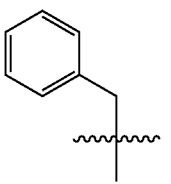 | 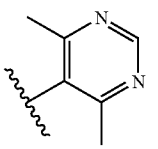 |
| 41 | 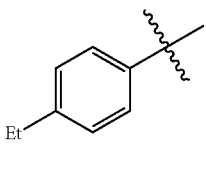 | 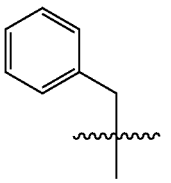 | 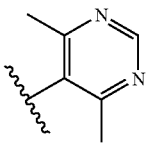 |
| 42 | 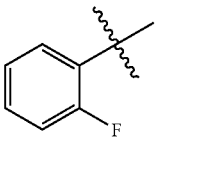 | 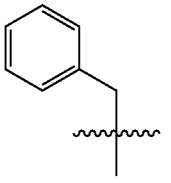 | 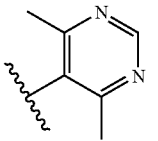 |

TABLE 1-continued

| # | R¹ | R² | R³ |
|---|---|---|---|
| 43 | 4-PhO-C₆H₄- | benzyl | 4,6-dimethylpyrimidin-5-yl |
| 44 | 3-CN-C₆H₄- | benzyl | 4,6-dimethylpyrimidin-5-yl |
| 45 | 4-(morpholin-4-yl)-C₆H₄- | benzyl | 4,6-dimethylpyrimidin-5-yl |
| 46 | 1-Bn-pyrazol-3-yl | benzyl | 4,6-dimethylpyrimidin-5-yl |
| 47 | 4-(MeSO₂NH-CH₂CH₂)-C₆H₄- | benzyl | 4,6-dimethylpyrimidin-5-yl |
| 48 | 4-(MeSO₂N(Bn)-CH₂CH₂)-C₆H₄- | benzyl | 4,6-dimethylpyrimidin-5-yl |
| 49 | 4-(AcNH-CH₂CH₂)-C₆H₄- | benzyl | 4,6-dimethylpyrimidin-5-yl |
| 50 | 4-MeSO₂-C₆H₄- | benzyl | 4,6-dimethylpyrimidin-5-yl |

TABLE 1-continued

| # | R¹ | R² | R³ |
|---|---|---|---|
| 51 | 5-chloroquinolin-8-yl | benzyl | 4,6-dimethylpyrimidin-5-yl |
| 52 | 5-bromoquinolin-8-yl | benzyl | 4,6-dimethylpyrimidin-5-yl |
| 53 | quinolin-8-yl | benzyl | 4,6-dimethylpyrimidin-5-yl |
| 54 | 4-(allyloxycarbonylaminoethyl)phenyl | benzyl | 4,6-dimethylpyrimidin-5-yl |
| 55 | 4-(2-aminoethyl)phenyl | benzyl | 4,6-dimethylpyrimidin-5-yl |
| 56 | 4-(cyclopropylsulfonylaminoethyl)phenyl | benzyl | 4,6-dimethylpyrimidin-5-yl |
| 57 | 4-(2,2,2-trifluoroethylsulfonylaminoethyl)phenyl | benzyl | 4,6-dimethylpyrimidin-5-yl |
| 58 | 4-(allyloxycarbonyl)phenyl | benzyl | 4,6-dimethylpyrimidin-5-yl |

TABLE 1-continued

| # | R¹ | R² | R³ |
|---|---|---|---|
| 59 | 3-(HO₂C)-phenyl- | benzyl | 4,6-dimethylpyrimidin-5-yl |
| 60 | 4-(HO₂C)-phenyl- | benzyl | 4,6-dimethylpyrimidin-5-yl |
| 61 | 3-(H₂NC(O))-phenyl- | benzyl | 4,6-dimethylpyrimidin-5-yl |
| 62 | 3-(morpholin-4-ylcarbonyl)-phenyl- | benzyl | 4,6-dimethylpyrimidin-5-yl |
| 63 | 3-(N,N-diethylaminocarbonyl)-phenyl- | benzyl | 4,6-dimethylpyrimidin-5-yl |
| 64 | 3-(HO-NH-C(O))-phenyl- | benzyl | 4,6-dimethylpyrimidin-5-yl |
| 65 | 3-(PhNHC(O))-phenyl- | benzyl | 4,6-dimethylpyrimidin-5-yl |
| 66 | 3-(PhCH₂NHC(O))-phenyl- | benzyl | 4,6-dimethylpyrimidin-5-yl |

TABLE 1-continued

| # | R¹ | R² | R³ |
|---|---|---|---|
| 67 | HO-CH₂CH₂-NH-C(O)-[3-phenyl] | benzyl | 4,6-dimethylpyrimidin-5-yl |
| 68 | cyclopropyl-NH-C(O)-[3-phenyl] | benzyl | 4,6-dimethylpyrimidin-5-yl |
| 69 | 6-(trifluoromethyl)pyridin-3-yl | benzyl | 4,6-dimethylpyrimidin-5-yl |
| 70 | 4-(trifluoromethoxy)phenyl | benzyl | 4,6-dimethylpyrimidin-5-yl |
| 71 | 5-bromopyridin-2-yl | benzyl | 4,6-dimethylpyrimidin-5-yl |
| 72 | phenyl | benzyl | 4,6-dimethylpyrimidin-5-yl |
| 73 | 4-chlorophenyl | benzyl | 4,6-dimethylpyrimidin-5-yl |
| 74 | phenyl | cyclopropylmethyl | 4,6-dimethylpyrimidin-5-yl |

TABLE 1-continued

| # | R¹ | R² | R³ |
|---|---|---|---|
| 75 | phenyl | phenyl-(CH₂)₂- | 4,6-dimethylpyrimidin-5-yl |
| 76 | 5-(trifluoromethyl)pyridin-2-yl | phenyl | 4,6-dimethylpyrimidin-5-yl |
| 77 | pyridin-2-yl | phenyl | 4,6-dimethylpyrimidin-5-yl |
| 78 | 5-chloropyridin-2-yl | phenyl | 4,6-dimethylpyrimidin-5-yl |
| 79 | 4-fluorophenyl | phenyl | 4,6-dimethylpyrimidin-5-yl |
| 80 | phenyl | pyridin-3-ylmethyl | 4,6-dimethylpyrimidin-5-yl |
| 81 | 4-(trifluoromethoxy)phenyl | phenyl | 4-(1-oxidopyridin-4-yl)-2,6-dimethylphenyl |

TABLE 1-continued

| # | R¹ | R² | R³ |
|---|---|---|---|
| 82 | 2-CF₃-pyridin-5-yl | phenyl | 3,5-dimethyl-4-(pyridin-4-yl N-oxide)phenyl |
| 83 | 5-CF₃-pyridin-2-yl | pyridin-4-yl | 3,5-dimethyl-4-(pyridin-4-yl N-oxide)phenyl |
| 84 | phenyl | pyridin-2-ylmethyl | 3,5-dimethyl-4-(pyridin-4-yl N-oxide)phenyl |
| 85 | 4-bromophenyl | 2-methoxyethyl | 3,5-dimethyl-4-(pyridin-4-yl N-oxide)phenyl |
| 86 | phenyl | pyridin-4-ylmethyl | 4,6-dimethylpyrimidin-5-yl |
| 87 | 3-bromophenyl | phenyl | 4,6-dimethylpyrimidin-5-yl |
| 88 | 4-bromophenyl | pyridin-4-ylmethyl | 4,6-dimethylpyrimidin-5-yl |

TABLE 1-continued
| # | R¹ | R² | R³ |
|---|----|----|----|
| 89 | 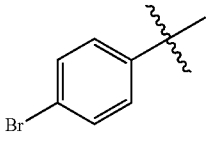 | 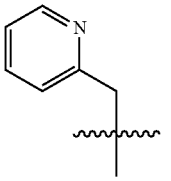 | 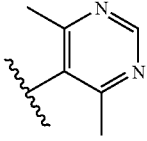 |
| 90 | 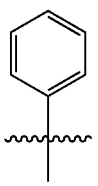 | 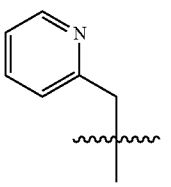 | 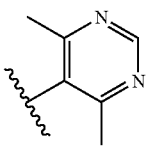 |
| 91 | 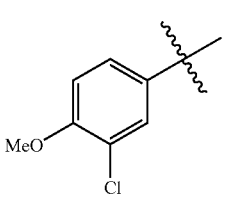 | 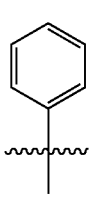 | 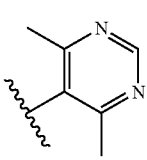 |
| 92 | 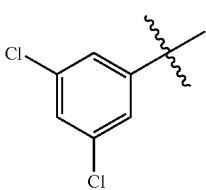 | 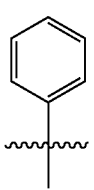 | 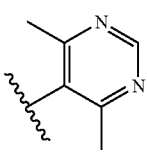 |
| 93 | 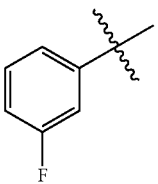 | 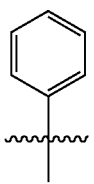 | 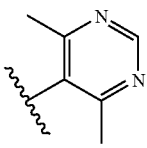 |
| 94 | 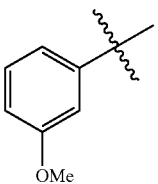 | 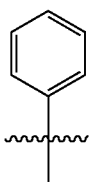 | 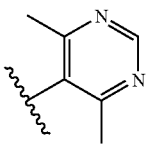 |
| 95 | 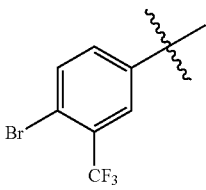 | 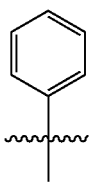 | 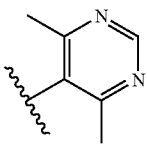 |
| 96 | 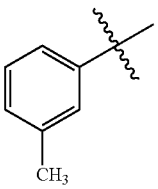 | 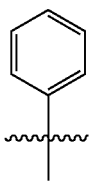 | 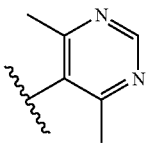 |

TABLE 1-continued
| # | R¹ | R² | R³ |
|---|----|----|----|
| 97 | 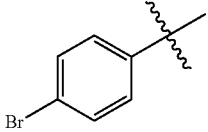 | 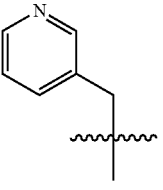 | 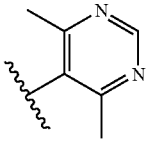 |
| 98 | 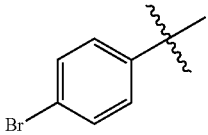 | 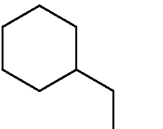 | 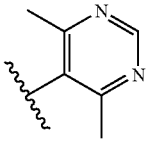 |
| 99 | 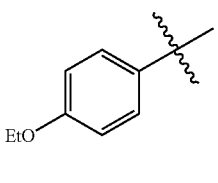 | 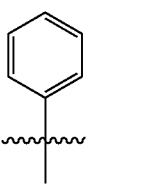 | 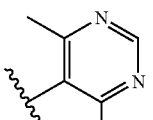 |
| 100 | 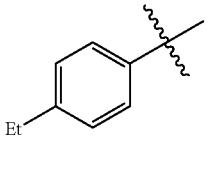 | 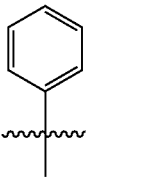 | 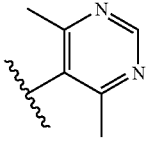 |
| 101 | 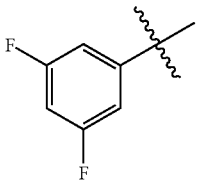 | 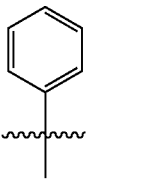 | 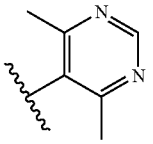 |
| 102 | 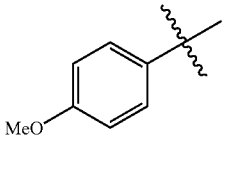 | 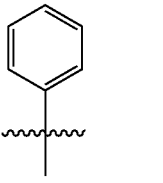 | 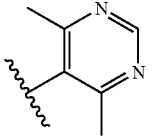 |
| 103 | 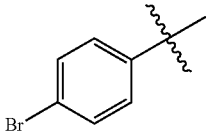 | 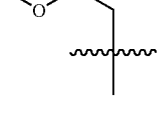 | 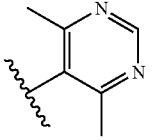 |
| 104 | 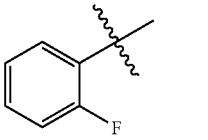 | 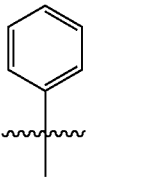 | 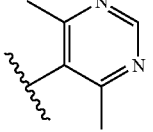 |

TABLE 1-continued
| # | R¹ | R² | R³ |
|---|----|----|----|
| 105 | 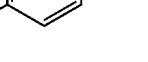 |  |  |
| 106 |  | 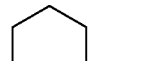 | 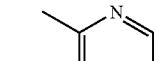 |
| 107 |  |  |  |
| 108 |  |  | 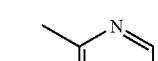 |
| 109 | 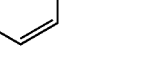 |  |  |
| 110 |  |  | 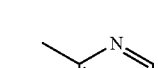 |
| 111 | 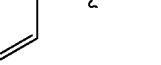 | CH₃ | 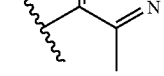 |

TABLE 1-continued

| # | R¹ | R² | R³ |
|---|---|---|---|
| 112 | 3-piperidinyl, N-sulfonyl-cyclopropyl | benzyl | 4,6-dimethylpyrimidin-5-yl |
| 113 | 3-piperidinyl, N-methylsulfonyl | benzyl | 4,6-dimethylpyrimidin-5-yl |

Preferred compounds from TABLE I above are shown below in TABLE IA:

TABLE IA

| # | R¹ | R² | R³ |
|---|---|---|---|
| 1 | 4-piperidinyl, N-(3-chlorophenylsulfonyl) | benzyl | 4,6-dimethylpyrimidin-5-yl |
| 2 | 4-piperidinyl, N-methylsulfonyl | benzyl | 4,6-dimethylpyrimidin-5-yl |
| 6 | 4-piperidinyl, N-(4-chlorophenylsulfonyl) | benzyl | 4,6-dimethylpyrimidin-5-yl |
| 10 | 4-(trifluoromethyl)phenyl (gem-dimethyl) | benzyl | 4,6-dimethylpyrimidin-5-yl |

TABLE IA-continued

| # | R¹ | R² | R³ |
|---|---|---|---|
| 11 | 4-(CF₃O)-phenyl | benzyl | 4,6-dimethylpyrimidin-5-yl |
| 12 | 4-Cl-phenyl | benzyl | 4,6-dimethylpyrimidin-5-yl |
| 13 | 6-(CF₃)-pyridin-3-yl | benzyl | 4,6-dimethylpyrimidin-5-yl |
| 14 | 4-F-phenyl | benzyl | 4,6-dimethylpyrimidin-5-yl |
| 16 | 6-(CF₃)-pyridin-3-yl | benzyl | 4-(1-oxidopyridin-4-yl)-3,5-dimethylphenyl |
| 17 | 3-Br-phenyl | benzyl | 4,6-dimethylpyrimidin-5-yl |
| 28 | 4-Br-3-methyl-phenyl | benzyl | 4,6-dimethylpyrimidin-5-yl |
| 29 | 4-MeO-3-Cl-phenyl | benzyl | 4,6-dimethylpyrimidin-5-yl |

TABLE IA-continued

| # | R¹ | R² | R³ |
|---|----|----|----|
| 31 | 3-fluorophenyl | benzyl (CH₂-phenyl) | 4,6-dimethylpyrimidin-5-yl |
| 36 | 3,5-difluorophenyl | benzyl | 4,6-dimethylpyrimidin-5-yl |
| 37 | 4-methoxyphenyl | benzyl | 4,6-dimethylpyrimidin-5-yl |
| 39 | 3-methylphenyl | benzyl | 4,6-dimethylpyrimidin-5-yl |
| 40 | 4-ethoxyphenyl | benzyl | 4,6-dimethylpyrimidin-5-yl |
| 47 | 4-(2-(methylsulfonylamino)ethyl)phenyl | benzyl | 4,6-dimethylpyrimidin-5-yl |
| 49 | 4-(2-(acetylamino)ethyl)phenyl | benzyl | 4,6-dimethylpyrimidin-5-yl |
| 50 | 4-(methylsulfonyl)phenyl | benzyl | 4,6-dimethylpyrimidin-5-yl |

TABLE IA-continued

| # | R¹ | R² | R³ |
|---|----|----|-----|
| 56 | cyclopropyl-S(O)₂-NH-CH₂CH₂-(4-phenyl)- | benzyl | 4,6-dimethylpyrimidin-5-yl |
| 57 | CF₃CH₂-S(O)₂-NH-CH₂CH₂-(4-phenyl)- | benzyl | 4,6-dimethylpyrimidin-5-yl |
| 61 | 3-(H₂N-C(O))-phenyl- | benzyl | 4,6-dimethylpyrimidin-5-yl |
| 68 | 3-(cyclopropyl-NH-C(O))-phenyl- | benzyl | 4,6-dimethylpyrimidin-5-yl |
| 69 | 6-(CF₃)-pyridin-3-yl- | benzyl | 4,6-dimethylpyrimidin-5-yl |
| 70 | 4-(F₃CO)-phenyl- | benzyl | 4,6-dimethylpyrimidin-5-yl |
| 71 | 5-Br-pyridin-2-yl- | benzyl | 4,6-dimethylpyrimidin-5-yl |
| 80 | phenyl- | pyridin-3-ylmethyl | 4,6-dimethylpyrimidin-5-yl |

TABLE IA-continued
| # | R¹ | R² | R³ |
|---|----|----|----|
| 81 | 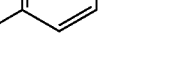 |  | 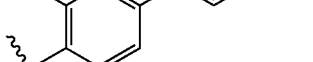 |
| 82 | 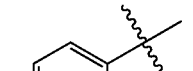 |  | 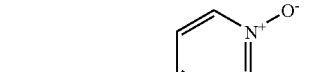 |
| 90 |  | 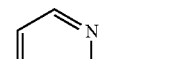 | 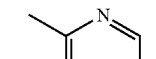 |
| 91 | 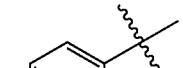 |  | 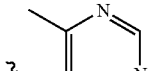 |
| 93 |  |  | 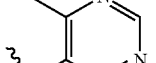 |
| 96 |  |  | 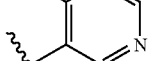 |
| 99 | 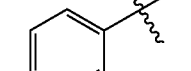 |  | 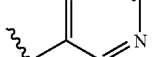 |

TABLE IA-continued
| # | R¹ | R² | R³ |
|---|---|---|---|
| 100 | 4-Et-C₆H₄-CH(CH₃)- | phenyl | 4,6-dimethylpyrimidin-5-yl |
| 101 | 3,5-difluorophenyl-CH(CH₃)- | phenyl | 4,6-dimethylpyrimidin-5-yl |
| 102 | 4-MeO-C₆H₄-CH(CH₃)- | phenyl | 4,6-dimethylpyrimidin-5-yl |
Even more preferably, the compounds of the present invention are represented by the following formulae:
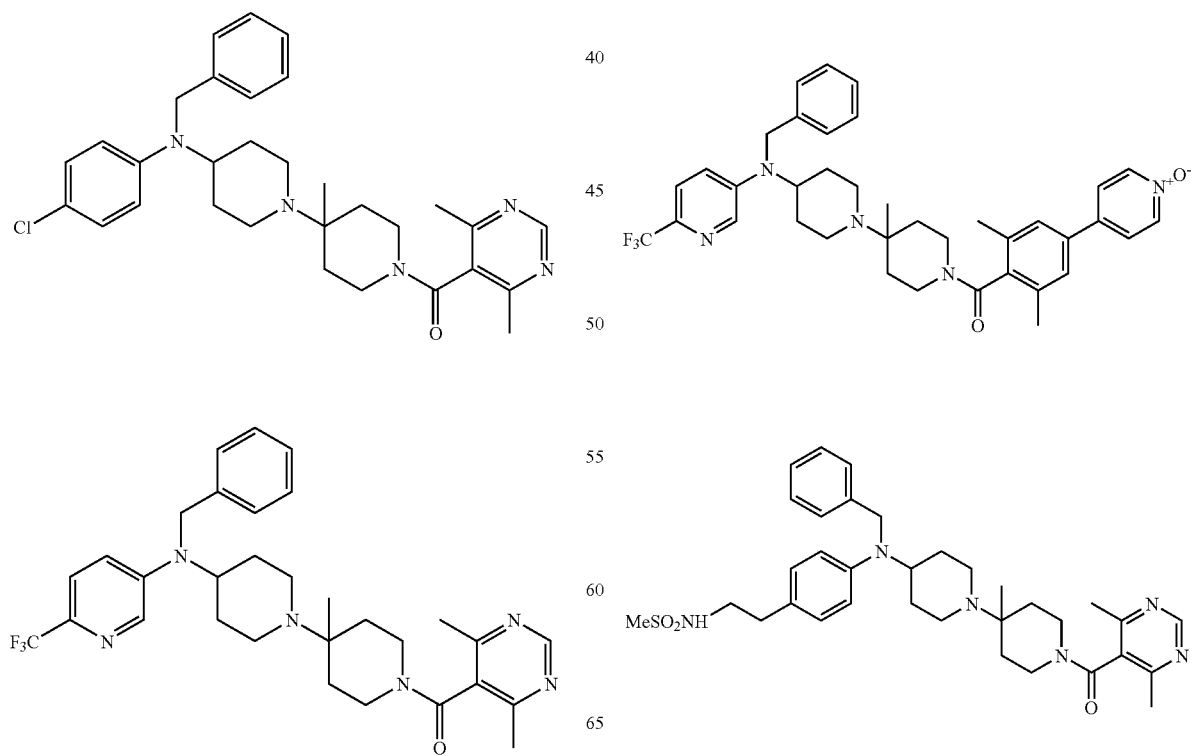

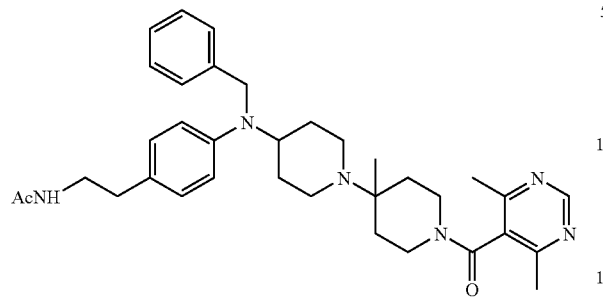

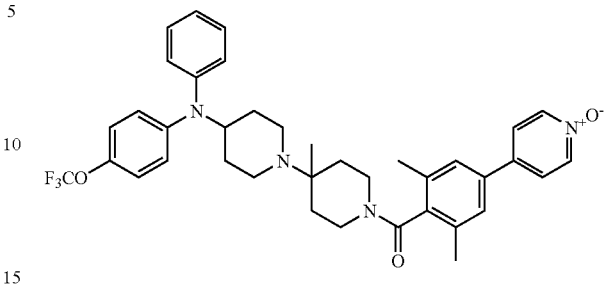

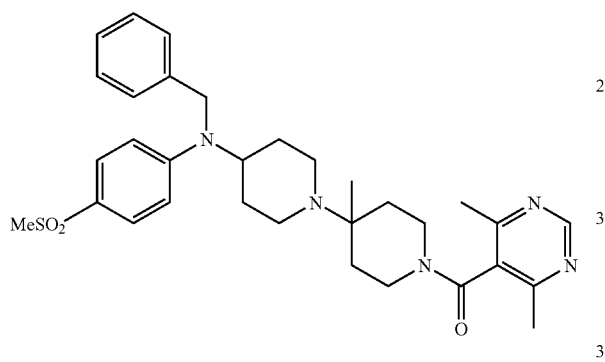

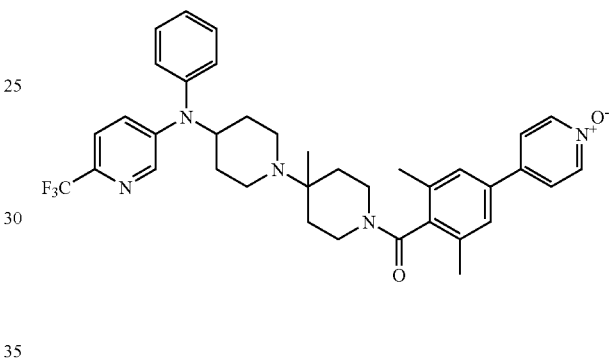

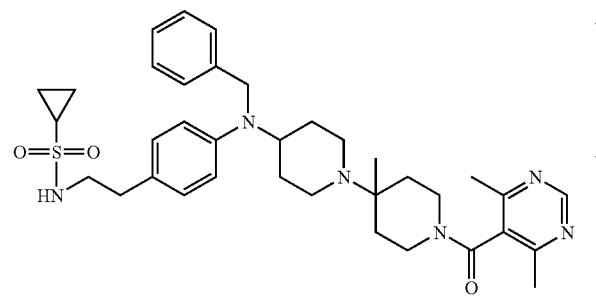

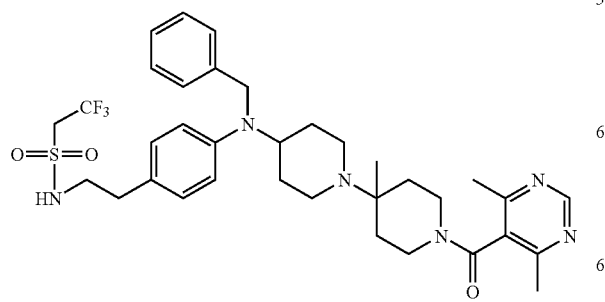

The compound of the present invention, also referred to herein as the inventive compound, is particularly useful as a CCR5 antagonist.

Compounds of the invention can be made by the procedures known in the art, for example by the procedures described in the following reaction schemes, by the methods described in the examples below, and by using the methods described in U.S. Pat. Nos. 5,883,096; 6,037,352; 5,889,006; 5,952,349; and 5,977,138.

The following solvents and reagents may be referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxy-benzotriazole (HOBT); m-chloroperbenzoic acid (MCPBA); triethylamine (Et$_3$N); diethyl ether (Et$_2$O); tert-butoxycarbonyl (BOC); 1,8-diazabicyclo[5.4.0]undec-7-ene (DBU); dimethylsulfoxide (DMSO); p-toluene sulfonic acid (p-TSA); potassium bis(trimethylsilyl)-amide (KHMDA); 4-dimethylaminopryidine (DMAP); N,N,N-diiosopropylethylamine (DIPEA); and 1-(3-dimethyl-aminopropyl)-3-ethyl carbodiimide hydrochloride (EDCI). RT is room temperature.

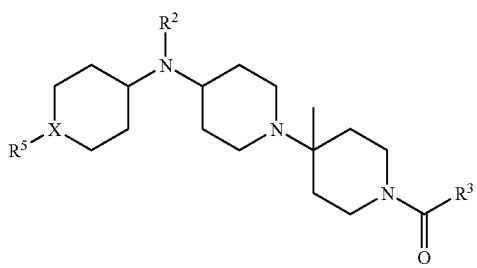

Compounds of formula IA wherein X is CH$_2$ or N, R$^2$ is alkyl, aryl, or benzyl, and R$^3$ and R$^5$ is as defined in the summary of the invention are prepared according to Scheme A.

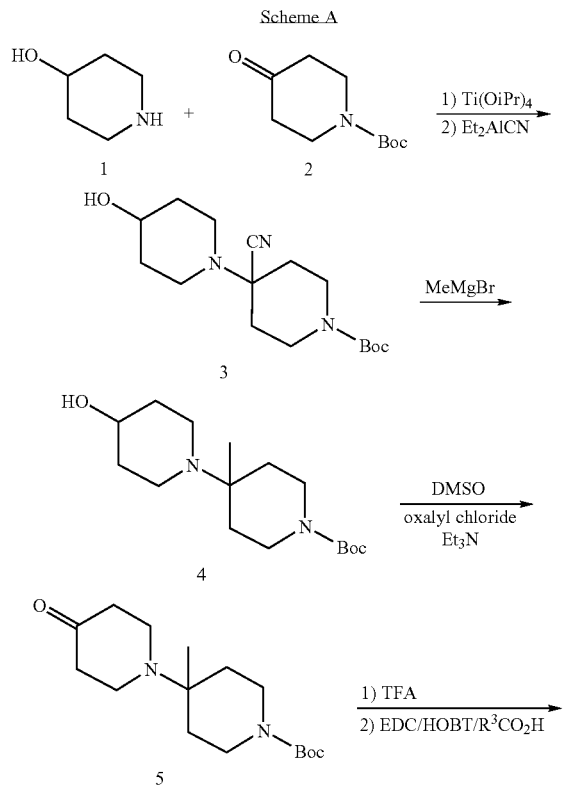

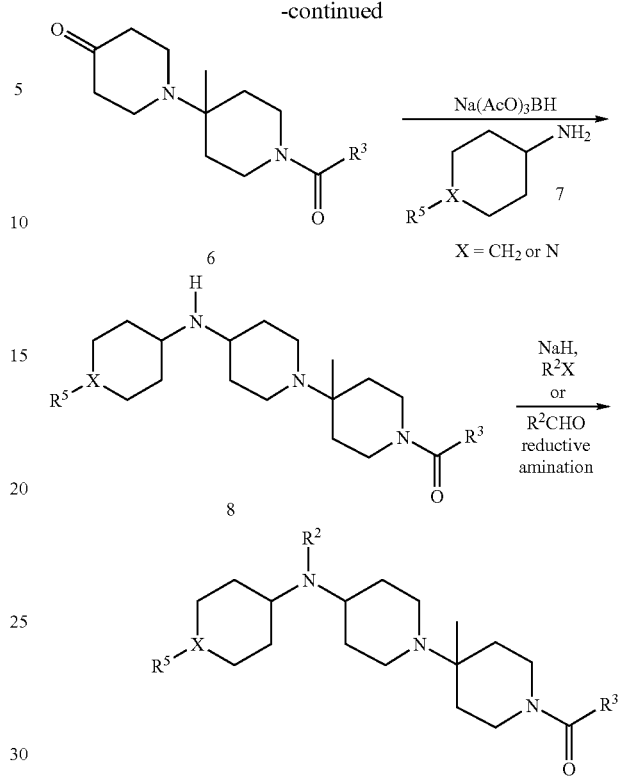

For the synthesis of compounds of formula IA, 4-hydroxy-piperidine 1 and N-Boc-4-piperidone 2 are sequentially treated with titanium isopropoxide and diethyl aluminum cyanide to furnish the cyano-amine 3. The cyano-amine 3 is treated with methyl magnesium bromide to furnish the methylated derivative 4. The piperidinol 4 is oxidized to the ketone 5 by swern oxididation. The Boc group in 5 is removed by treatment with an acid such as TFA, and the free amine is coupled with acid such as R$_3$CO$_2$H using standard conditions to furnish the keto-amide 6. The keto-amide 8 is reacted with a substituted 4-amino piperidine 7 in the presence of sodium triacetoxy borohydride to give the amine 8. The free amine in 8 can be functionalized either by reductive amination (RCHO/Na(AcO)$_3$BH) or alkylation (NaH or Cs$_2$CO$_3$/R$^2$X) to furnish compounds of formula IA.

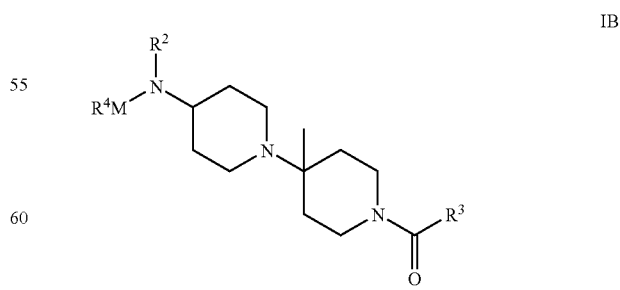

Compounds of formula IIA where R$^2$, R$^3$, R$^4$, and M are as defined are prepared according to Schemes B, C and D as follows.

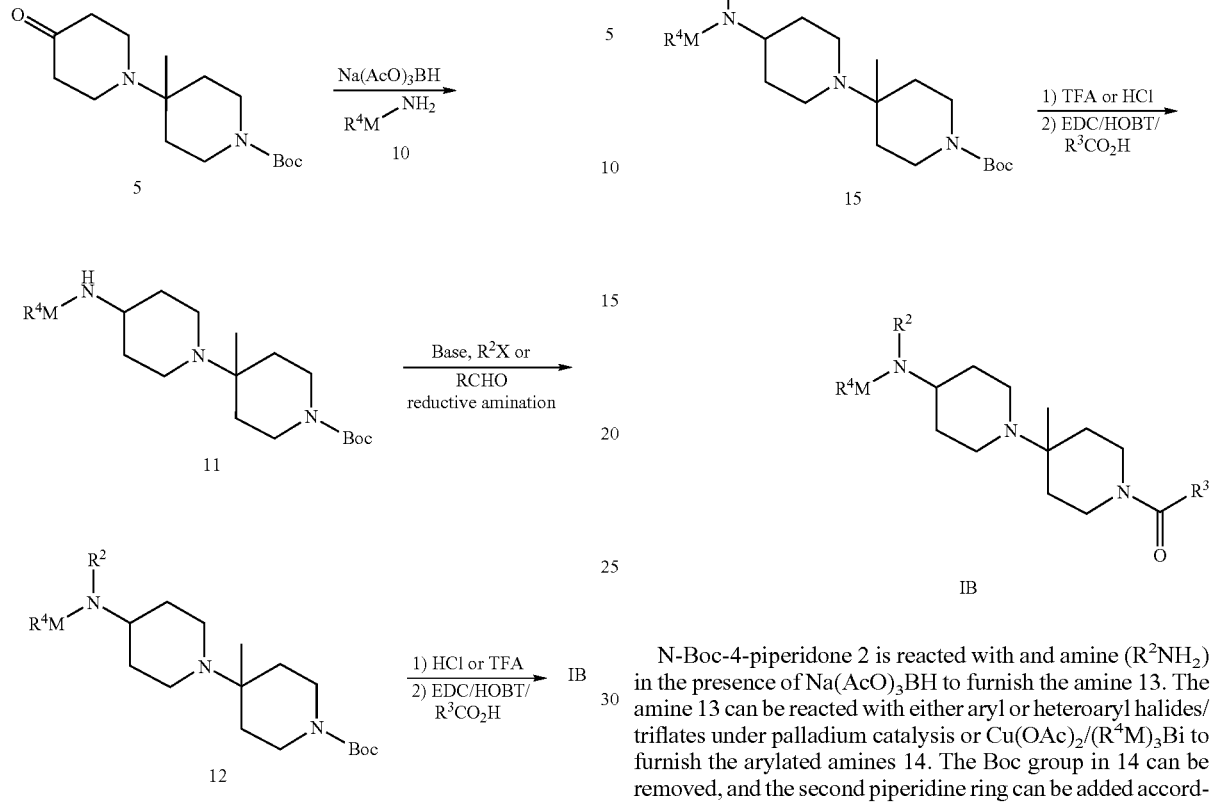

The keto-amide 5 is reacted with an amine 10 in the presence of sodium triacetoxyborohydride to furnish the functionalized amine 11. The amine 11 can be alkylated either with NaH, $Cs_2CO_3/R^2X$ or $Na(AcO)_3BH/RCHO$ to furnish the tertiary amine 12. The Boc group in 12 can be removed with an acid such as HCl or TFA, and the resulting piperidine can be coupled to acids to furnish compounds of formula IB.

N-Boc-4-piperidone 2 is reacted with and amine ($R^2NH_2$) in the presence of $Na(AcO)_3BH$ to furnish the amine 13. The amine 13 can be reacted with either aryl or heteroaryl halides/triflates under palladium catalysis or $Cu(OAc)_2/(R^4M)_3Bi$ to furnish the arylated amines 14. The Boc group in 14 can be removed, and the second piperidine ring can be added according to the procedure previously discussed (Scheme 1; Steps 1 and 2) to furnish the piperidine 15. The Boc group in 15 is removed with an acid such as TFA or HCL, and the amine is coupled to an acid represented by $R_3CO_2H$ to furnish the compounds of formula IB.

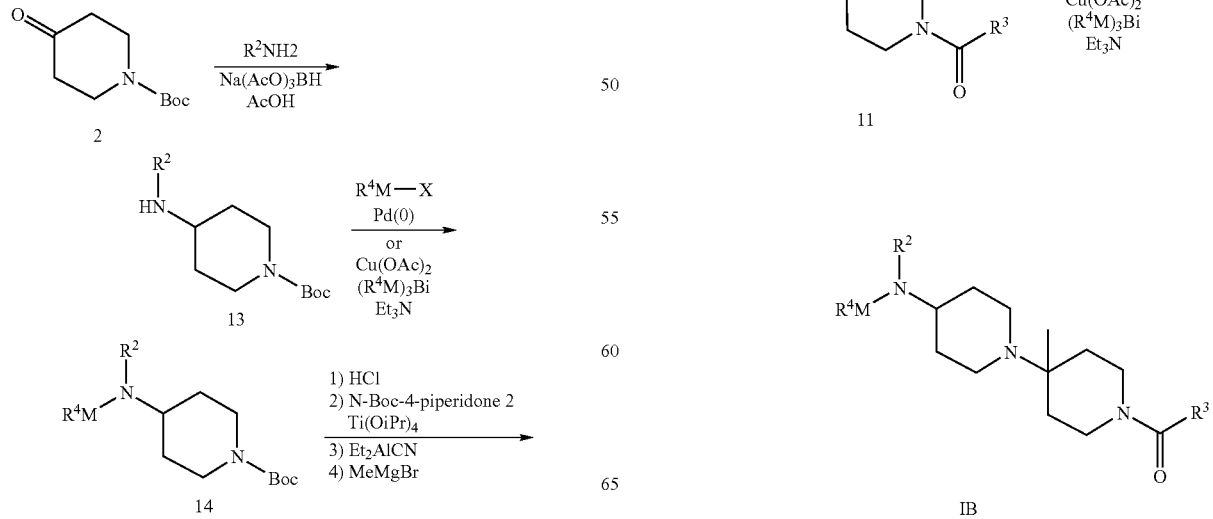

The functionalized amine 11 can be reacted according to procedures outlined above in Scheme C to furnish compounds of formula IB.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. An example of this includes, but is not limited to, water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compound of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be deliverable subcutaneously.

Preferably the compound is administered orally.

Preferably, the pharmaceutical preparation is in a unit dosage form. In such form, the preparation is subdivided into suitably sized unit doses containing a therapeutically effective amount of the compound having formula I.

The quantity of active compound in a unit dose of preparation may be varied or adjusted from about 10 mg to about 500 mg, preferably from about 25 mg to about 300 mg, more preferably from about 50 mg to about 250 mg, and most preferably from about 55 mg to about 200 mg, according to the particular application.

The actual dosage of the inventive compound employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 100 mg/day to about 300 mg/day, preferably 150 mg/day to 250 mg/day, more preferably about 200 mg/day, in two to four divided doses.

The doses and dosage regimens of the NRTIs, NNRTIs, P is and other agents used in combination with the compounds of this invention will be determined by the attending clinician inview of the approved doses and dosage regimens in the package inserts or as set forth in the protocols, taking into consideration the age, sex and condition of the patient and the severity of the condition treated.

In a preferred embodiment, the compound of the present invention can be used to treat Human Immunodeficiency Virus by administering to a patient in need of such treatment a therapeutically effective amount of one or more compounds having formula I, preferably in combination with one or more pharmaceutically acceptable carriers. One or more, preferably one to four, antiviral agents useful in anti-HIV-1 therapy can be used in combination with the compound of the present invention. The antiviral agent or agents can be combined with one or more compounds of the present invention in a single dosage form, or the one or more compounds of the present invention and the antiviral agent or agents may be administered simultaneously or sequentially as separate dosage forms.

The antiviral agents contemplated for use in combination with the compound of the present invention comprise nucleoside and nucleotide reverse transcriptase inhibitors, non-nucleoside reverse transcriptase inhibitors, protease inhibitors and other antiviral drugs listed below not falling within these classifications. Specific examples of antiviral agents include, but are not limited to, zidovudine, lamivudine, zalcitabine, didanosine, stavudine, abacavir, adefovir dipivoxil, lobucavir, BCH-10652, emitricitabine, beta-L-FD4, DAPD, lodenosine, nevirapine, delaviridine, efavirenz, PNU-142721, AG-1549, MKC-442, (+)-calanolide A and B, saquinavir, indinavir, ritonavir, nelfinavir, lasinavir, DMP-450, BMS-2322623, ABT-378, amprenavir, hydroxyurea, ribavirin, IL-2, IL-12, pentafuside, Yissum No.11607 and AG-1549. In particular, the combinations known as HAART are contemplated for use in combination with the compound of this invention.

For combination treatment with more than one active agent, where the active agents are in separate dosage formulations, the active agents may be administered separately or in conjunction. In addition, the administration of one element may be prior to, concurrent to, or subsequent to the administration of the other agent.

Another aspect of the invention provides a method of treating solid organ transplant rejection, graft v. host disease, arthritis, rheumatoid arthritis, inflammatory bowel disease, atopic dermatitis, psoriasis, asthma, allergies or multiple sclerosis comprising administering to a patient in need of such treatment a therapeutically effective amount of one or more compounds of formula I, preferably in combination with one or more pharmaceutically acceptable carriers. In another embodiment, the method for treating solid organ transplant rejection, graft v. host disease, rheumatoid arthritis, inflammatory bowel disease or multiple sclerosis further comprises administering one or more other agents useful in the treatment of said diseases in combination with one or more compounds of formula I.

Agents known in the treatment of rheumatoid arthritis, transplant and graft v. host disease, inflammatory bowel disease and multiple sclerosis which can be administered in combination with the compound of the present invention are as follows:

solid organ transplant rejection and graft v. host disease: immune suppressants such as cyclosporine and Interleukin-10 (IL-10), tacrolimus, antilymphocyte globulin, OKT-3 antibody, and steroids;

inflammatory bowel disease: IL-10 (see U.S. Pat. No. 5,368,854), steroids and azulfidine;

rheumatoid arthritis: methotrexate, azathioprine, cyclophosphamide, steroids and mycophenolate mofetil;

multiple sclerosis: interferon-beta, interferon-alpha, and steroids.

Another aspect of the invention relates to a kit comprising in separate containers in a single package pharmaceutical composition for use in combination to treat Human Immunodeficiency Virus. In one container, a pharmaceutical composition comprises one or more compounds of formula I in one or more pharmaceutically acceptable carriers, and in separate containers, one or more pharmaceutical compositions comprising an effective amount of one or more antiviral agents or other agents useful in the treatment of Human Immunodeficiency Virus in one or more pharmaceutically acceptable carriers.

The goal of the HIV-1 therapy of the present invention is to reduce the HIV-1-RNA viral load below the detectable limit. The "detectable limit of HIV-1-RNA" in the context of the present invention means that there are fewer than about 200 to fewer than about 50 copies of HIV-1-RNA per ml of plasma of the patient as measured by quantitative, multi-cycle reverse transcriptase PCR methodology. HIV-1-RNA is preferably measured in the present invention by the methodology of Amplicor-1 Monitor 1.5 (available from Roche Diagnsotics) or of Nuclisens HIV-1 QT -1.

The following assays can be used to determine the CCR5 inhibitory and antagonistic activity of the compounds of the invention.

CCR5 Membrane Binding Assay:

A high throughput screen utilizing a CCR5 membrane binding assay identifies inhibitors of RANTES binding. This assay utilizes membranes prepared from NIH 3T3 cells expressing the human CCR5 chemokine receptor which have the ability to bind to RANTES, a natural ligand for the receptor. Using a 96-well plate format, membrane preparations are incubated with $^{125}$I-RANTES in the presence or absence of compound for one hour. Compounds are serially diluted over a wide range of 0.001 ug/ml to 1 ug/ml and tested in triplicates. Reaction cocktails are harvested through glass fiber filters, and washed thoroughly. Total counts for replicates are averaged and data reported as the concentration required to inhibit 50 percent of total $^{125}$I-RANTES binding. Compounds with potent activity in the membrane binding assay are further characterized in seconday cell-based HIV-1 entry and replication assays.

HIV-1 Entry Assay:

Replication defective HIV-1 reporter virions are generated by cotransfection of a plasmid encoding the NL4-3 strain of HIV-1 (which has been modified by mutation of the envelope gene and introduction of a luciferase reporter plasmid) along with a plasmid encoding one of several HIV-1 envelope genes as described by Connor et al, Virology, 206 (1995), p. 935944. Following transfection of the two plasmids by calcium phosphate precipitation, the viral supernatants are harvested on day 3 and a functional viral titer determined. These stocks are then used to infect U87 cells stably expressing CD4 and the chemokine receptor CCR5 which have been preincubated with or without test compound. Infections are carried out for 2 hours at 37° C., the cells washed and media replaced with fresh media containing compound. The cells are incubated for 3 days, lysed and luciferase activity determined. Results are reported as the concentration of compound required to inhibit 50% of the luciferase activity in the control cultures.

HIV-1 Replication Assay:

This assay uses primary peripheral blood mononuclear cells or the stable U87-CCR5 cell line to determine the effect of anti-CCR5 compounds to block infection of primary HIV-1 strains. The primary lymphocytes are purified from normal healthy donors and stimulated in vitro with PHA and IL-2 three days prior to infection. Using a 96-well plate format, cells are pretreated with drug for 1 hour at 37° C. and subsequently infected with an M-tropic HIV-1 isolates. Following infection, the cells are washed to remove residual inoculum and cultured in the presence of compound for 4 days. Culture supernatants are harvested and viral replication measured by determination of viral p24 antigen concentration.

Calcium Flux Assay:

Cells expressing the HIV coreceptor CCR5 are loaded with calcium sensitive dyes prior to addition of compound or the natural CCR5 ligand. Compounds with agonist properties will induce a calcium flux signal in the cell, while the compounds of this invention are identified as compounds which do not induce signaling by themselves but are capable of blocking signaling by the natural ligand RANTES.

GTP☐S Binding Assay (Secondary Membrane Binding Assay):

A GTP☐S binding assay measures receptor activation by CCR5 ligands. This assay measures the binding of $^{35}$S labeled-GTP to receptor coupled G-proteins that occurs as a result of receptor activation by an appropriate ligand. In this assay, the CCR5 ligand, RANTES, is incubated with membranes from CCR5 expressing cells and binding to the receptor activation (or binding) is determined by assaying for bound $^{35}$S label. The assay quantitatively determines if compounds exhibit agonist characteristics by inducing activation of the receptor or alternatively antagonist properties by measuring inhibition of RANTES binding in a competitive or non-competitive fashion.

Chemotaxis Assay:

The chemotaxis assay is a functional assay which characterizes the agonist vs. antagonist properties of the test compounds. The assay measures the ability of a non-adherent murine cell line expressing human CCR5 (BaF-550) to migrate across a membrane in response to either test compounds or natural ligands (i.e., RANTES, MIP-1β). Cells migrate across the permeable membrane towards compounds with agonist activity. Compounds that are antagonists not only fail to induce chemotaxis, but are also capable of inhibiting cell migration in response to known CCR5 ligands.

Luciferase Replication Assay:

Plasmids encoding the full length genome of HIV-1 pNL-4-Luc with the gp120 V-3 loop replaced by the Bgl II fragment of HIV-1 ADA, YU-2 or HxB (ADA-Luc-FL, YU-2-Luc-FL and HxB-Luc-FL) are obtained from Dr. Susan Pontow (Washington University, St. Louis Mo.). Replication-competent luciferase reporter virus stocks are generated by transfection of plasmids into 293T cells using Superfect (Qiagen) or Mirus transfection reagents. Viral stocks are collected 48 hours following transfection and titered for luciferase production on U-87-CCR5 or CXCR4 cells. U87-CD4-CCR5 cells ($10^4$/well) are plated in 96-well cell culture plates and incubated overnight. Media is removed and replaced with 50 μl of fresh culture media (DMEM, 10% FCS) and 50 μl of compound diluted in culture medium. Cells are incubated with compound at 37° C. for 1 hour. The resultant supernatant is removed and replaced with 20 μl of media containing compound and infected with an equal volume of diluted or undiluted virus stock at 37° C. for 3-4 hours. The cells are washed once with DMEM, and 200 µl of media containing compound is added. The cultures are incubated for 3 days, the cells lysed in luciferase lysis buffer (Promega, Madison, Wis.) and transferred to Immulon plates (Dynex Technologies, Chantilly Va.). An equal volume of luciferase substrate (Promega, Madison Wis.) is added to lysates and the plates read immediately in a Wallac Luminometer. Fifty and ninety percent inhibitory concentrations are determined using GraphPad PRISM software.

Compounds useful in this invention are exemplified by the following preparative examples, which should not be construed to limit the scope of the disclosure. Alternative mechanistic pathways and analogous structures within the scope of the invention may be apparent to those skilled in the art.

EXAMPLE 1

Compound 4

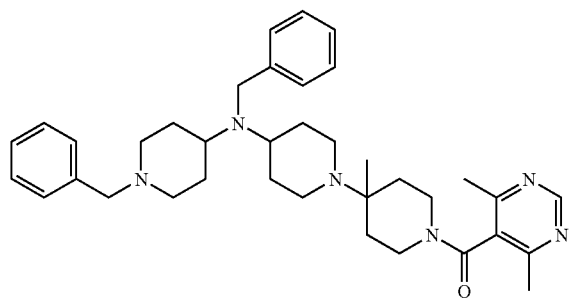

Step 1

4-Hydroxy-piperidine (1.0 g, 9.9 mmol) and N-Boc-4-piperidone (1.97 g, 9.9 mmol), and Ti(OiPr)$_4$ (3.2 mL, 10.9 mmol) were taken up in CH$_2$Cl$_2$ and stirred at rt for 19 h. To this solution, 24 mL of Et$_2$AlCN (1.0 M in toluene) were added. The resulting solution was stirred at rt for 24 h. The solution was cooled and quenched with sat. NaHCO$_3$. The mixture was diluted with EtOAc and filtered through a plug of Celite. The filter cake was rinsed with EtOAc and H$_2$O. The layers were separated, and the aqueous layer was extracted with EtOAc. The combined EtOAc layers were washed with brine and dried (Na$_2$SO$_4$). Filtration through Celite and concentration gave a cyanide compound (2.84 g, 93%) as a solid.

Step 2

The cyanide compound from step 1 (2.84 g, 9.2 mmol) was taken up in THF and cooled to 0° C. Methyl magnesium bromide (15 mL of 3.0 M in diethyl ether) was added to the solution at 0° C. The solution was warmed to rt and stirred at that temperature for 16 h. The solution was cooled to 0° C. and quenched with 1 N NaOH$_{(aq.)}$. The mixture was filtered through a plug of Celite. The Celite was rinsed with EtOAc. The aqueous layer was extracted with EtOAc. The combined EtOAc layers were washed with brine and dried (Na$_2$SO$_4$). Filtration through Celite and concentration gave an alcohol (2.5 g, 90%) as an oil.

Step 3

DMSO (0.9 mL, 12.6 mmol) was taken up in CH$_2$Cl$_2$ and cooled to −40° C. (CO$_2$/CH$_3$CN). Oxalyl chloride (1.1 mL, 12.6 mmol) was added dropwise to the solution at −40° C. The solution was stirred at that temperature for 20 minutes. The alcohol from step 2 (2.5 g, 8.39 mmol) in CH$_2$Cl$_2$ was added to the solution at −40° C. The resulting solution was stirred at that temperature for 30 minutes. Triethyl amine (3.5 mL, 25.2 mmol) was added to the solution at −40° C., and the resulting slurry was warmed to rt. After 30 minutes, the solution was diluted with CH$_2$Cl$_2$ and washed with 1 N NaOH$_{(aq.)}$. The aqueous layer was extracted with CH$_2$Cl$_2$. The combined organic layers were dried (Na$_2$SO$_4$), filtered, and concentrated. Purification via flash chromatography (2/1 EtOAc/hexanes, SiO$_2$) gave 2.15 grams (87%) of a ketone as an oil that slowly solidified.

Step 4

Boc-piperidine (2.0 g, 6.7 mmol) was taken up in CH$_2$Cl$_2$ and TFA (7 mL) was added. The solution was stirred at rt for 1 h. The solution was concentrated. The resulting salt was taken up in H$_2$O and basified with NaOH. The solution was extracted with CH$_2$Cl$_2$. The aqueous layer was extracted with CH$_2$Cl$_2$. The combined organic layers were dried (Na$_2$SO$_4$), filtered, and concentrated to furnish 1.1 g (85%) of deprotected piperidine.

The deprotected piperidine 1.1 g (5.6 mmol), EDCI hydrochloride (1.6 g), HOBT (1.2 g), diisoproplyethylamine (1.8 g), and 4,6-dimethyl-3pyrimidine carboxylic acid (1.1 g) were taken up in CH$_2$Cl$_2$ and stirred at rt for 16 h. The solution was diluted with CH$_2$Cl$_2$ and washed with 1 N NaOH$_{(aq.)}$. The aqueous layer was extracted with CH$_2$Cl$_2$. The combined organic layers were dried over Na$_2$SO$_4$. Filtration through Celite and concentration gave 0.94 g (51%) of amide as a foam.

Step 5

The amide from step 4 (0.94 g, 2.8 mmol), 4-amino-N-benzyl piperidine (0.5 g), Na(AcO)$_3$BH (0.84 g), and HOAc (0.26 g) were taken up in CH$_2$Cl$_2$ and stirred at rt for 2 h. The solution was diluted with CH$_2$Cl$_2$ and washed with 1 N NaOH$_{(aq.)}$. The aqueous layer was extracted with CH$_2$Cl$_2$. The combined organic layers were dried over Na$_2$SO$_4$. Filtration through Celite and concentration gave an oil. Purification via flash chromatography (gradient: CH$_2$Cl$_2$-2% [7 N NH$_3$ in MeOH] in CH$_2$Cl$_2$-4% [7 N NH$_3$ in MeOH][in CH$_2$Cl$_2$, SiO$_2$) gave 1.2 g (84%) of amine as an oil. MS (FAB) 505.4 (MH+).

Step 6

The amine from step 5 (0.10 g, 0.20 mmol), benzaldehyde (0.06 g), and Na(AcO)$_3$BH (0.12 g) were taken up in CH$_2$Cl$_2$ and stirred at rt for 15 h. More benzaldehyde (0.06 g) and Na(AcO)$_3$BH (0.12 g) were added to the reaction. The reaction was stirred for an additional 15 h. The solution was diluted with CH$_2$Cl$_2$ and washed with 1 N NaOH$_{(aq.)}$. The aqueous layer was extracted with CH$_2$Cl$_2$. The combined organic layers were dried over Na$_2$SO$_4$. Filtration through Celite and concentration gave an oil. Purification via preparative layer chromatography (7% [7 N NH$_3$ in MeOH in CH$_2$Cl$_2$, SiO$_2$) gave 0.025 g (21%) of the product shown above in this example. MS (FAB) 595.5 (MH+).

The compounds shown below in Table 2 were prepared in a similar fashion as outlined above.

The compounds shown below in Table 2 were prepared in a similar fashion as oulined above for Example 1.

TABLE 2
| # | Structure | HIV Replication (luciferase) IC50 nM | HRMS found (MH+) |
|---|---|---|---|
| 1 | 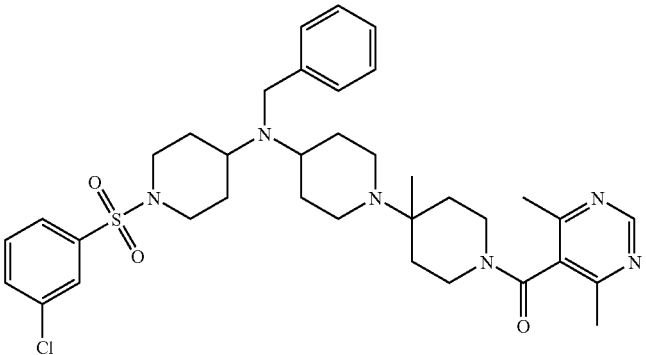 | 0.1 | 679.3197 |
| 2 | 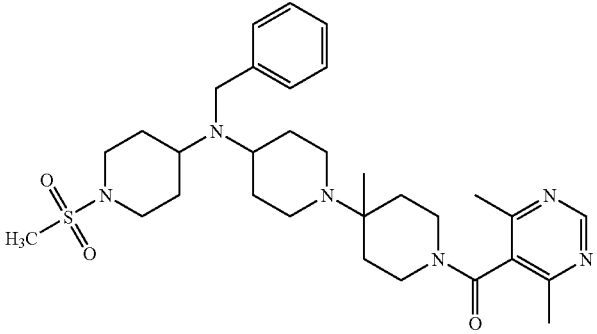 | 0.8 | 583.3428 |
| 3 | 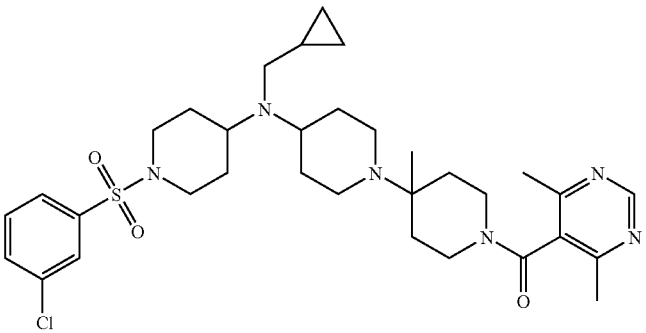 | 32 | 643.3185 |
| 4 | 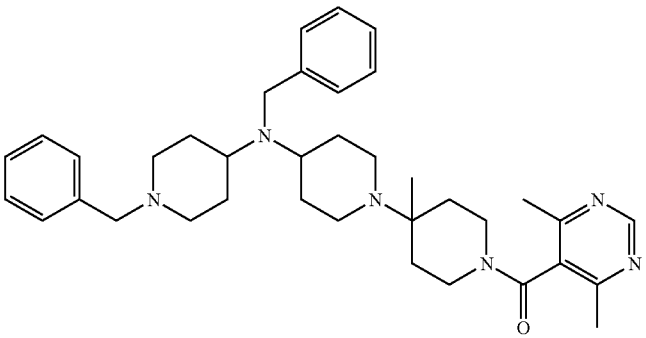 | 1.7 | 595.4115 |

TABLE 2-continued
| # | Structure | HIV Replication (luciferase) IC50 nM | HRMS found (MH+) |
|---|---|---|---|
| 5 | 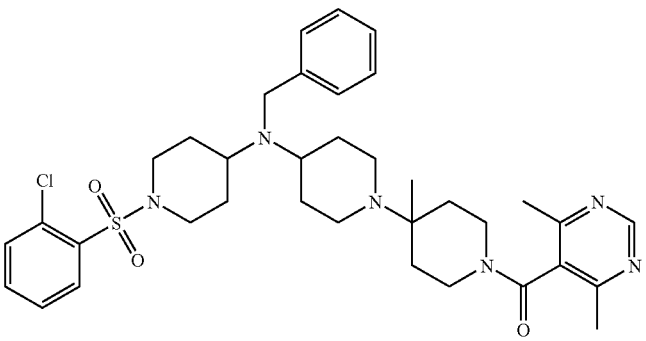 | 2.1 | 679.3184 |
| 6 | 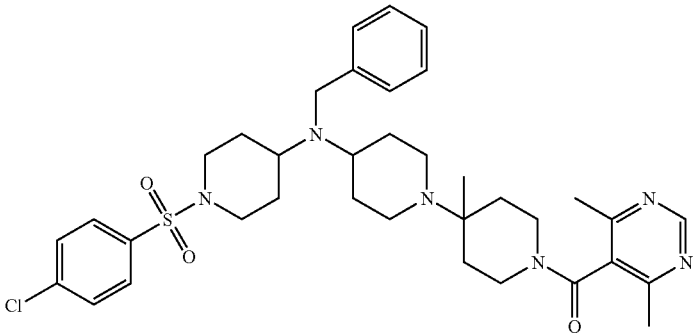 | 0.9 | 679.3181 |
| 7 | 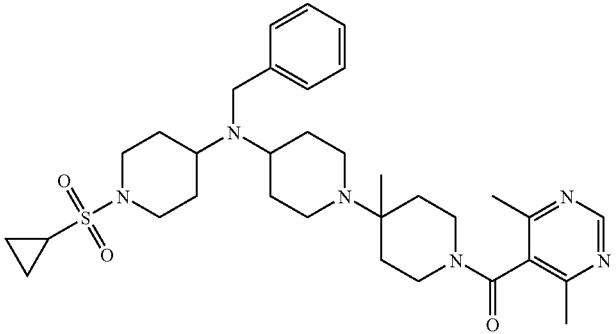 | 3 | 609.3598 |
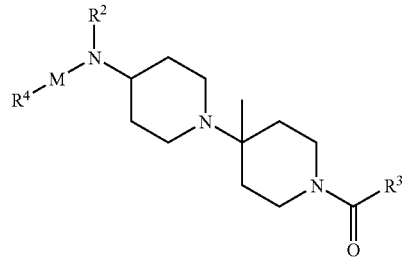

This series concentrates on when M=aryl or hetero-aryl. Most preferred are when $R^2$ is benzyl, phenyl, and cyclopropylmethyl.

EXAMPLE 2

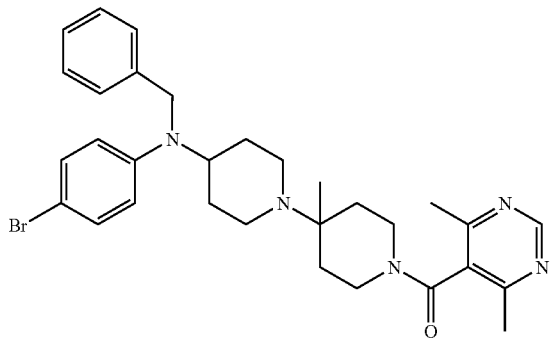

Compound 8

Step 1
4-Bromo aniline (8.3 g, 48 mmol), N-Boc-4-piperidone (8.0 g, 40 mmol), Na(AcO)$_3$BH (12.7 g, 60 mmol), and ACOH (3.5 mL, 60 mmol) were taken up in CH$_2$Cl$_2$ and stirred at 25° C. (17 h). The solution was diluted with CH$_2$Cl$_2$ and quenched with 1 N NaOH. The aqueous layer was extracted with CH$_2$Cl$_2$. The combined organic layers were dried (Na$_2$SO$_4$), filtered and concentrated. Purification via recrystallization (CH$_2$Cl$_2$/hexanes) gave 10.2 g (72%) of an amine product.

Step 2
The amine (1.5 g, 4.22 mmol), benzyl bromide (0.74 mL, 6.3 mmol), NaH (250 mg of a 60 wt % dispersion in oil), and KI (350 mg, 2.11) were taken up in DME and stirred at 100° C. (18 h). The solution was cooled and partitioned between EtOAc and H2O. The aqueous layer was extracted with EtOAc. The combined organic layers were washed with brine and dried (MgSO$_4$). Filtration and concentration followed by purification via flash chromatography (4/1 hexanes/Et$_2$O, SiO$_2$) gave 528 mg (28%) of a benzyl amine product.

Step 3
The benzyl amine product from step 2 and 4.0 M HCl in dioxane (5 mL) were taken up in MeOH, and the solution was stirred at 25° C. for 18 hours. The solution was concentrated. The residue was partitioned between CH$_2$Cl$_2$ and 1 N NaOH. The aqueous layer was extracted with CH$_2$Cl$_2$. The combined organic layers were dried with Na$_2$SO$_4$. Filtration and concentration gave 314 mg (77%) of a free amine product.

Step 4
The free amine product from step 3 was treated sequentially with 1) N-Boc-4-piperidone (181 mg, 0.91 mmol)/Ti(OiPr)$_4$(0.32 mL, 1.1 mmol) and 2) EtAlCN (1.1 mL of a 1.0 M solution in toluene) according to the conditions described above in Step 1 of Example 1. After work-up, 500 mg (Quant.) of a cyano-amine was obtained.

Step 5
The cyano-amine from step 4 was treated with MeMgBr (1.5 mL of a 3.0 M solution in Et$_2$O) according to the conditions described above in Step 2 of Example 1. Purification via preparative thin-layer chromatography (2/1 hexanes/EtOAc, SiO$_2$) gave 344 mg (70%) of the amine as a colorless oil.

Step 6
The amine from step 5 and 4.0 M HCl in dioxane (4 mL) were taken up in MeOH and stirred at 25° C. for 17 hours. The solution was concentrated. The HCl salt of the deprotected amine was used as is in the next step.

Step 7
The HCl salt from step 6, EDCI hydrochloride (169 mg, 0.88 mmol), HOBT (119 mg, 0.88 mmol), and iPr$_2$NEt (1.5 mL, 8.8 mmol), and 4,6-dimethyl-3-pyrimidine carboxylic acid (134 mg, 0.88 mmol) were taken up in CH$_3$CN and stirred at 25° C. for 20 hours. The solution was concentrated. The residue was partitioned between EtOAc and 1 N NaOH. The aqueous layer was extracted with EtOAc. The combined EtOAc layers were washed with brine and dried with Na$_2$SO$_4$. Filtration and concentration followed by purification via preparative, thin-layer chromatography (30/1 CH$_2$Cl$_2$/7 N NH$_3$, SiO$_2$) gave 172 mg (68%) of Compound 8. The amide was taken up in EtOAc and was precipitated as the HCl salt upon addition of 2.0M HCl in Et$_2$O. m.p. (HCl salt): 168-170 C. HRMS (MH+) calc'd for 576.2338; Found: 576.2331.

The following compounds were prepared via similar procedures:

TABLE 3

| Example | Structure | HIV Replication (luciferase) IC50 nM | HRMS found (MH+) |
|---|---|---|---|
| 9 | 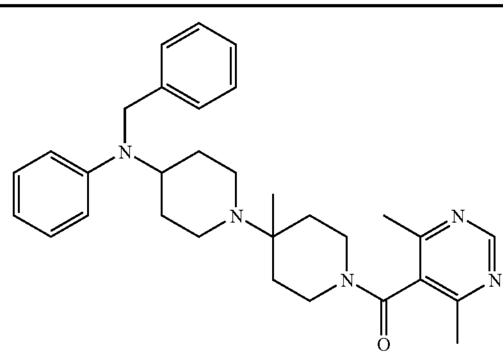 | 3 | 498.3233 |

TABLE 3-continued

| Example | Structure | HIV Replication (luciferase) IC50 nM | HRMS found (MH+) |
|---|---|---|---|
| 10 | 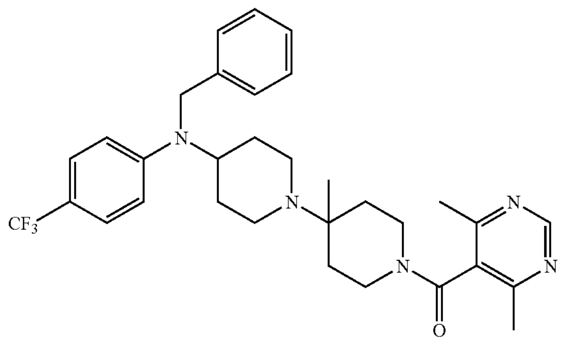 | 0.5 | 566.3099 |
| 11 | 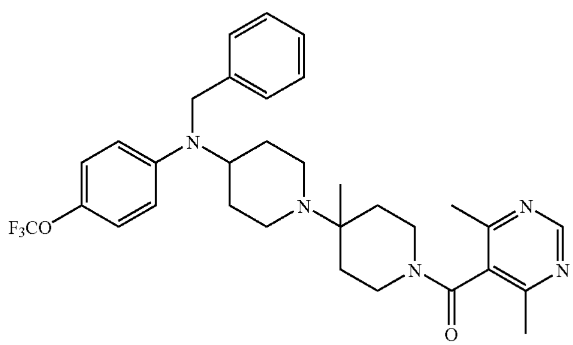 | 0.2 | 582.3064 |
| 12 | 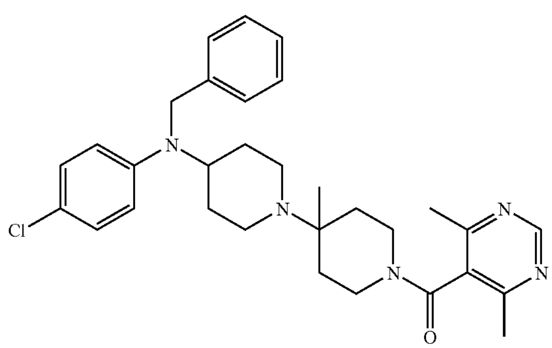 | 0.2 | 532.2850 |
| 13 | 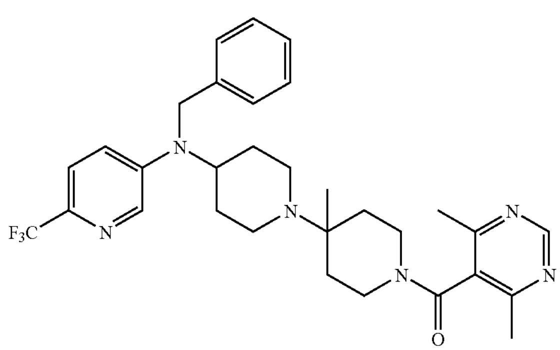 | 0.2 | 567.3063 |

TABLE 3-continued

| Example | Structure | HIV Replication (luciferase) IC50 nM | HRMS found (MH+) |
|---|---|---|---|
| 14 | 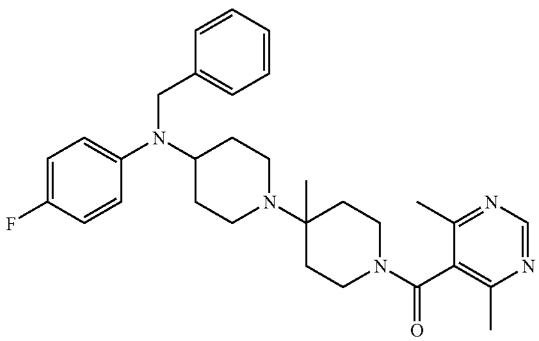 | 0.1 | 516.3034 |
| 15 | 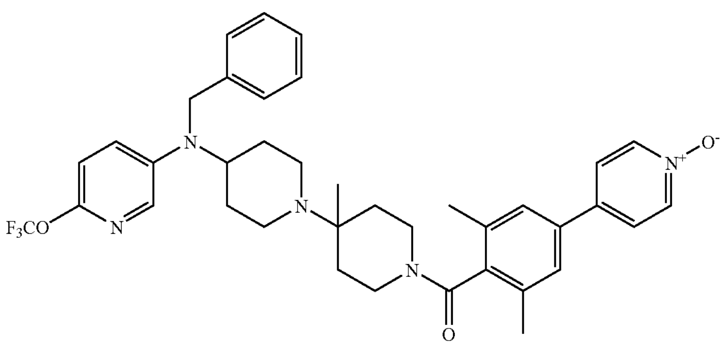 | 10 | 673.3375 |
| 16 | 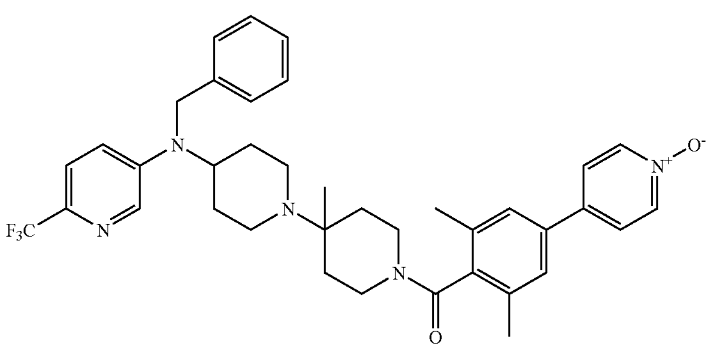 | 0.5 | 658.3377 |
| 17 | 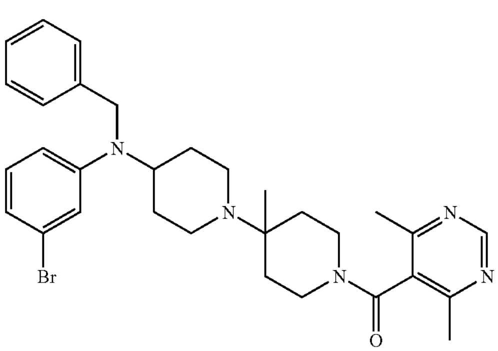 | 0.1 | 576.2331 |

TABLE 3-continued
| Example | Structure | HIV Replication (luciferase) IC50 nM | HRMS found (MH+) |
|---|---|---|---|
| 18 | 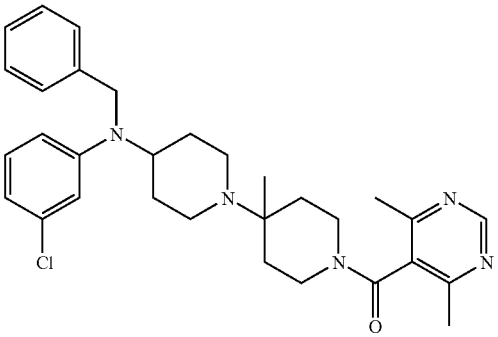 | 0.1 | 532.2832 |
| 19 | 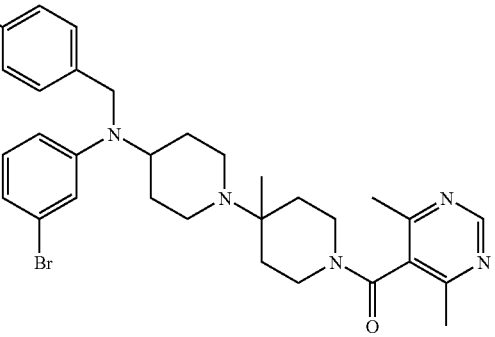 | 0.5 | 594.2235 |
| 20 | 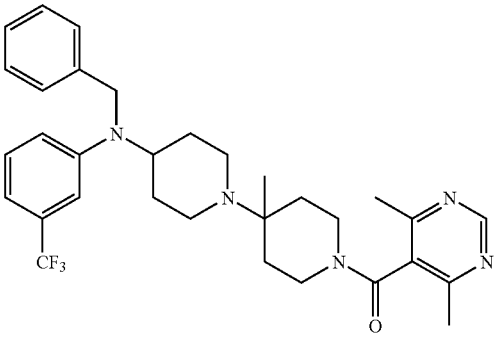 | 0.2 | 566.3116 |
| 21 | 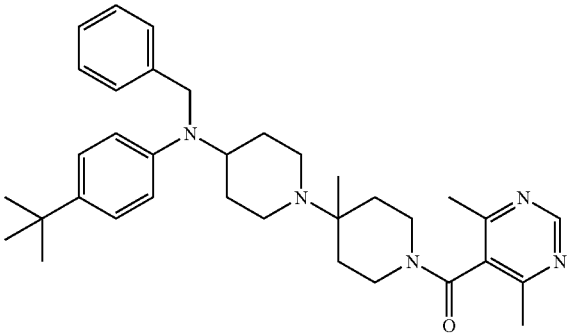 | 1 | 554.3849 |

TABLE 3-continued

| Example | Structure | HIV Replication (luciferase) IC50 nM | HRMS found (MH+) |
|---|---|---|---|
| 22 | 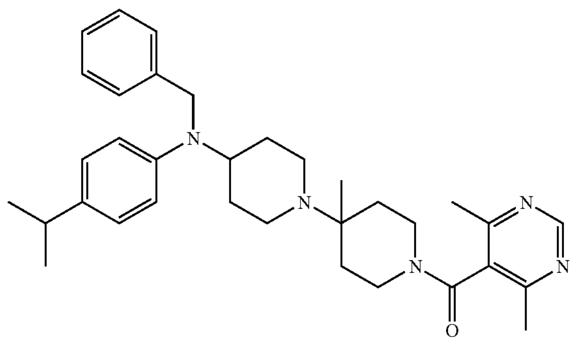 | 0.2 | 540.3713 |
| 23 | 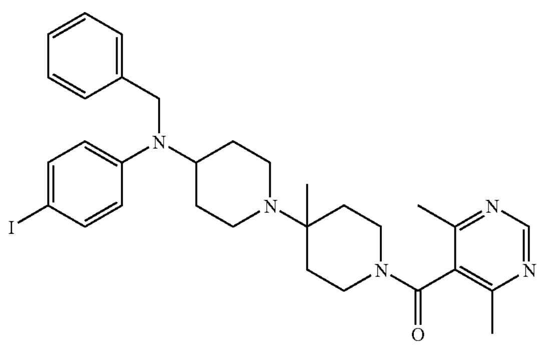 | 0.1 | 624.2203 |
| 24 | 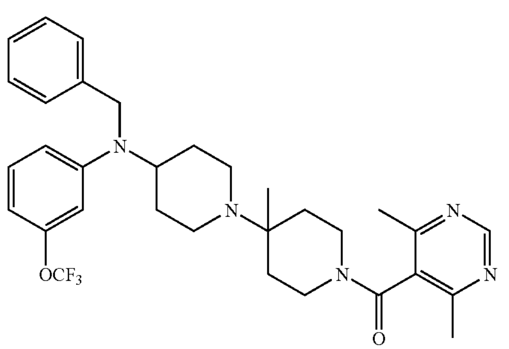 | 0.2 | 582.3067 |
| 25 | 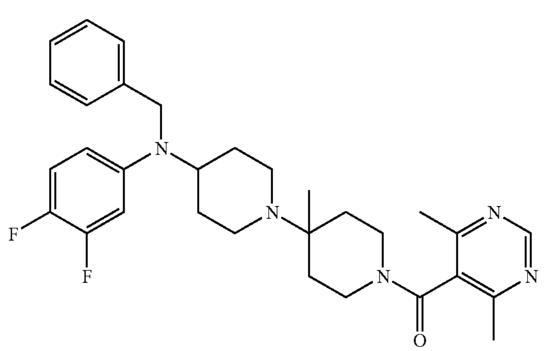 | 0.1 | 534.3053 |

TABLE 3-continued
| Example | Structure | HIV Replication (luciferase) IC50 nM | HRMS found (MH+) |
|---|---|---|---|
| 26 | 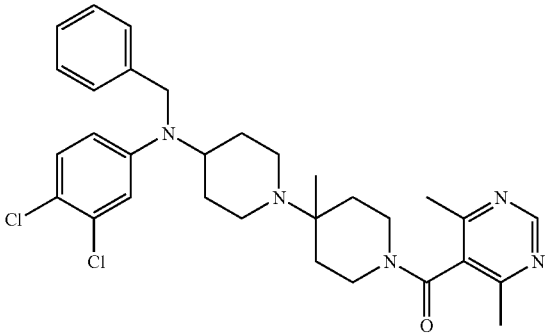 | 0.3 | 566.2460 |
| 27 | 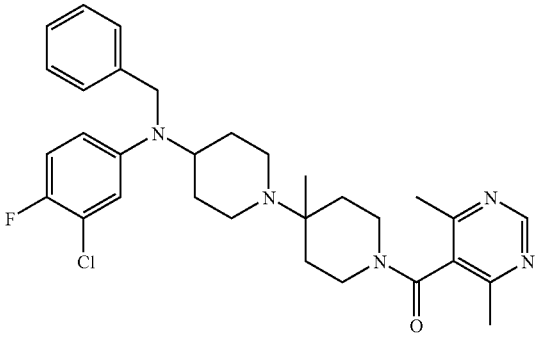 | 0.1 | 550.2753 |
| 28 | 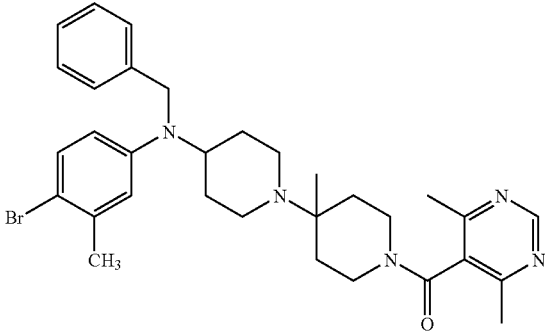 | 0.22 | 590.2500 |
| 29 | 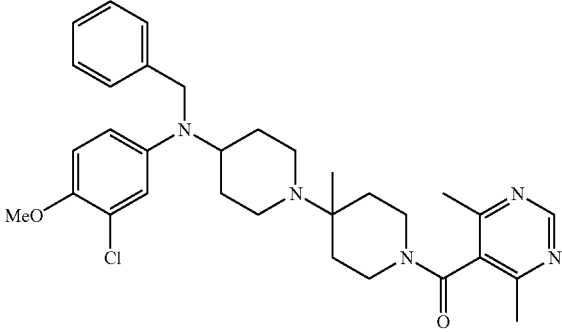 | 0.1 | 562.2959 |

TABLE 3-continued

| Example | Structure | HIV Replication (luciferase) IC50 nM | HRMS found (MH+) |
|---|---|---|---|
| 30 | 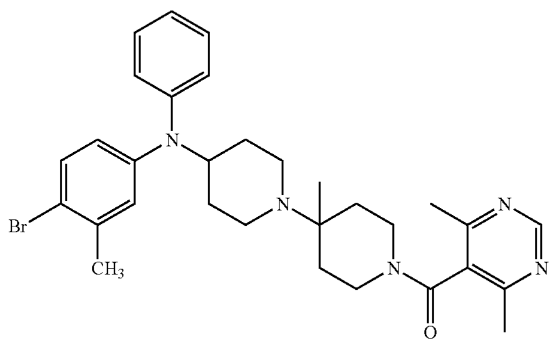 | 0.26 | 578.2314 |
| 31 | 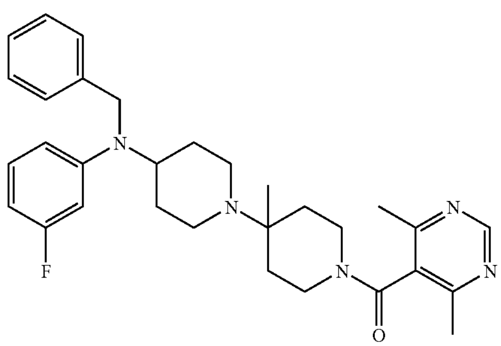 | 0.44 | 516.3151 |
| 32 | 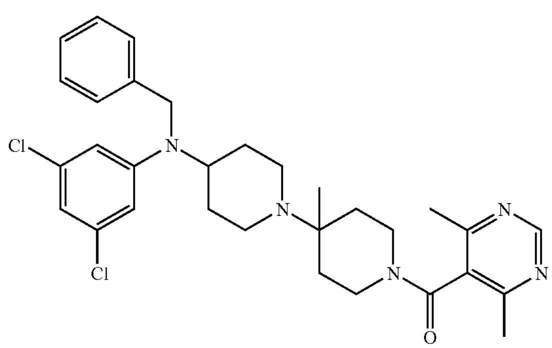 | 1.7 | 566.2464 |
| 33 | 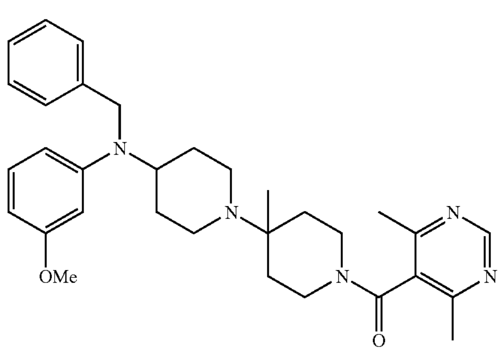 | 0.53 | 528.3349 |

TABLE 3-continued

| Example | Structure | HIV Replication (luciferase) IC50 nM | HRMS found (MH+) |
|---|---|---|---|
| 34 | 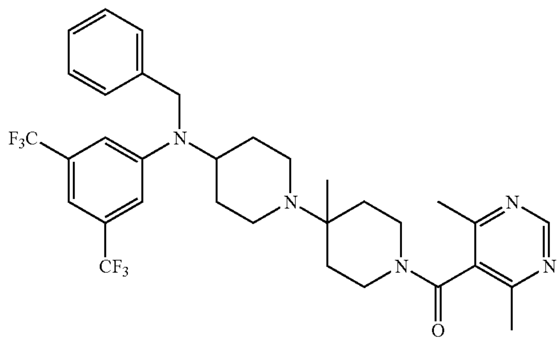 | 10 | 634.2993 |
| 35 | 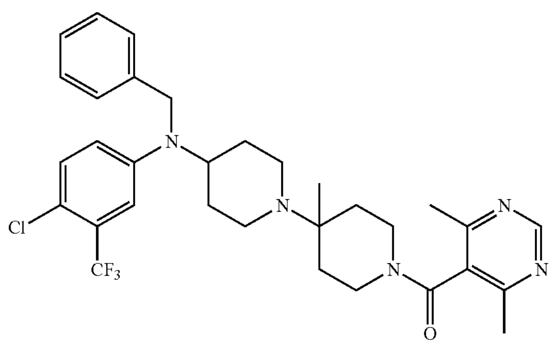 | 2 | 600.2712 |
| 36 | 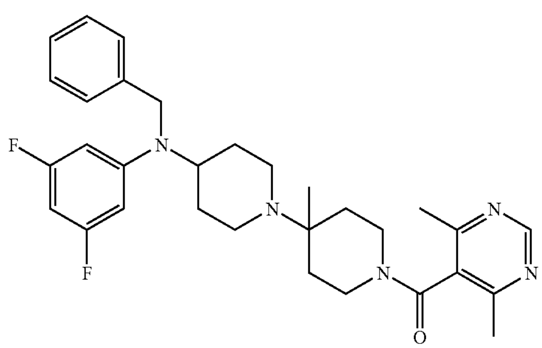 | 0.1 | 534.3040 |
| 37 | 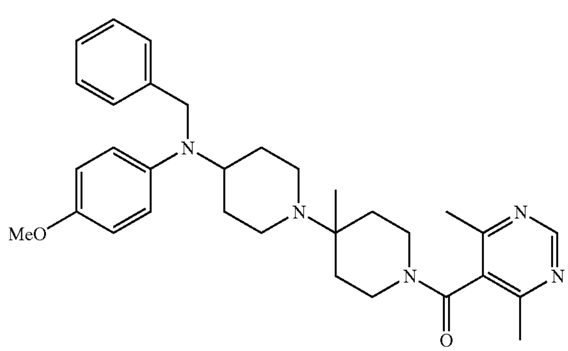 | 0.1 | 528.3348 |

TABLE 3-continued

| Example | Structure | HIV Replication (luciferase) IC50 nM | HRMS found (MH+) |
|---|---|---|---|
| 38 | 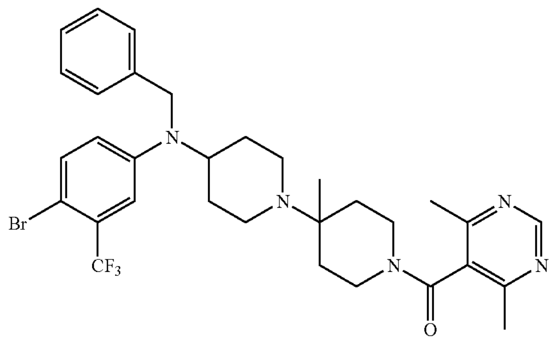 | 3 | 646.2207 |
| 39 | 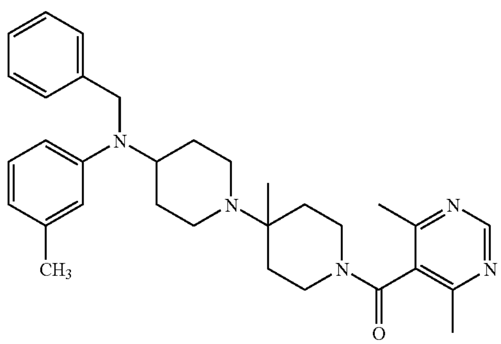 | 0.1 | 512.3383 |
| 40 | 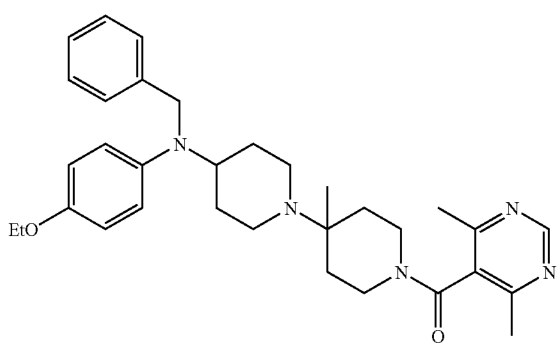 | <0.1 | 542.3489 |
| 41 | 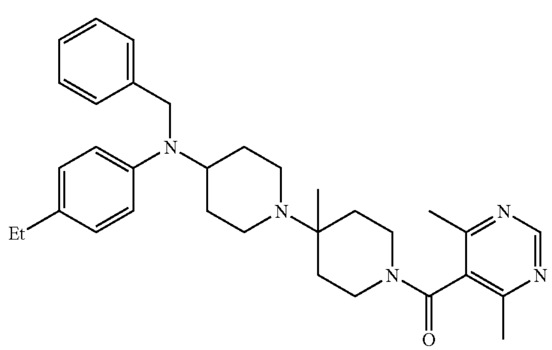 | <0.1 | 526.3541 |

TABLE 3-continued

| Example | Structure | HIV Replication (luciferase) IC50 nM | HRMS found (MH+) |
|---|---|---|---|
| 42 | 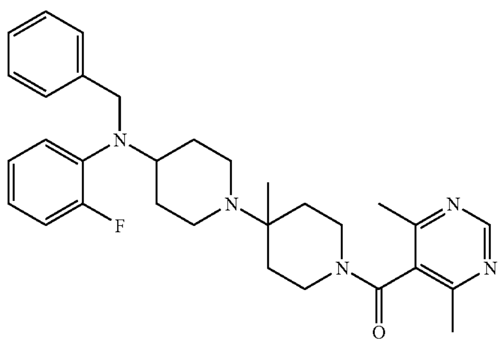 | 0.8 | 516.3142 |
| 43 | 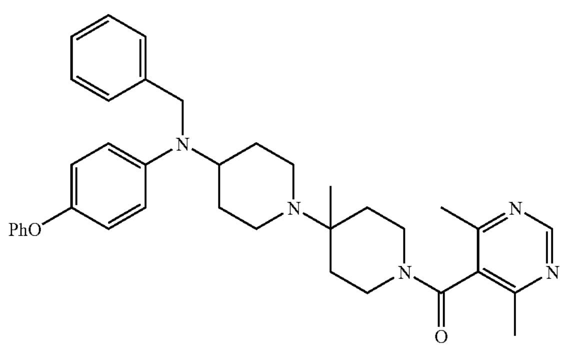 | 2 | 590.3502 |
| 44 | 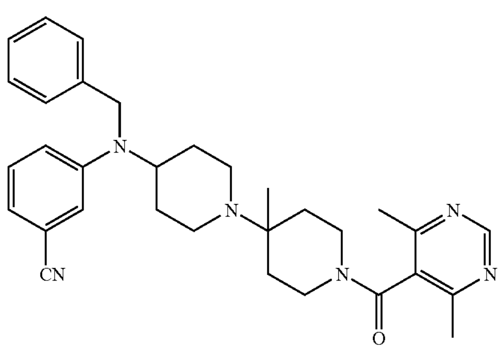 | 0.1 | 523.3180 |
| 45 | 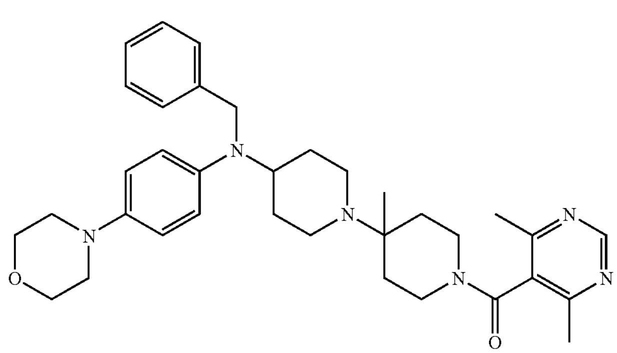 | 0.9 | 538.3765 |

TABLE 3-continued
| Example | Structure | HIV Replication (luciferase) IC50 nM | HRMS found (MH+) |
|---|---|---|---|
| 46 | 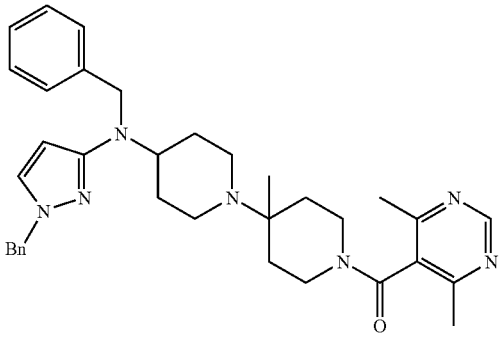 | 2 | 578.3603 |
| 47 | 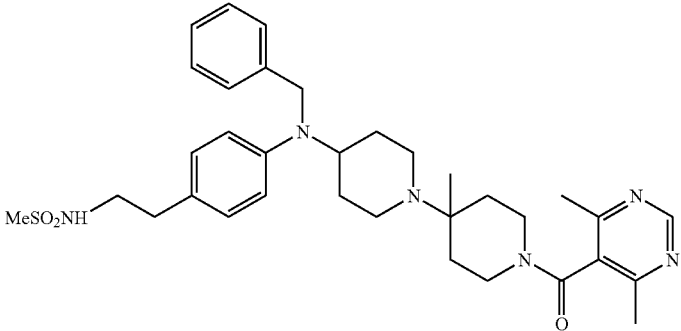 | 0.05 | 619.3441 |
| 48 | 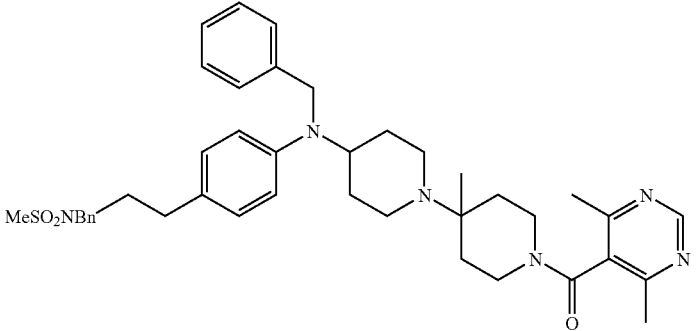 | 0.8 | 709.3915 |
| 49 | 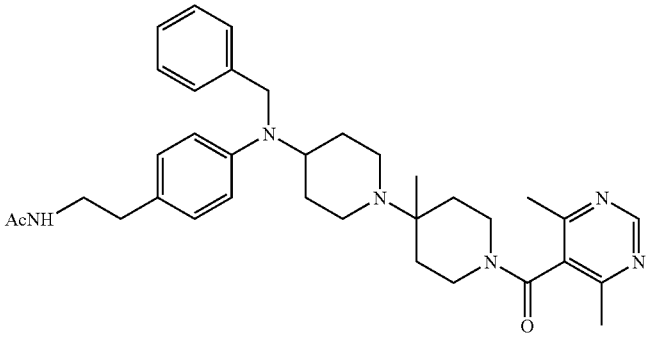 | 0.4 | 583.3756 |

TABLE 3-continued

| Example | Structure | HIV Replication (luciferase) IC50 nM | HRMS found (MH+) |
|---|---|---|---|
| 50 | 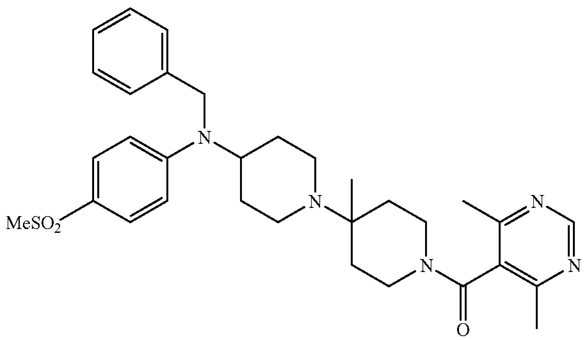 | 1 | 576.2998 |
| 51 | 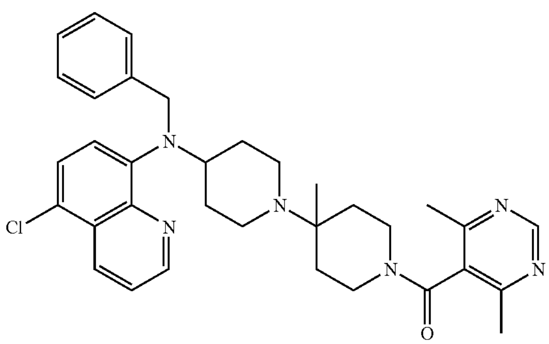 | 0.32 | 583.2961 |
| 52 | 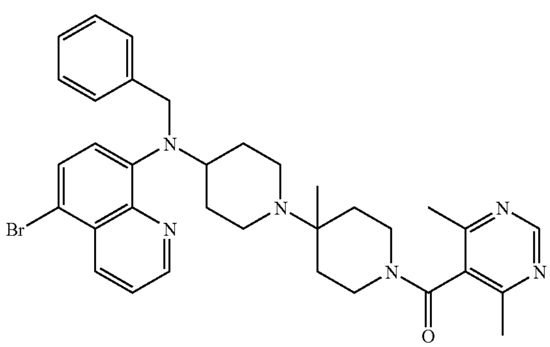 | 1 | 629.2440 |
| 53 | 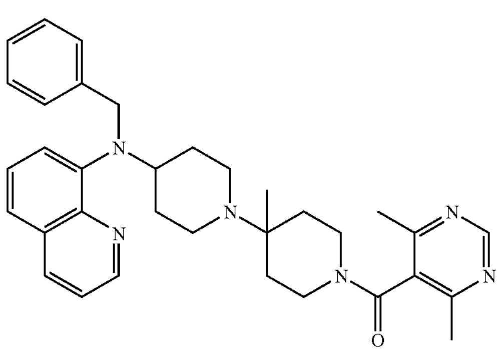 | 0.6 | 549.3349 |

TABLE 3-continued

| Example | Structure | HIV Replication (luciferase) IC50 nM | HRMS found (MH+) |
|---|---|---|---|
| 54 | 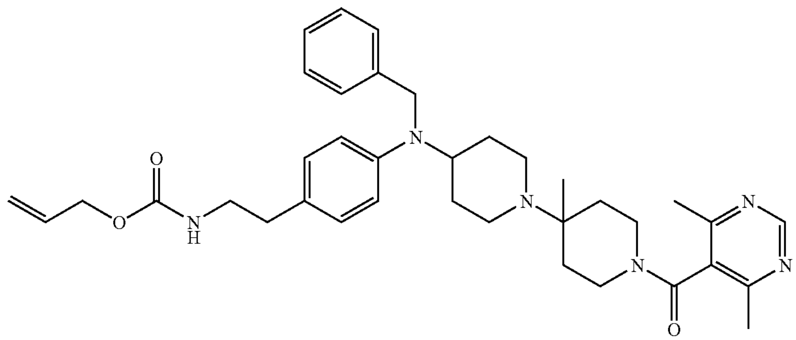 | 0.6 | 625.3853 |
| 55 | 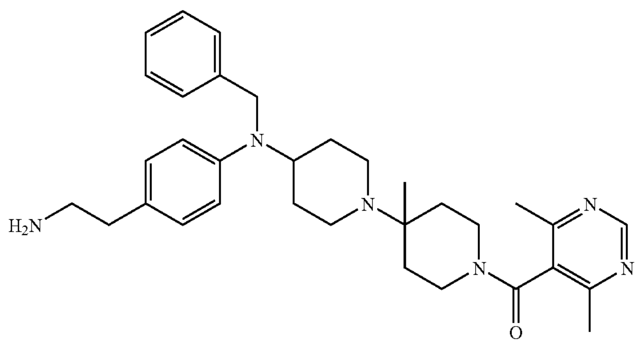 | 3.5 | 541.3663 |
| 56 | 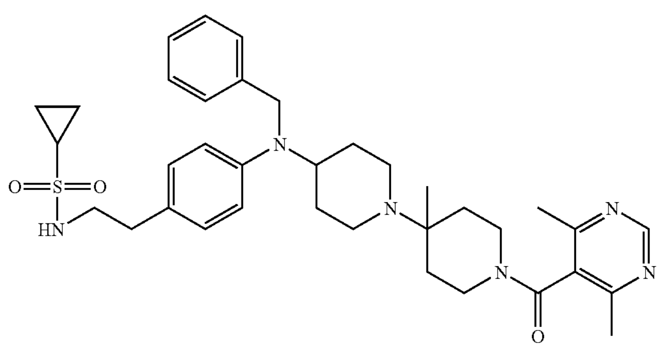 | 0.2 | 645.3600 |
| 57 | 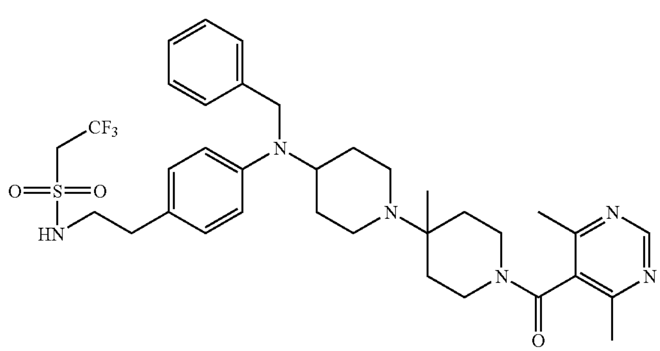 | 0.4 | 687.3323 |

TABLE 3-continued

| Example | Structure | HIV Replication (luciferase) IC50 nM | HRMS found (MH+) |
|---|---|---|---|
| 58 | 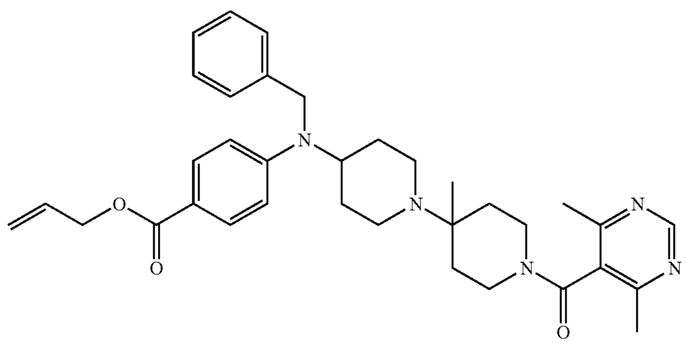 | 2 | 582.3459 |
| 59 | 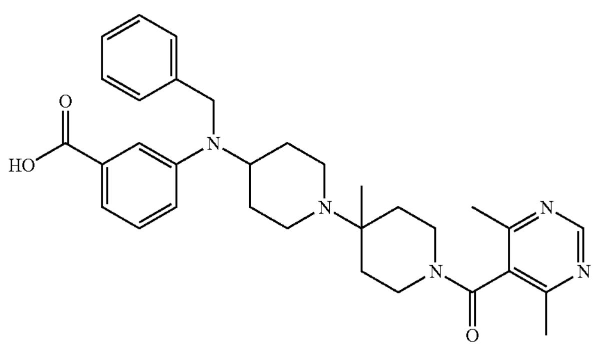 | 4 | 542.3118 |
| 60 | 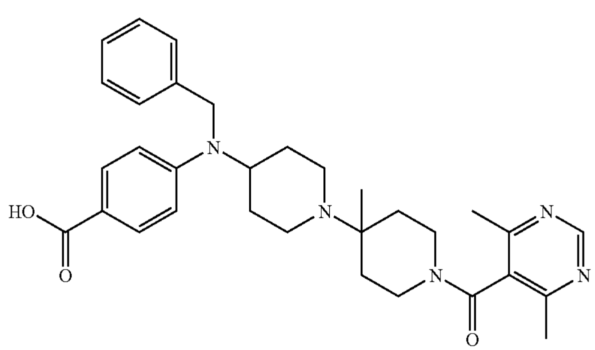 | 27 | 542.3136 |
| 61 | 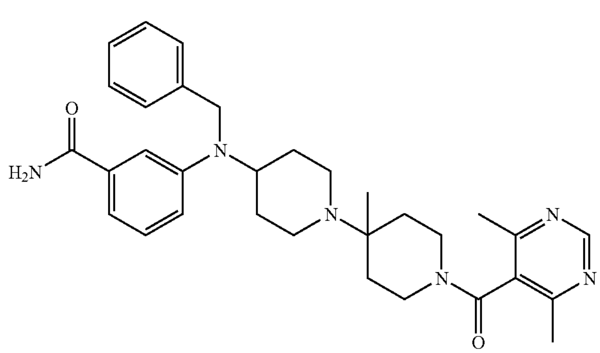 | 0.5 | 541.3283 |

TABLE 3-continued

| Example | Structure | HIV Replication (luciferase) IC50 nM | HRMS found (MH+) |
|---|---|---|---|
| 62 | 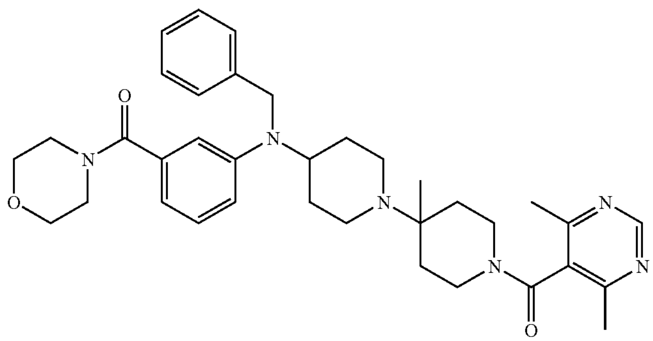 | 4 | 611.3705 |
| 63 | 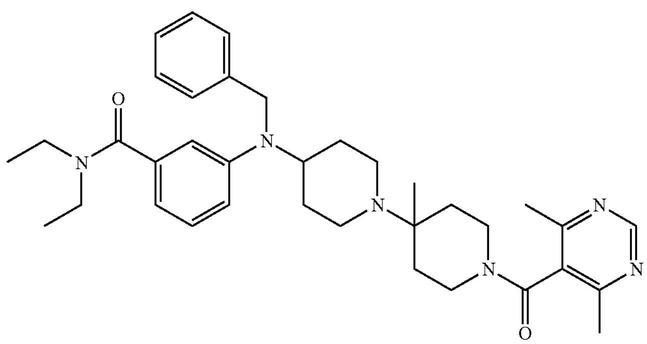 | 6 | 597.3910 |
| 64 | 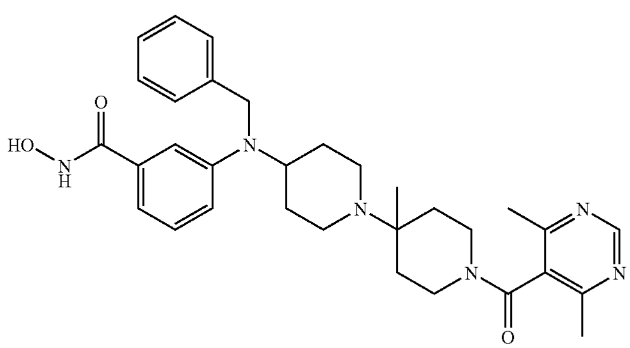 | 4 | 557.3230 |
| 65 | 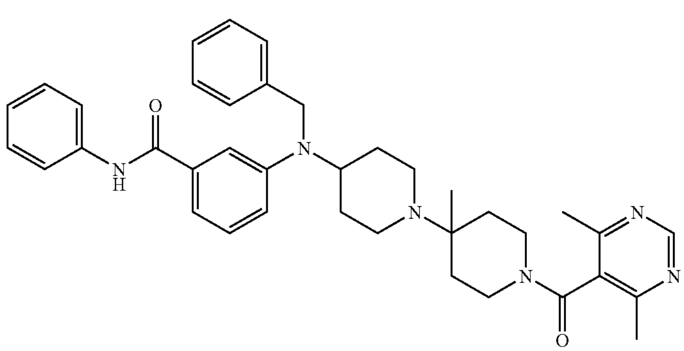 | 2 | 617.3610 |

TABLE 3-continued

| Example | Structure | HIV Replication (luciferase) IC50 nM | HRMS found (MH+) |
|---|---|---|---|
| 66 | 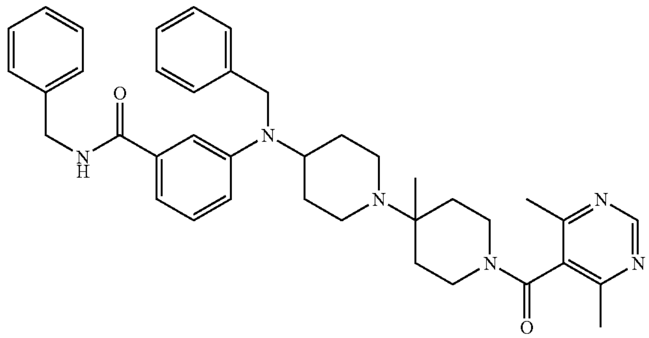 | 1 | 631.3769 |
| 67 | 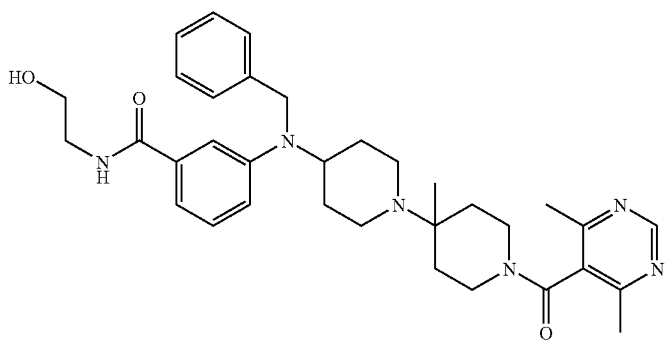 | 6 | 585.3561 |
| 68 | 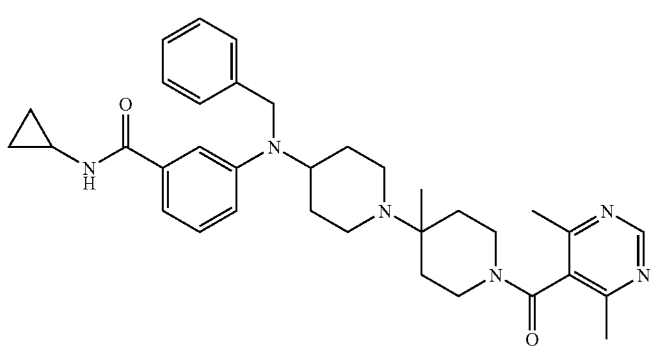 | 2 | 581.3598 |

EXAMPLE 3

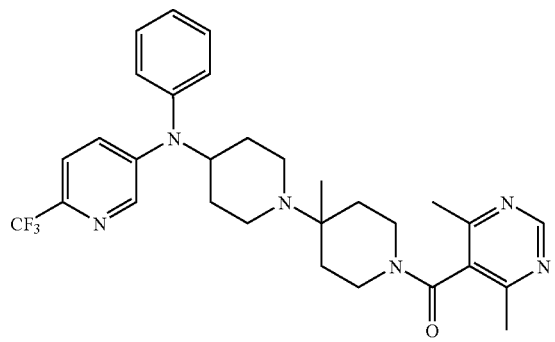

Compound 69

Step 1

3-Amino-6(trifluoromethyl)pyridine (1.0 g, 6.2 mmol), N-Boc-4-piperidone (1.5 g, 7.4 mmol), Na(AcO)$_3$BH (2.0 g, 9.3 mmol), and AcOH (0.35 mL, 6.2 mmol) were taken up in 1,2-dichloroethane and stirred at 55° C. for 17 hours. The solution was diluted with CH$_2$Cl$_2$ and quenched with 1 N NaOH. The aqueous layer was extracted with CH$_2$Cl$_2$. The combined organic layers were dried (Na$_2$SO$_4$), filtered and concentrated to furnish a yellow oil. The residue was resubjected to the reaction conditions for 20 hours. After workup, a yellow oil was obtained. The amine product was purified via recrystallization (CH$_2$Cl$_2$/hexanes) to give 1.6 g (75%) of the amine.

Step 2

The amine from step 1 (500 mg, 1.45 mmol), Ph$_3$Bi (1.28 g, 2.9 mmol), Cu(OAc)$_2$ (530 mg, 2.9 mmol), and Et$_3$N (0.40 mL, 2.9 mmol) were taken up in toluene and heated at 90° C. for 18 hours. More Ph$_3$Bi, Cu(OAc)$_2$, and Et$_3$N were added, and the reaction was stirred at 90° C. (48 h). The solution was filtered through Celite and concentrated. Purification via flash chromatography (3/1 hexanes/EtOAc, SiO$_2$) gave 352 mg (58%) of the diphenyl amine as a colorless oil.

Steps 3,4,5,6 and 7

The Boc amine from step 2 was converted into the pyrimidine amide following steps 3-7 described above in Example 2AD. Purification via preparative thin layer chromatography (3/1 hexanes/acetone, SiO2) gave 49 mg of Compound 69. HRMS (MH+) calc'd for 553.2903: Found, 553.2907. m.p. (HCl): 189-193 C. IC$_{50}$=0.11 nm The following compounds were prepared via similar procedures:

TABLE 4

| Example | SCH | Structure | HIV Replication (luciferase) IC50 nM | HRMS found (MH+) |
|---|---|---|---|---|
| 70 | | 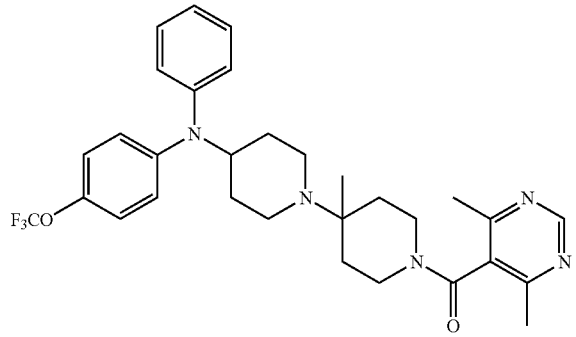 | 1 | 568.2905 |
| 71 | | 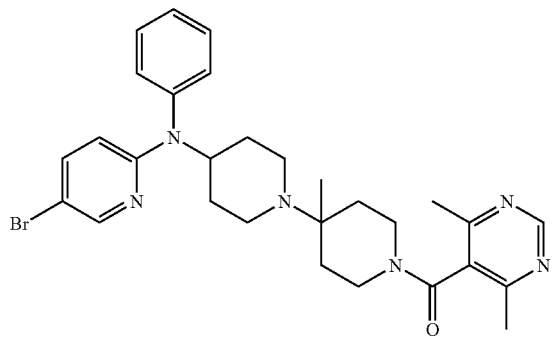 | 0.6 | 563.2143 |

TABLE 4-continued
| Example | SCH | Structure | HIV Replication (luciferase) IC50 nM | HRMS found (MH+) |
|---|---|---|---|---|
| 72 | | 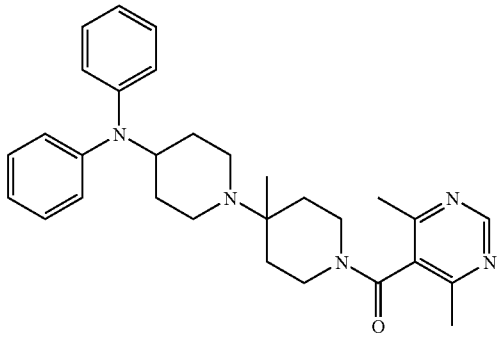 | 0.3 | 484.3080 |
| 73 | | 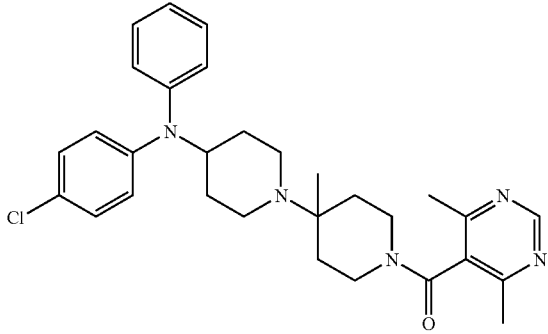 | 0.3 | 518.2695 |
| 74 | | 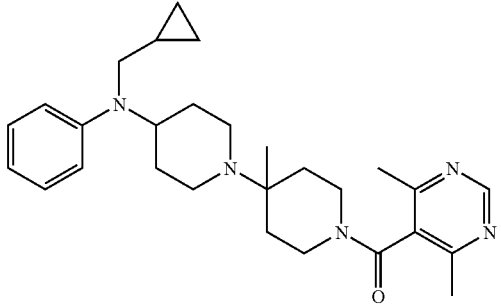 | 10 | 462.3235 |
| 75 | | 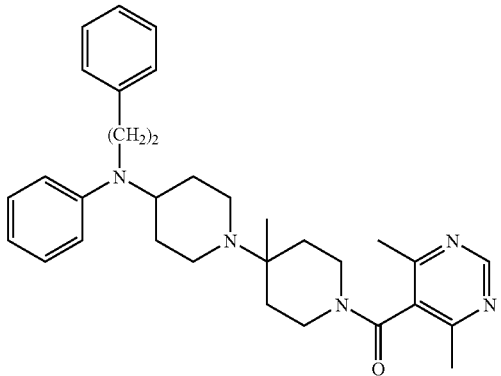 | 38 | 512.3396 |

TABLE 4-continued
| Example | SCH | Structure | HIV Replication (luciferase) IC50 nM | HRMS found (MH+) |
|---|---|---|---|---|
| 76 | | 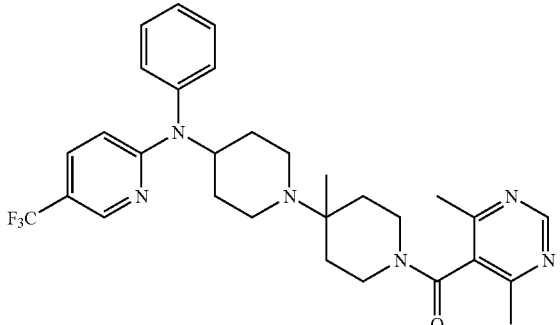 | 0.2 | 553.2912 |
| 77 | | 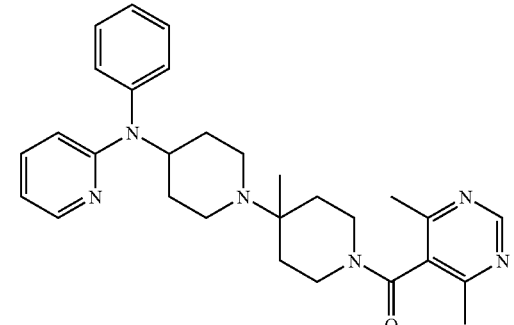 | 7 | 485.3033 |
| 78 | | 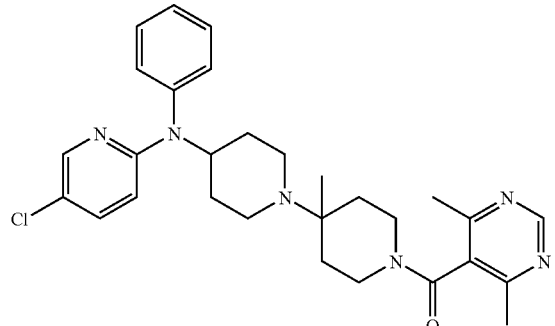 | 1 | 519.2632 |
| 79 | | 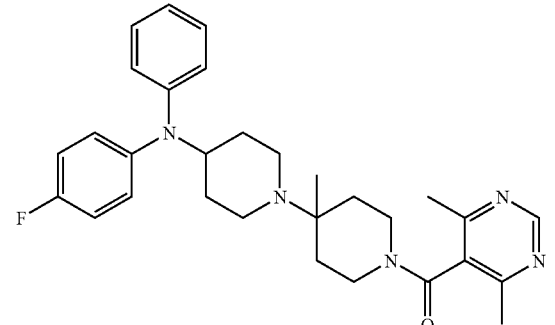 | 1 | 502.2989 |

TABLE 4-continued
| Example | SCH | Structure | HIV Replication (luciferase) IC50 nM | HRMS found (MH+) |
|---|---|---|---|---|
| 80 | | 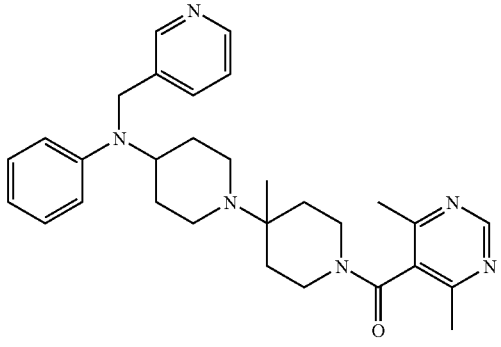 | 2 | 499.3180 |
| 81 | | 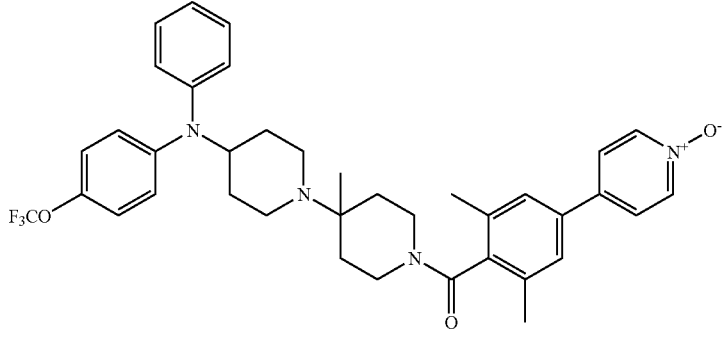 | 3 | 659.3199 |
| 82 | | 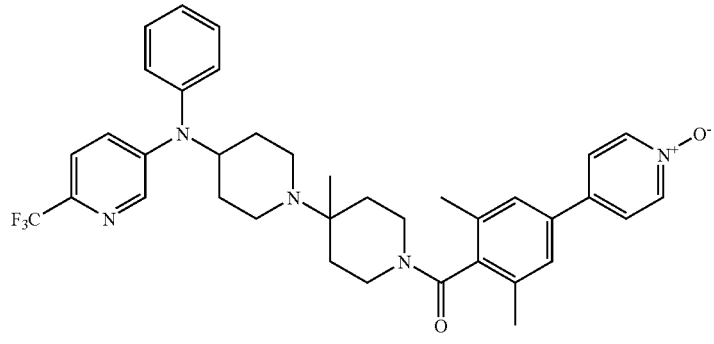 | 0.1 | 644.3220 |
| 83 | | 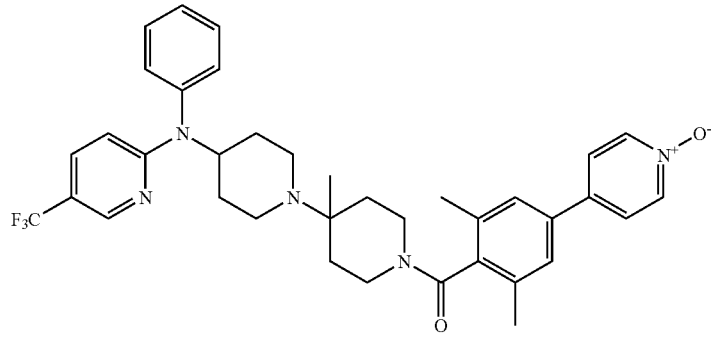 | 0.05 | 644.3226 |

TABLE 4-continued
| Example | SCH | Structure | HIV Replication (luciferase) IC50 nM | HRMS found (MH+) |
|---|---|---|---|---|
| 84 | | 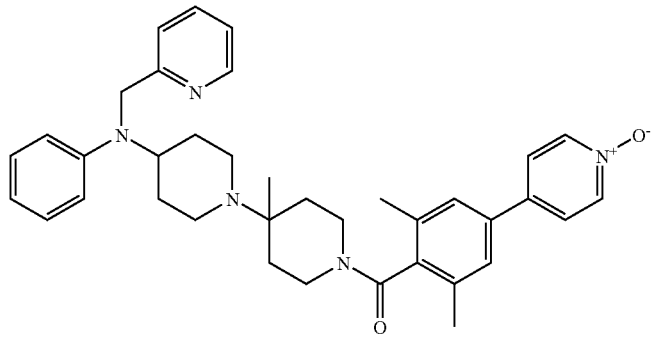 | 10 | 590.3490 |
| 85 | | 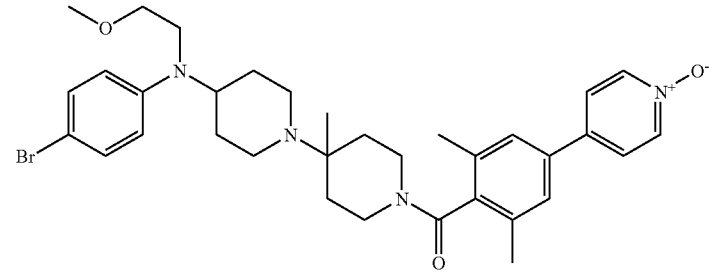 | 2 | 504.3696 |
| 86 | | 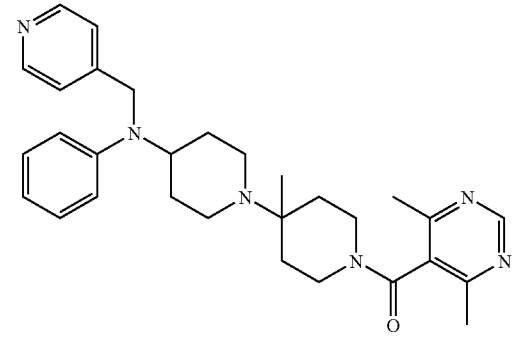 | 75 | 499.3193 |
| 87 | | 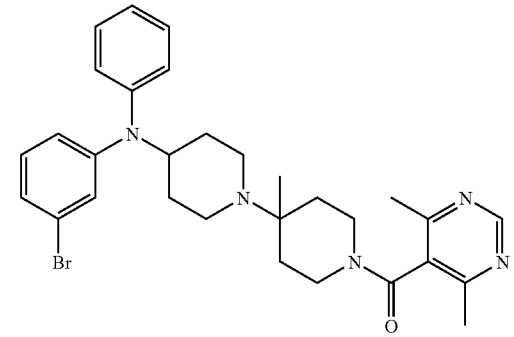 | 0.1 | 56202194 |

TABLE 4-continued
| Example | SCH | Structure | HIV Replication (luciferase) IC50 nM | HRMS found (MH+) |
|---|---|---|---|---|
| 88 | | 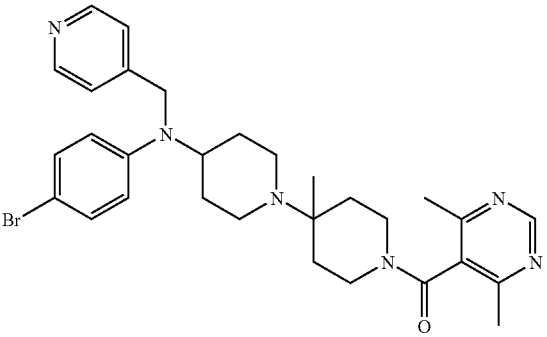 | 5 | 577.2297 |
| 89 | | 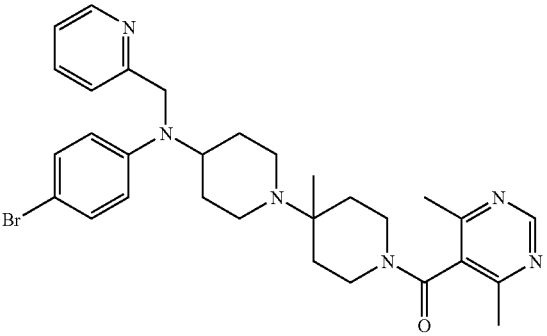 | 0.8 | 577.2286 |
| 90 | | 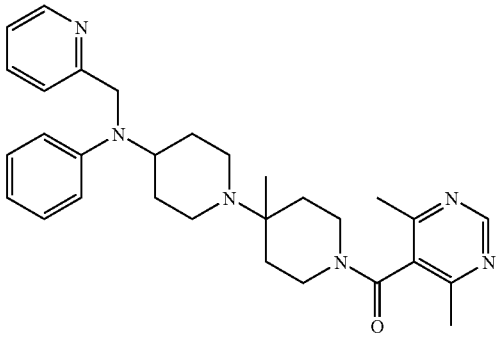 | 3.4 | 499.3180 |
| 91 | | 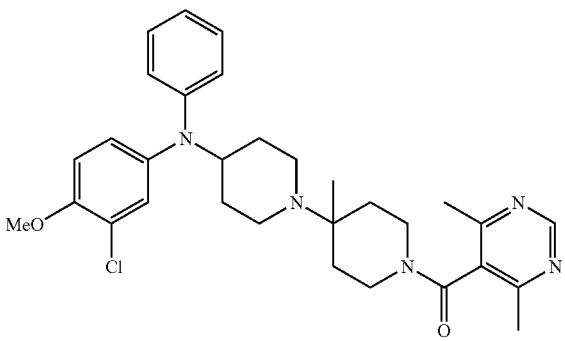 | 0.12 | 548.2795 |

TABLE 4-continued

| Example | SCH | Structure | HIV Replication (luciferase) IC50 nM | HRMS found (MH+) |
|---|---|---|---|---|
| 92 | | 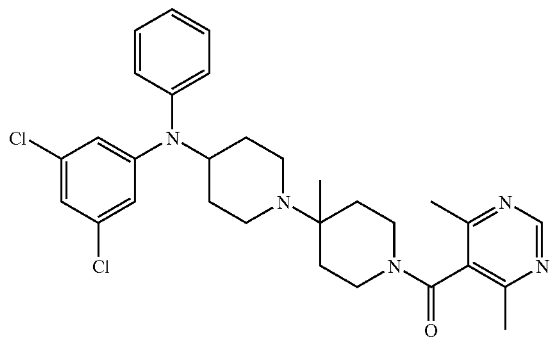 | 4.1 | 552.2293 |
| 93 | | 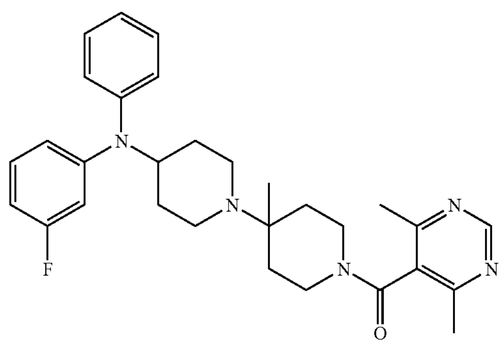 | 0.21 | 502.2975 |
| 94 | | 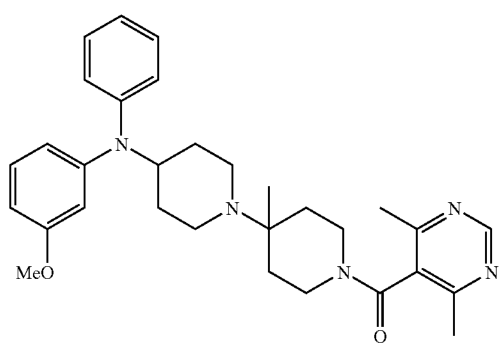 | 1 | 514.3178 |
| 95 | | 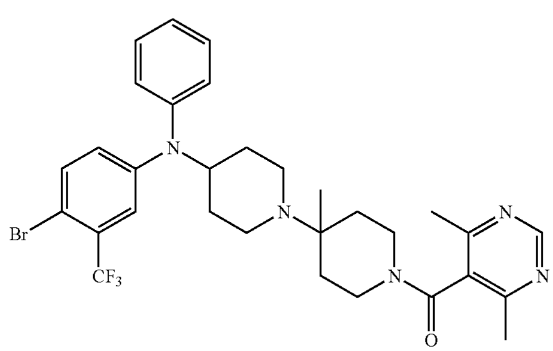 | 2 | 632.2051 |

TABLE 4-continued

| Example | SCH | Structure | HIV Replication (luciferase) IC50 nM | HRMS found (MH+) |
|---------|-----|-----------|---------------------------------------|------------------|
| 96 | | 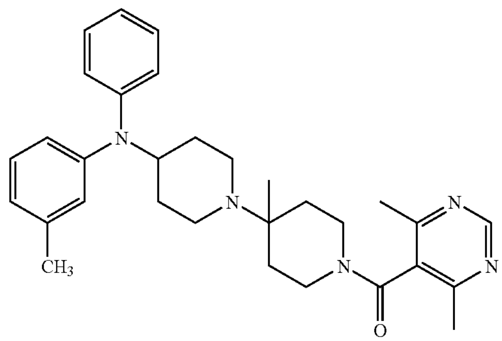 | 0.3 | 498.3226 |
| 97 | | 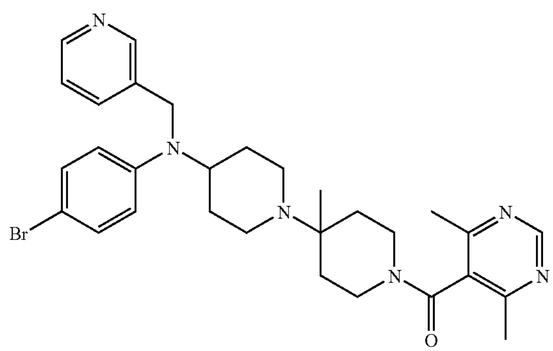 | 0.3 | 579.2271 |
| 98 | | 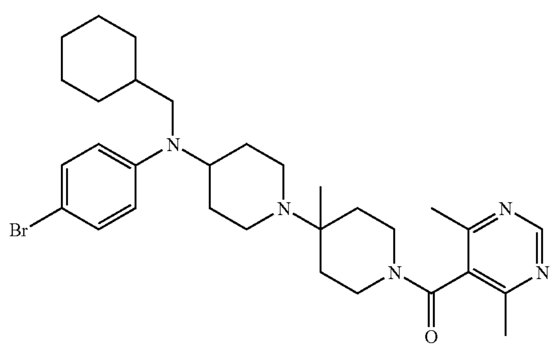 | 2 | 582.2808 |
| 99 | | 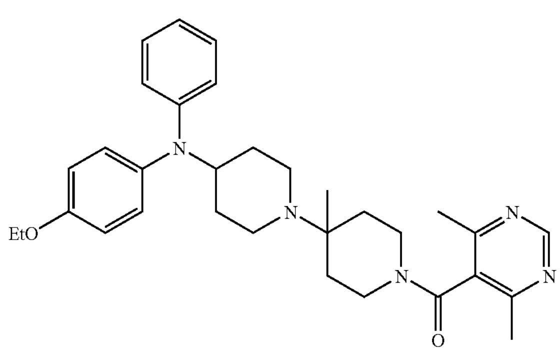 | 0.3 | 528.3343 |

TABLE 4-continued
| Example | SCH | Structure | HIV Replication (luciferase) IC50 nM | HRMS found (MH+) |
|---|---|---|---|---|
| 100 | | 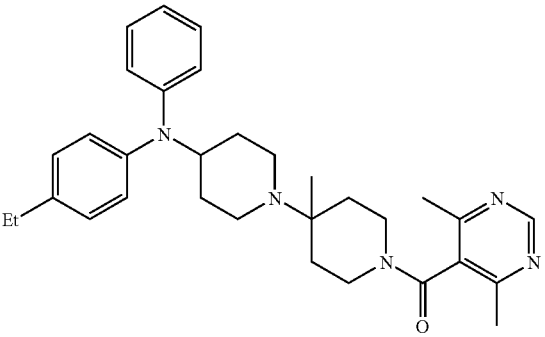 | 0.1 | 512.3386 |
| 101 | | 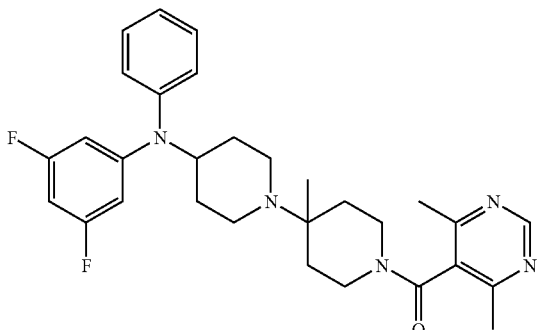 | 0.1 | 520.2890 |
| 102 | | 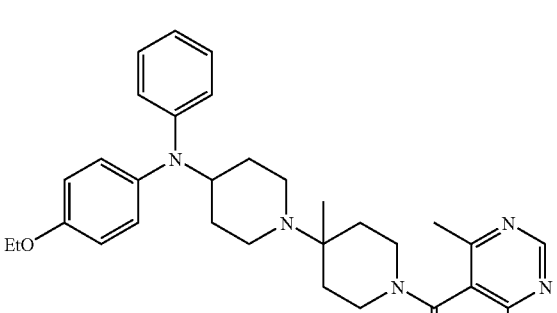 | 0.3 | 514.3178 |
| 103 | | 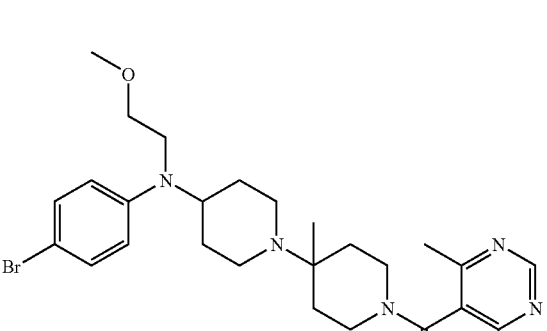 | 2 | 546.2297 |

TABLE 4-continued

| Example | SCH | Structure | HIV Replication (luciferase) IC50 nM | HRMS found (MH+) |
|---|---|---|---|---|
| 104 | | 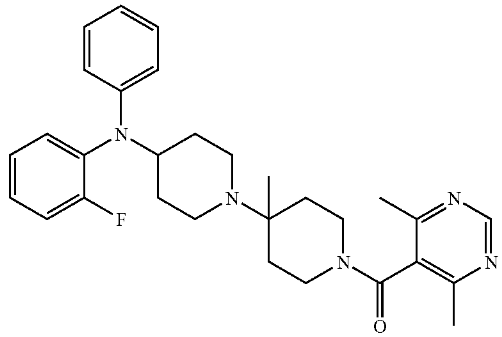 | 3 | 502.2975 |
| 105 | | 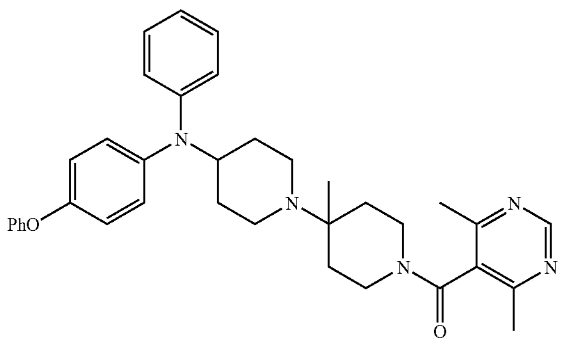 | 5 | 576.3334 |
| 106 | | 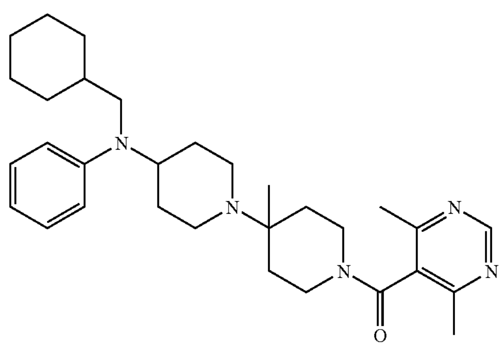 | 1 | 504.3696 |
| 107 | | 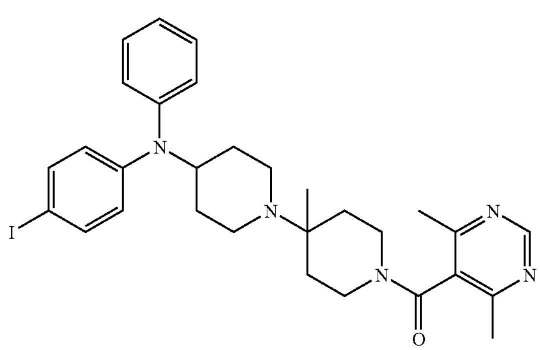 | 1 | 610.2057 |

EXAMPLE 4

Compound 108

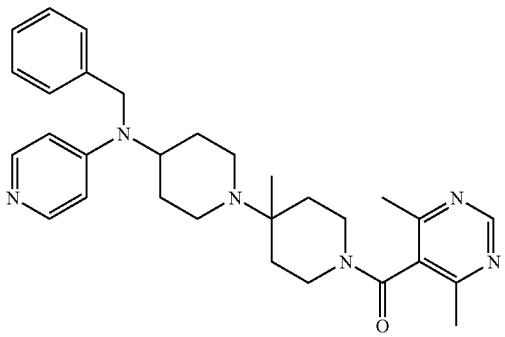

Step 1

The ketone 5 (5.0 g, 16.9 mmol), benzyl amine (1.67 mL, 15.3 mmol), Na(AcO)$_3$BH (3.89 g, 18.4 mmol), and ACOH (1.1 mL, 18.4 mL) were taken up in CH$_2$Cl$_2$ and stirred at 25° C. for 18 hours. The solution was diluted with CH$_2$Cl$_2$ and quenched with 1 N NaOH. The aqueous layer was extracted with CH$_2$Cl$_2$. The combined organic layers were dried (Na$_2$SO$_4$). Filtration and concentration followed by purification via flash chromatography (20/1 CH$_2$Cl$_2$/7 N NH$_3$ in MeOH, SIO$_2$) gave 5.79 g (97%) of an amine product.

Step 2

The amine from step 1 (200 mg, 0.52 mmol), 4-bromo-pyridine HCl (202 mg, 1.04 mmol), Pd(OAc)$_2$ (23 mg, 0.1 mmol), P(tBu)$_3$ (84 mg, 0.42 mmol), and NaOtBu (200 mg, 2.1 mmol) were taken up in toluene and heated at 110° C. for 17 hours. The solution was cooled and partitioned between EtOAc and water. The aqueous layer was extracted with EtOAc. The combined organic layers were washed with brine and dried in Na$_2$SO$_4$. Filtration and concentration followed by purification via preparative thin-layer chromatography (30/1 CH$_2$Cl$_2$/7N NH$_3$ in MeOH SiO$_2$) gave 129 mg (54%) of an amino-pyridine product.

Steps 3 and 4

The Boc amine from step 2 is treated according to the procedures described above in steps 6 and 7 in Example 2. Purification via preparative thin-layer chromatography (30/1 CH$_2$Cl$_2$/7 N NH$_3$ in MeOH, SiO2) gave 95 mg (68%) of an amide product (Compound 108). The amide was taken up in EtOAc and was precipitated as the HCl salt upon addition of 2.0M HCl in Et$_2$O. m.p. (HCl salt): 182-189 C. HRMS (MH+) calc'd for 499.3185; Found: 499.3181. IC$_{50}$=0.8 nm The following compound was prepared via similar procedures:

TABLE 5

| Example | Structure | HIV Replication (luciferase) IC50 nM | HRMS found (MH$^+$) |
|---|---|---|---|
| 109 | 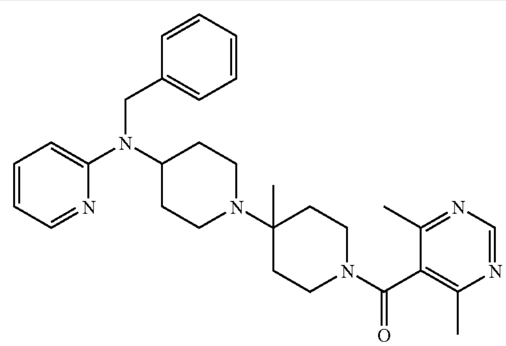 | 0.3 | 499.3180 |

EXAMPLE 5

Compound 110

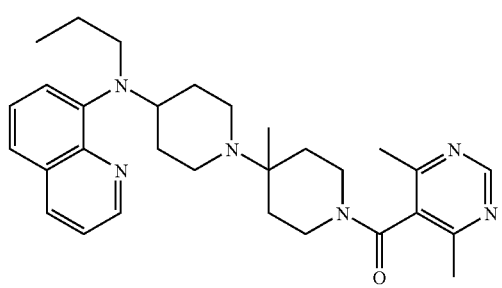

Step 1

8-Amino quinoline (1.0 g, 6.9 mmol), ketone 5 (3.08 g, 10.4 mmol), AcOH (1.1 mL, 19.3 mmol), and Na(AcO)$_3$BH (2.9 g, 10.4 mmol) were taken up in 30 mL ClCH$_2$CH$_2$Cl and stirred at 25° C. for 16 hours. The solution was diluted with CH$_2$Cl$_2$ and quenched with 1M NaOH. The aqueous layer was extracted with CH$_2$Cl$_2$. The combined organic layers were dried over Na$_2$SO$_4$, filtered, and concentrated. The crude product was purified via flash chromatography (gradient 2:1-1:1 hexanes/EtOAc) to afford 2.66 g (91%) of an aniline product.

Step 2

The aniline (85 mg, 0.20 mmol), propanal (23 mg, 0.4 mmol), and Na(AcO)$_3$BH were taken up in CH$_2$Cl$_2$ (2 mL). The solution was allowed to stir at 25° C. for 16 hours. The solution was diluted with CH$_2$Cl$_2$ and quenched with 1 M NaOH. The aqueous layer was extracted with CH$_2$Cl$_2$. The combined organic layers were dried over Na$_2$SO$_4$, filtered, and concentrated to afford 100 mg of a tertiary amine. The product was used without further purification.

Step 3

The Boc carbamate and 4.0 M HCl in dioxane (2 mL) were taken up in MeOH (4 mL) and the solution was stirred at 25° C. for 3 hours. The solution was concentrated. The HCl salt of the deprotected amine produced here here was used as is in the next step.

Step 4

The HCl salt from step 3, EDCI hydrochloride (61 mg, 0.032 mmol), HOBt (43 mg, 0.032 mmol), iPr$_2$Net (0.365 mL, 2.1 mmol), and 4,6-dimethyl-3-pyrimidine carboxylic acid (49 mg, 0.32 mmol) were taken up in MeCN (2 mL) and stirred at 25° C. for 24 hours. The solution was concentrated. The residue was parttioned between EtOAc and 1 N NaOH. The aqueous layer was extracted with EtOAc. The combined organic layers were washed with brine and dried over Na$_2$SO$_4$, filtered and concentrated. Purification via preparative, thin-layer chromagotraphy (95/5 CH$_2$Cl$_2$/MeOH) gave 60 mg (57%) of an amide product (Compound 110). The amide was taken up in EtOAc and was precipitated as the HCl salt upon addition of 2.0 M HCl in Et$_2$O. m.p. (HCl salt): 181° C. (decomposition). HRMS (MH+) calc'd 501.3342; found: 501.3349. IC$_{50}$=23 nm

EXAMPLE 6

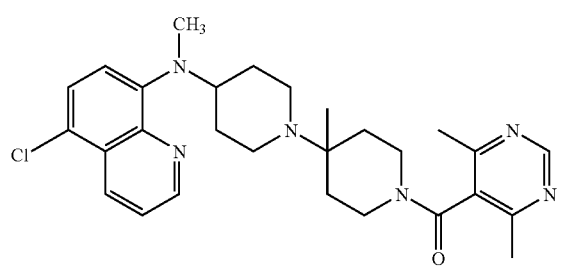

Compound 111

Step 1

8-amino quinoline (4.5 g, 31.3 mmol), N-chlorosuccinimide (4.80 g, 36 mmol) was taken up in iPrOH (50 mL) at 60° C. The mixture was heated to reflux and stirred for 20 min. The solution was cooled to 25° C. and concentrated to ⅓ original volume. The mixture was partitioned between CH$_2$Cl$_2$ and water. The aqueous layer was extracted with CH$_2$Cl$_2$. The combined organic layers were dried over Na$_2$SO$_4$, filtered, and concentrated. The crude product was purified by flash chromatography (5:1 hexanes/EtOAc) to afford 1.90 g (34%) of a 8-amino-4-chloroquinoline product.

Step 2

The quinoline (1.28 g, 7.2 mmol) (3.18 g, 10.7 mmol), ACOH (1.16 mL, 20.1 mmol), and Na(AcO)$_3$BH (3.05 g, 14.4 mmol) were taken up in 30 mL ClCH$_2$CH$_2$Cl and stirred at 25° C. for 16 hours. The solution was diluted with CH$_2$Cl$_2$ and quenched with 1M NaOH. The aqueous layer was extracted with CH$_2$Cl$_2$. The combined organic layers were dried over Na$_2$SO$_4$, filtered, and concentrated. The crude product was purified via flash chromatography (2:1 hexanes/EtOAc) to afford 2.0 g (61%) of the quinoline as a yellow oil/foam.

Step 3

The quinoline from step 2(144 mg, 031 mmol), methyl iodide (67 mg, 0.47 mmol), and cesium carbonate (153 mg, 0.47 mmol) was taken up in DMF (3 mL) in a sealed tube and heated to 100° C. for 24 hours. The mixture was cooled to 25° C. and diluted with EtOAc. The organic layer was washed with water followed by brine. The organic layer was dried over Na$_2$SO$_4$, filtered, and concentrated. The crude product was purified via preparative, thin-layer chromagotraphy (2:1 hexanes/EtOAc) to afford 14 mg (10%) of a methylated amine product.

Step 4

The product of step 3 was treated as described above for Example 5 (steps 3 and 4) to furnish the crude pyrimidine amide. Purification via preparative, thin-layer chromagotraphy (99:1 95/5 CH$_2$Cl$_2$/MeOH:7 N NH$_3$ in MeOH) gave 8 mg (53%) of Compound 111. The amide was taken up in EtOAc and was precipitated as the HCl salt upon addition of 2.0 M HCl in Et$_2$O. m.p. (HCl salt): 164-167° C. (decomposition). HRMS (MH+) calc'd 507.2639; found: 507.2634.

EXAMPLE 7

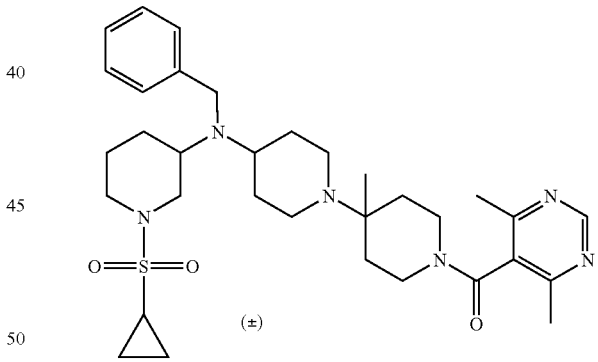

Compound 112

(±)

Step 1

Compound 108 (10.5 grams) and TFA (20 mL) were taken up in CH$_2$Cl$_2$ and stirred at 25 C for 12 hours. The solution was concentrated, and the residue was partitioned beween CH$_2$Cl$_2$ and 1 N NaOH. The aqueous layer was extracted with CH$_2$Cl$_2$. The combined organic layers were dried (Na$_2$SO$_4$). Filtration and concentration gave an amine product.

Step 2

The amine from step 1,4,6-dimethyl-3-pyrimidine carboxylic acid (6 g), EDCI (8.6 g), and iPr$_2$NEt (7.8 g) were taken up in CH$_3$CN and stirred at 25° C. for 10 hours. The solution was concentrated, and the residue was partitioned beween EtOAc and 1 N NaOH. The aqueous layer was extracted with CH$_2$Cl$_2$. The combined organic layers were washed with brine and dried (Na$_2$SO$_4$). Purification via flash chromatography (3%-5% MeOH in CH$_2$Cl$_2$, SiO$_2$) gave 4.9 grams of a pyrimidine-ketone product.

Step 3

The ketone from step 2 (1.65 g, 4.99 mmol), Na(OAc)$_3$BH (2.1 g), AcOH (1 g), and (+/−)-3-amino-N-Boc-piperidine (1 g) were taken up in CH$_2$Cl$_2$ and stirred at 25° C. for 48 hours. The solution was diluted with CH$_2$Cl$_2$ and washed with 1 N NaOH. The aqueous layer was extracted with CH$_2$Cl$_2$. The combined organic layers were dried (Na$_2$SO$_4$). Filtration and concentration followed by purification via flash chromatography (3%-10% 7N NH$_3$ in MeOH/CH$_2$Cl$_2$, SiO$_2$) gave 1.7 g (66%) of an amine product.

Step 4

The amine from step 3 (400 mg), benzyl bromide (0.2 mL), Cs$_2$CO$_3$ (1 g), and KI (10 mg) were heated in DMF at 100 C for 12 hours. The solution was partitioned between EtOAc and water. The aqueous layer was exracted with EtOAc. The combined organic layers were washed with brine and dried (Na$_2$SO$_4$). Filtration and concentration followed by purification via flash chromatography (3% MeOH in CH$_2$Cl$_2$, SiO$_2$) gave 300 mg of a benzyl amine product.

Step 5

The amine from step 4 (300 mg) and 4.0M HCl in dioxane (10 mL) were taken up in MeOH and stirred at 25° C. for 10 hours. The solution was concentrated. The residue was partitioned between CH$_2$Cl$_2$. The aqueous layer was extracted with CH$_2$Cl$_2$. The combined organic layers were dried (Na$_2$SO$_4$). Filtration and concentration gave 200 mg of a deprotected amine product.

Step 6

The amine from step 5 (100 mg) and cyclopropylsulfonyl chloride (50 mg) were partitioned between CH$_2$Cl$_2$ and 1 N NaOH. The mixture was stirred vigorously at 25° C. for 2 h. The layers were separated and the aqueous layer was extracted with CH$_2$Cl$_2$. The combined organic layers were dried with Na$_2$SO$_4$. Filtration and concentration followed by purification via preparative thin-layer chromatography (9% MeOH in CH$_2$Cl$_2$, SiO$_2$) gave 50 mg of amide product (Compound 112). The amide was taken up in EtOAc and was precipitated as the HCl salt upon addition of 2.0M HCl in Et$_2$O. m.p. (HCl salt): 190-195° C. HRMS (MH+) calc'd for 609.3587; Found: 609.3578. IC$_{50}$=30 nm The following compound was prepared via similar procedures:

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed:

1. A compound represented by the structural formula I

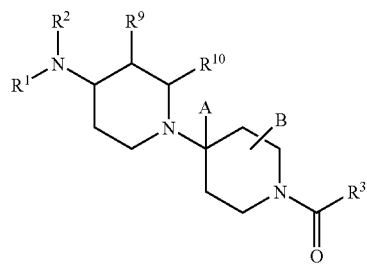

I or a pharmaceutically acceptable salt thereof; wherein:
$R^1$ is

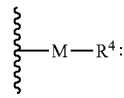

$R^2$ is benzyl or 4-fluorobenzyl;
$R^3$ selected from the group consisting of 6-membered heteroaryl, and 6-membered heteroaryl-N-oxide, wherein said, 6-membered heteroaryl or heteroaryl-N-oxide is pyrimidine or pyrimidine-N-oxide respectively, each of which is optionally substituted with 1-4 substituents which can be the same or different and, are independently selected from the group consisting of $R^{11}$, $R^{12}$, $R^{13}$, $R^{14}$ and $R^{15}$;
$R^4$ is 1-3 substituents selected from the group consisting of H, halo, alkyl, haloalkyt, alkoxy, cycloalkyl, amide, CF$_3$, OCF$_3$, aryl, heteroaryl, —XR$^7$, —CN, —CO$_2$H, —CO$_2$R$^{22}$, R$^8$-aryl(C$_1$-C$_6$)alky-, R$^8$-heteroaryl(C$_1$-C$_6$)alkyl-, —C(O)NR$^{21}$R$^{22}$, —C(O)NH$_2$, wherein R$^4$ can

TABLE 6

| Example | Structure | HIV Replication (luciferase) IC50 nM | HRMS found (MH$^+$) |
|---|---|---|---|
| 113 | | 40 | 583.3422 | be the same or different and is independently selected when there is more than one $R^4$ present;

$R^7$ is selected from the group consisting of aryl substituted aryl, heteroaryl, alkyl, haloalkyl and cycloalkyl;

$R^8$ is 1, 2 or 3 substituents selected from the group consisting of H, halo, $(C_1$-$C_6)$alkyl, $(C_1$-$C_6)$alkoxy, —$CF_3$, —$OCF_3$, $CH_3C(O)$—, —CN, $CH_3SO_2$—, $CF_3SO_2$— and —$NH_2$, wherein $R^8$ can be the same or different and is independently selected when there are more than one $R^8$ present;

$R^9$, $R^{10}$ and B can be the same or different and are each independently selected from the group consisting of hydrogen, $(C_1$-$C_6)$alkyl, and —$(C_1$-$C_6)$heteroalkyl;

$R^{11}$ and $R^{12}$ can be the same or different and are each independently selected from the group consisting of —$(C_1$-$C_6)$alkyl, —$(C_1$-$C_6)$haloalkyl, halogen, —$NR^{19}R^{26}$, —OH, $CF_3$, —$OCH_3$, —O-acyl, and —$OCF_3$;

$R^{13}$ is selected from the group consisting of hydrogen, $R^{11}$, H, phenyl, $NO_2$, —CN, —$CH_2F$, —$CHF_2$, —CHO, —CH=$NOR^{19}$, pyridyl-N-oxide, pyrimidinyl, pyrazinyl, $N(R^{20})CON R^{20}R^{21}$, —NHCONH(chloro-$(C_1$-$C_6)$alkyl), —NHCONH$((C_3$-$C_{10})$-cycloalkyl$(C_1$-$C_6)$alkyl), —NHCO$(C_1$-$C_6)$alkyl, —$NHCOCF_3$, —$NHCOCF_3$, —$NHSO_2((C_1$-$C_6)$alkyl, —$NHSO_2(C_1$-$C_6)$alkyl, —$N(SO_2CF_3)2$, —$NHCO_2(C_1$-$C_6)$alkyl, $(C_3$-$C_{10})$cycloalkyl, —$SR^{22}$, $SOR^{22}$, —$SO_2R^{22}$, —$SO_2N$ H$(C_1$-$C_6)$alkyl, —$OSO_2(C_1$-$C_6)$alkyl, —$OSO_2CF_3$, hydroxy$(C_1$-$C_6)$alkyl, —$CONR^{19}R^{20}$, —CON $(CH_2CH_2$—O—$CH_3)_2$, —$OCONH(C_1$-$C_6)$alkyl, —$CO_2R^{19}$, $Si(CH_3)_3$ and —$B(OC(CH_3)_2)_2$;

$R^{14}$ is selected from the group consisting of $(C_1$-$C_6)$alkyl, —$(C_1$-$C_6)$haloalkyl —$NH_2$ and $R^{15}$-phenyl;

$R^{15}$ is 1-3 substituents selected from the group consisting of hydrogen, $(C_1$-$C_6)$alkyl, $(C_1$-$C_6)$haloalkyl, —$CF_3$, —$CO_2R^{20}$, —CN, $(C_1$-$C_6)$alkoxy and halogen; wherein $R^{15}$ can be the same or different and is independently selected when there are more than one $R^{15}$ present;

$R^{19}$, $R^{20}$ and $R^{21}$ can each be the same or different and are each independently selected from the group consisting of H, $(C_1$-$C_6)$alkyl and $(C_3$-$C_6)$cycloalkyl;

$R^{22}$ is selected from the group consisting of —$(C_1$-$C_6)$alkyl, -$(C_1$-$C_6)$haloalkyl, —$(C_2$-$C_6)$hydroxyalkyl, $(C_2$-$C_6)$alkylene, $(C_3$-$C_6)$cycloalkyl, aryl and aryl$(C_1$-$C_6)$alkyl-;

A is selected from the group consisting of H, $(C_1$-$C_6)$alkyl, and $(C_2$-$C_6)$alkenyl, M is aryl optionally substituted with $R^4$; and X is selected from the group consisting of $CH_2$, $SO_2$, SO, S, and O, with the following proviso: when $R^1$ is phenyl, or naphthyl, $R^2$ cannot be H, $(C_1$-$C_6)$alkyf or —C(O)—$(C_1$-$C_6)$alky.

2. A compound having the structural formula I according to claim 1 or a pharmaceutically acceptable salt thereof, wherein $R^9$, $R^{10}$ and B are H, A is —$CH_3$, and $R^1$, $R^2$ and $R^3$ are as defined in the following table:

| # | $R^1$ | $R^2$ | $R^3$ |
|---|---|---|---|
| 8 | 4-Br-phenyl | benzyl | 4,6-dimethylpyrimidin-5-yl |
| 9 | phenyl | benzyl | 4,6-dimethylpyrimidin-5-yl |
| 10 | 4-$CF_3$-phenyl | benzyl | 4,6-dimethylpyrimidin-5-yl |
| 11 | 4-$CF_3O$-phenyl | benzyl | 4,6-dimethylpyrimidin-5-yl |

-continued
| # | R¹ | R² | R³ |
|---|----|----|----|
| 12 | 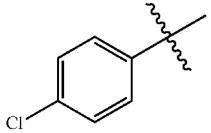 | 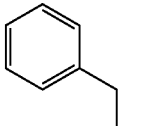 | 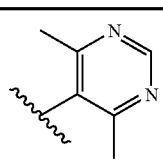 |
| 14 | 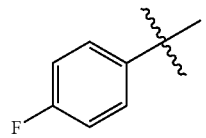 | 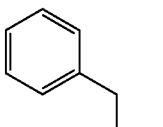 | 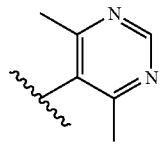 |
| 17 | 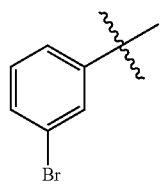 | 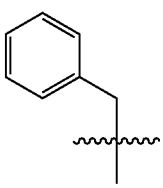 | 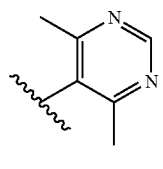 |
| 18 | 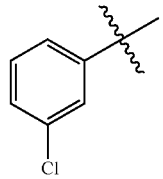 | 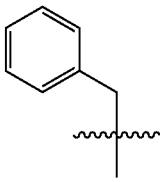 | 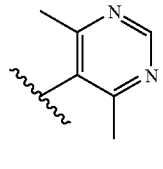 |
| 19 | 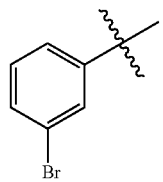 | 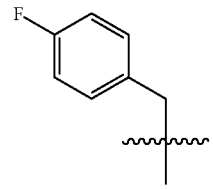 | 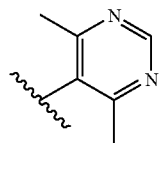 |
| 20 | 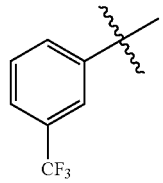 | 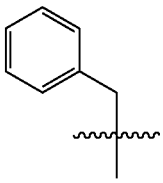 | 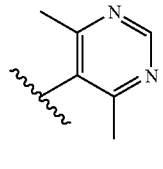 |
| 21 | 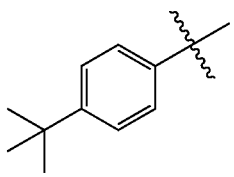 | 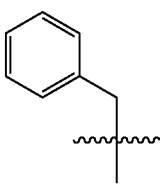 | 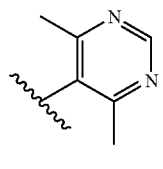 |
| 22 | 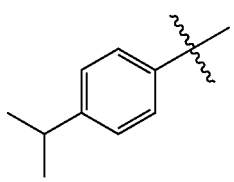 | 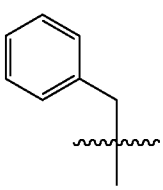 | 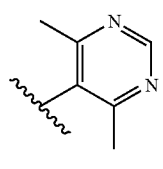 |

-continued
| # | R¹ | R² | R³ |
|---|---|---|---|
| 23 | 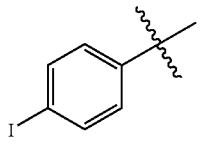 4-I-C₆H₄- | 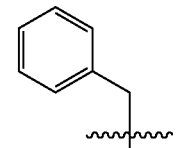 benzyl | 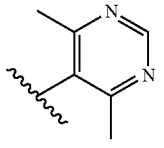 4,6-dimethylpyrimidin-5-yl |
| 24 | 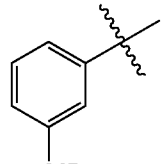 3-OCF₃-C₆H₄- | 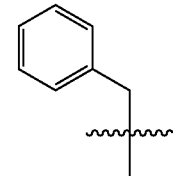 benzyl | 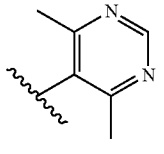 4,6-dimethylpyrimidin-5-yl |
| 25 | 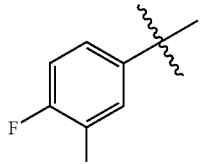 3,4-diF-C₆H₃- | 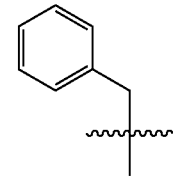 benzyl | 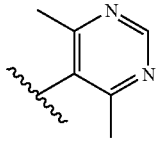 4,6-dimethylpyrimidin-5-yl |
| 26 | 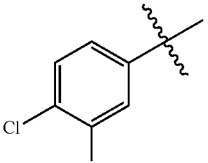 3,4-diCl-C₆H₃- | 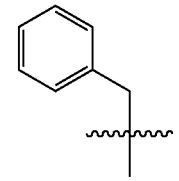 benzyl | 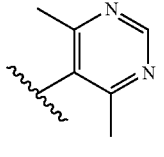 4,6-dimethylpyrimidin-5-yl |
| 27 | 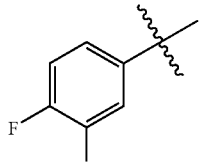 3-Cl-4-F-C₆H₃- | 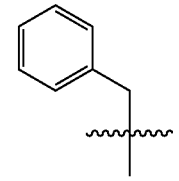 benzyl | 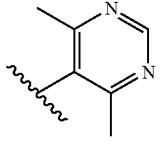 4,6-dimethylpyrimidin-5-yl |
| 28 | 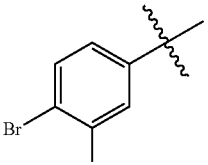 4-Br-3-CH₃-C₆H₃- | 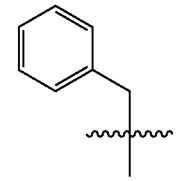 benzyl | 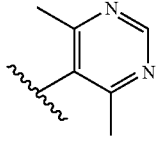 4,6-dimethylpyrimidin-5-yl |
| 29 | 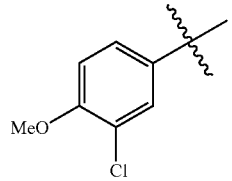 3-Cl-4-MeO-C₆H₃- | 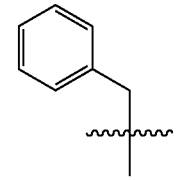 benzyl | 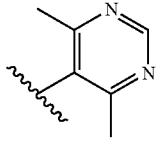 4,6-dimethylpyrimidin-5-yl |
| 31 | 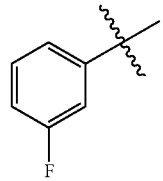 3-F-C₆H₄- | 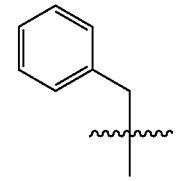 benzyl | 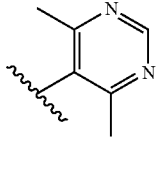 4,6-dimethylpyrimidin-5-yl |

-continued
| # | R¹ | R² | R³ |
|---|---|---|---|
| 32 | 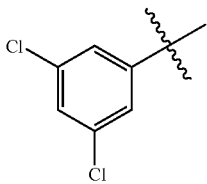 | 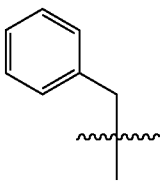 | 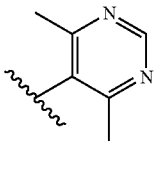 |
| 33 | 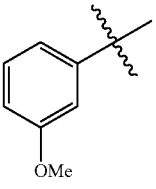 | 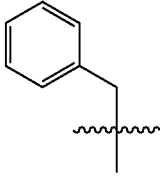 | 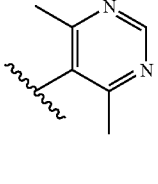 |
| 34 | 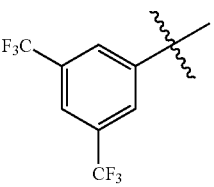 | 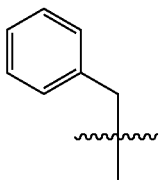 | 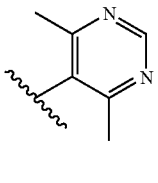 |
| 35 | 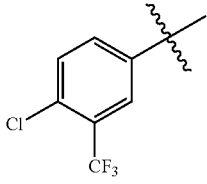 | 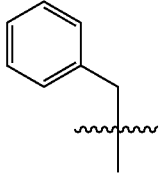 | 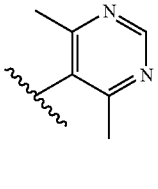 |
| 36 | 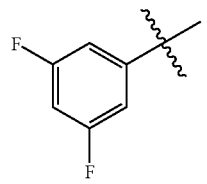 | 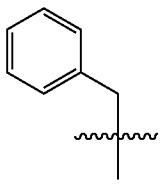 | 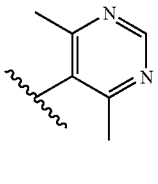 |
| 37 | 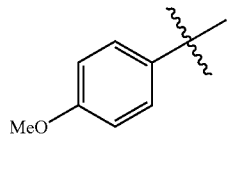 | 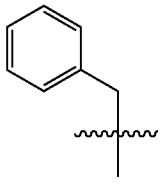 | 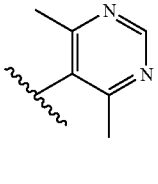 |
| 38 | 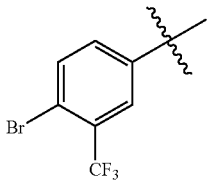 | 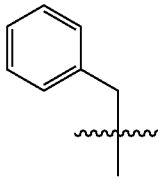 | 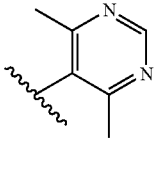 |

-continued
| # | R¹ | R² | R³ |
|---|----|----|----|
| 39 | 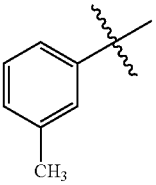 3-CH₃-C₆H₄- | 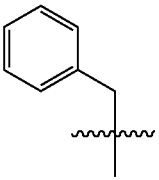 benzyl | 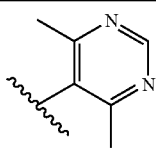 4,6-dimethylpyrimidin-5-yl |
| 40 | 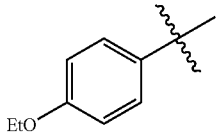 4-EtO-C₆H₄- | 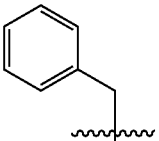 benzyl | 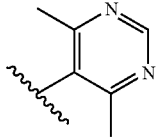 4,6-dimethylpyrimidin-5-yl |
| 41 | 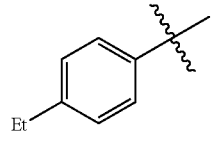 4-Et-C₆H₄- | 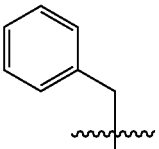 benzyl | 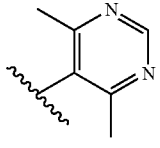 4,6-dimethylpyrimidin-5-yl |
| 42 | 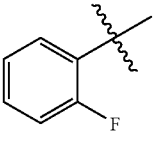 2-F-C₆H₄- | 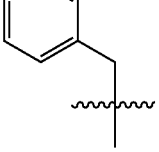 benzyl | 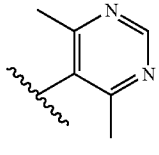 4,6-dimethylpyrimidin-5-yl |
| 43 | 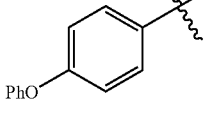 4-PhO-C₆H₄- | 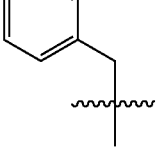 benzyl | 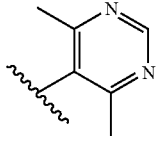 4,6-dimethylpyrimidin-5-yl |
| 44 | 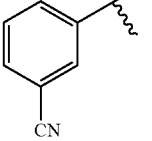 3-CN-C₆H₄- | 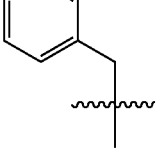 benzyl | 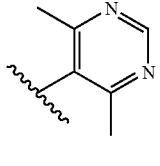 4,6-dimethylpyrimidin-5-yl |
| 50 | 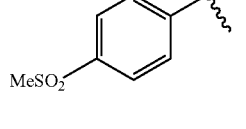 4-MeSO₂-C₆H₄- | 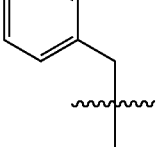 benzyl | 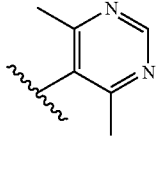 4,6-dimethylpyrimidin-5-yl |
| 59 | 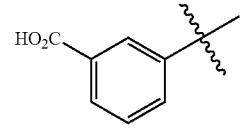 3-HO₂C-C₆H₄- | 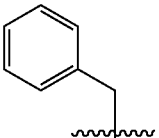 benzyl | 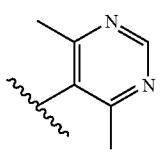 4,6-dimethylpyrimidin-5-yl |

-continued

| # | R¹ | R² | R³ |
|---|---|---|---|
| 60 | 4-(HO₂C)phenyl- | benzyl | 4,6-dimethylpyrimidin-5-yl |
| 61 | 3-(H₂NC(O))phenyl- | benzyl | 4,6-dimethylpyrimidin-5-yl |
| 63 | 3-(Et₂NC(O))phenyl- | benzyl | 4,6-dimethylpyrimidin-5-yl |
| 65 | 3-(PhNHC(O))phenyl- | benzyl | 4,6-dimethylpyrimidin-5-yl |
| 66 | 3-(BnNHC(O))phenyl- | benzyl | 4,6-dimethylpyrimidin-5-yl |
| 67 | 3-(HOCH₂CH₂NHC(O))phenyl- | benzyl | 4,6-dimethylpyrimidin-5-yl |
| 68 | 3-(cyclopropyl-NHC(O))phenyl- | benzyl | 4,6-dimethylpyrimidin-5-yl |

3. A compound according to claim 2 or a pharmaceutically acceptable salt thereof, wherein $R^1$, $R^2$ and $R^3$ each represent:

| # | $R^1$ | $R^2$ | $R^3$ |
|---|---|---|---|
| 10 | 4-CF₃-phenyl | benzyl | 5-(4,6-dimethylpyrimidinyl) |
| 11 | 4-CF₃O-phenyl | benzyl | 5-(4,6-dimethylpyrimidinyl) |
| 12 | 4-Cl-phenyl | benzyl | 5-(4,6-dimethylpyrimidinyl) |
| 14 | 4-F-phenyl | benzyl | 5-(4,6-dimethylpyrimidinyl) |
| 17 | 3-Br-phenyl | benzyl | 5-(4,6-dimethylpyrimidinyl) |
| 28 | 4-Br-3-methyl-phenyl | benzyl | 5-(4,6-dimethylpyrimidinyl) |
| 29 | 4-MeO-3-Cl-phenyl | benzyl | 5-(4,6-dimethylpyrimidinyl) |

-continued
| # | R¹ | R² | R³ |
|---|---|---|---|
| 31 | 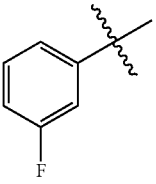 | 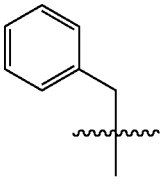 | 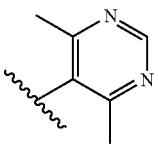 |
| 36 | 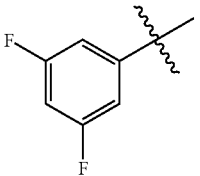 | 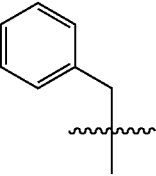 | 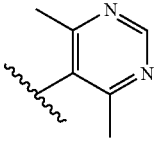 |
| 37 | 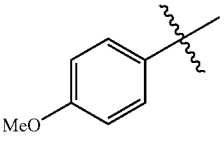 | 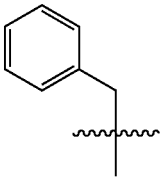 | 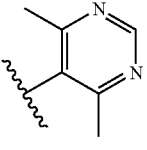 |
| 39 | 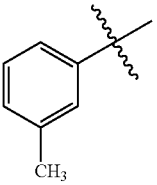 | 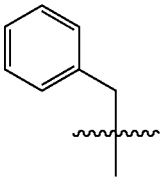 | 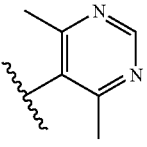 |
| 40 | 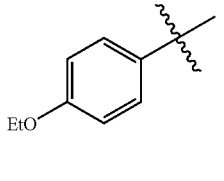 | 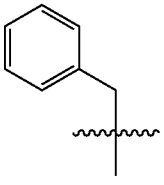 | 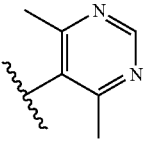 |
| 50 | 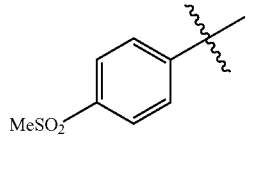 | 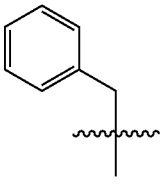 | 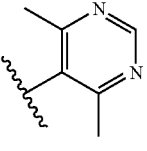 |
| 61 | 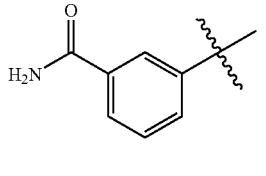 | 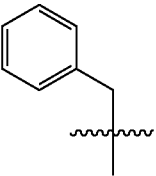 | 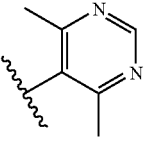 |
| 68 | 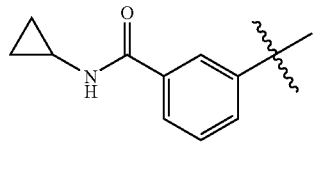 | 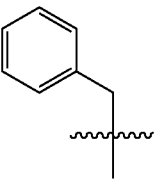 | 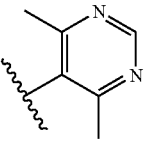 |

4. A compound according to claim 3 represented by the structural formulae:

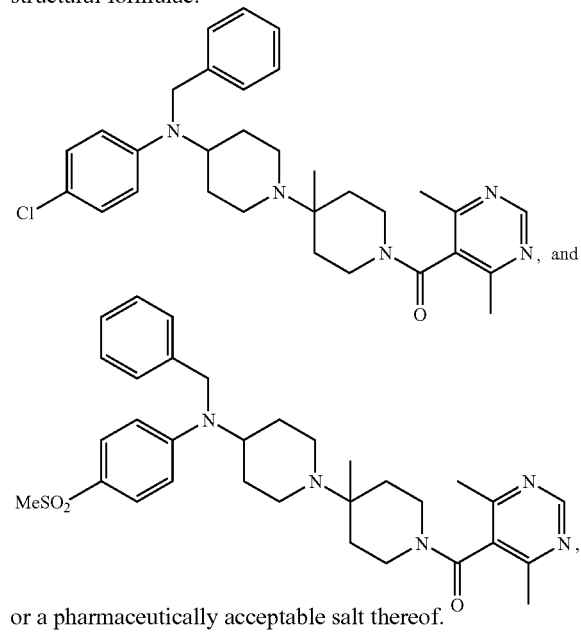

or a pharmaceutically acceptable salt thereof.

5. A pharmaceutical composition comprising one or more compounds of claim 1 or a pharmaceutically acceptable salt thereof.

6. A pharmaceutical composition comprising one or more compounds of claim 4 or a pharmaceutically acceptable salt thereof.

7. The pharmaceutical composition according to claim 5 further comprising one or more pharmaceutically acceptable carriers.

8. The pharmaceutical composition according to claim 6 further comprising one or more pharmaceutically acceptable carriers.

9. The pharmaceutical composition according to claim 5, wherein said pharmaceutical composition contains a therapeutically effective amount of said one or more compounds or a pharmaceutically acceptable salt thereof.

10. The pharmaceutical composition according to claim 6, wherein said pharmaceutical composition contains a therapeutically effective amount of said one or more compounds or a pharmaceutically acceptable salt thereof.

* * * * *